(12) United States Patent
Feinberg et al.

(10) Patent No.: US 10,898,313 B2
(45) Date of Patent: Jan. 26, 2021

(54) SYSTEMS, DEVICES AND METHODS OF MAKING MAMMARY IMPLANTS AND TISSUE EXPANDERS HAVING RIBBED SHELLS

(71) Applicant: Mentor Worldwide LLC, Irvine, CA (US)

(72) Inventors: Marc Feinberg, Ringoes, NJ (US); Joseph Henry Contiliano, Stewartsville, NJ (US); Vikram Garadi, Fort Worth, TX (US); John Haroutunian, Grapevine, TX (US)

(73) Assignee: Mentor Worldwide LLC, Irvine, CA (US)

( * ) Notice: Subject to any disclaimer, the term of this patent is extended or adjusted under 35 U.S.C. 154(b) by 0 days.

(21) Appl. No.: 16/528,797

(22) Filed: Aug. 1, 2019

(65) Prior Publication Data

US 2020/0046489 A1 Feb. 13, 2020

Related U.S. Application Data

(60) Provisional application No. 62/717,271, filed on Aug. 10, 2018.

(51) Int. Cl.
| | | |
|---|---|---|
| *A61F 2/12* | (2006.01) | |
| *B29C 41/14* | (2006.01) | |
| *A61B 90/00* | (2016.01) | |
| *A61L 27/18* | (2006.01) | |
| *B29L 31/00* | (2006.01) | |

(52) U.S. Cl.
CPC ............ *A61F 2/12* (2013.01); *B29C 41/14* (2013.01); *A61B 90/02* (2016.02); *A61L 27/18* (2013.01); *B29C 2791/001* (2013.01); *B29L 2031/7532* (2013.01)

(58) Field of Classification Search
USPC ........................................ 623/7–8
See application file for complete search history.

(56) References Cited

U.S. PATENT DOCUMENTS

| | | |
|---|---|---|
| 4,472,226 A | 9/1984 | Redinger et al. |
| 4,531,244 A | 7/1985 | Hamas |
| 5,104,409 A | 4/1992 | Baker |

(Continued)

FOREIGN PATENT DOCUMENTS

| | | |
|---|---|---|
| EP | 1510189 | 2/2005 |
| WO | 2018078446 | 5/2018 |

OTHER PUBLICATIONS

International Search Report issued in corresponding International Application No. PCT/IB2019/056618, dated Dec. 17, 2019, 5 pages.

*Primary Examiner* — Yashita Sharma
(74) *Attorney, Agent, or Firm* — Doherty IP Law Group LLC

(57) ABSTRACT

An implantable prosthesis includes a shell having an apex, a base, a radius located between the apex and the base, and a dome extending between the apex and the radius. The shell has an outer surface and an inner surface that surrounds an interior volume of the shell. At least one rib is integrally formed with the inner surface of the shell and projects inwardly from the inner surface of the shell into the interior volume of the shell. The shell has an interior volume that is adapted to receive a biocompatible filler material.

21 Claims, 63 Drawing Sheets

(56) References Cited

U.S. PATENT DOCUMENTS

| | | |
|---|---|---|
| 5,447,535 A | 9/1995 | Muller |
| 6,228,116 B1 * | 5/2001 | Ledergerber .......... A61F 2/0077 623/8 |
| 6,605,116 B2 | 8/2003 | Falcon et al. |
| 8,192,486 B2 | 6/2012 | Glicksman |
| 9,050,184 B2 | 6/2015 | Van Epps |
| 9,138,310 B2 | 9/2015 | Powell et al. |
| 9,138,311 B2 | 9/2015 | Van Epps et al. |
| 9,808,338 B2 | 11/2017 | Schuessler et al. |
| 9,918,829 B2 | 3/2018 | Van Epps et al. |
| 2003/0036803 A1 * | 2/2003 | McGhan ................. A61F 2/12 623/23.71 |
| 2008/0221679 A1 | 9/2008 | Hamas |
| 2010/0114312 A1 | 5/2010 | Glicksman |
| 2011/0046729 A1 | 2/2011 | Schuessler et al. |
| 2012/0259428 A1 | 10/2012 | Brogan et al. |
| 2013/0123918 A1 | 5/2013 | Glicksman |
| 2014/0088703 A1 | 3/2014 | Schuessler |
| 2018/0064530 A1 | 3/2018 | Glicksman |

* cited by examiner

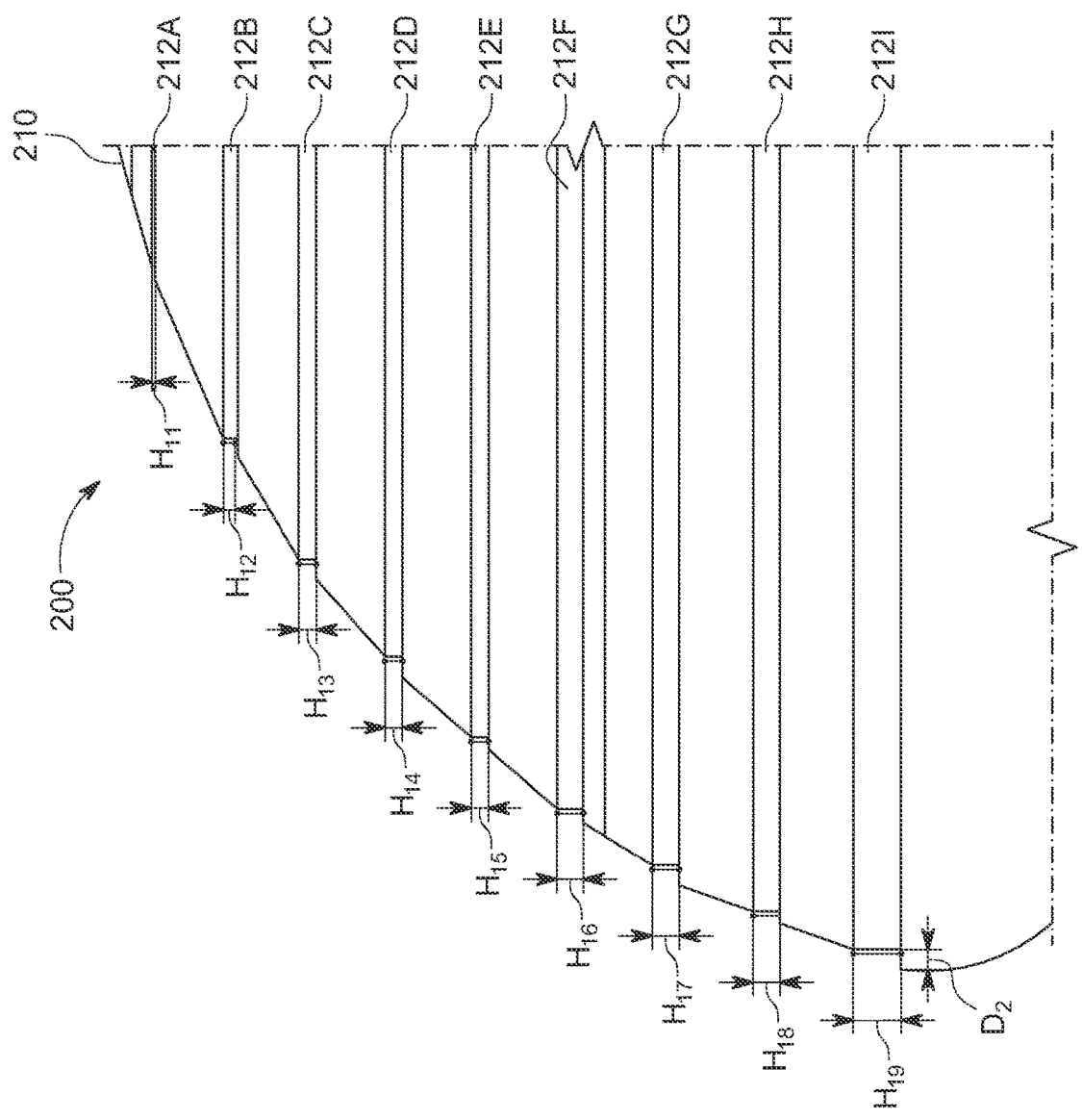

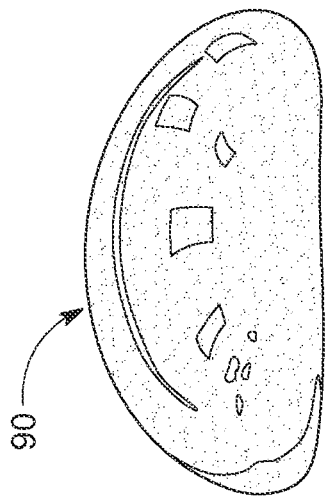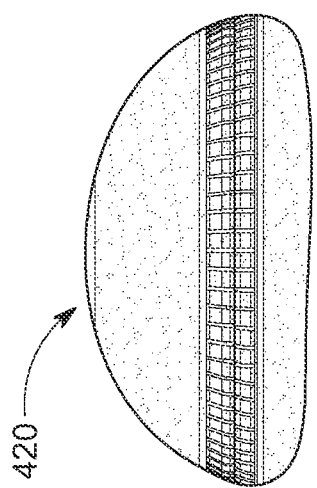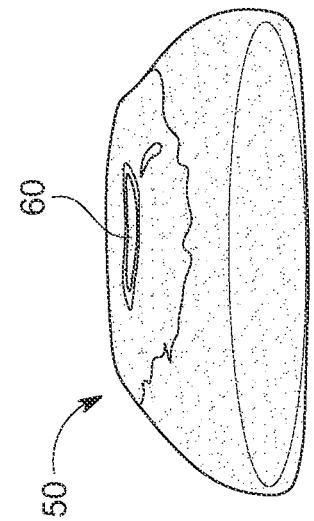
FIG. 32A
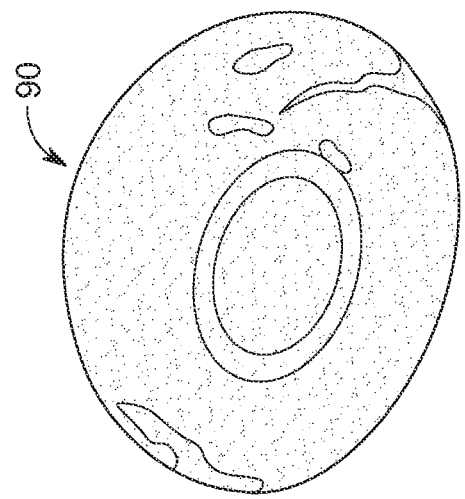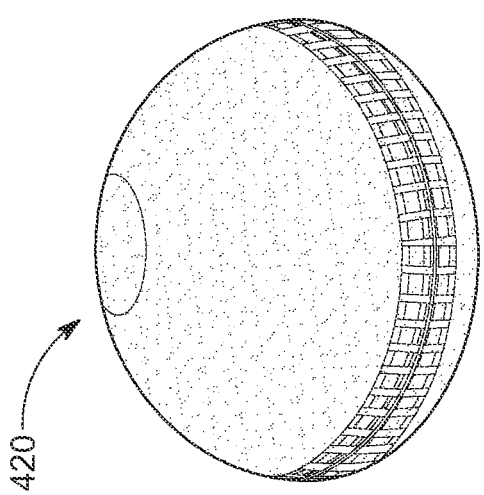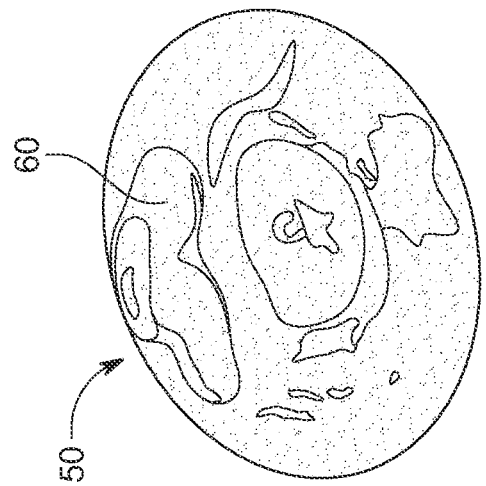
FIG. 32B

SYSTEMS, DEVICES AND METHODS OF MAKING MAMMARY IMPLANTS AND TISSUE EXPANDERS HAVING RIBBED SHELLS

CROSS-REFERENCE TO RELATED APPLICATIONS

The present patent application claims benefit of U.S. Provisional Application Ser. No. 62/717,271, filed Aug. 10, 2018, the disclosure of which is hereby incorporated by reference herein.

BACKGROUND OF THE INVENTION

Field of the Invention

The present patent application is generally related to medical devices, and is more specifically related to implantable prostheses such as mammary implants and tissue expanders.

Description of the Related Art

Implantable prostheses, such as breast implants, are commonly used to replace or augment body tissue. In the case of the female breast, it may become necessary to remove some or all of the mammary gland and surrounding tissue in order to treat breast cancer. This surgery typically leaves a void that may be filled with an implantable prosthesis that supports surrounding tissue and provides a normal body appearance, eliminating much of the shock and depression that often follows breast cancer surgeries. Implantable prostheses are also used for breast augmentation procedures.

Tissue expanders, another form of implantable prostheses, are implantable devices that are placed beneath the skin and then gradually inflated to stretch the overlying tissue. A common breast reconstruction technique is tissue expansion, which involves expansion of the breast skin and muscle using a temporary tissue expander. After implantation, a solution, such as saline, is periodically injected into the tissue expander to increase the volume of the expander. Between injections, the surrounding skin is permitted to stretch and grow to create the increased skin surface. The solution may also be withdrawn from the tissue expander to reduce its volume.

Implantable prostheses and tissue expanders usually include a shell made of silicone or a biocompatible polymer. Such devices are typically manufactured by dipping an appropriately sized and shaped mandrel into silicone. The mandrel may be solid or hollow. In other methodologies, a silicone solution may be sprayed onto the mandrel and allowed to cure. Hollow molds may also be used for forming the shells of implantable prostheses.

When a mandrel is used for making an implant, the process results in the formation of a shell having a mandrel opening, e.g., a circular hole, in one of its faces. After the shell has been formed, it must be removed from the mandrel. The mandrel opening is subsequently covered with a patch that seals the hole to form a fluid impervious implant shell. The completed shell can remain unfilled, be pre-filled, or intraoperatively filled through a small fill port or valve with a solution such as gel, saline, foam, or combinations of these materials.

In some instances, silicone breast implants are not completely filled with solution. This situation may result in the formation of a crater or concavity at the apex of the implant, which is commonly referred to as the ashtray effect. The ashtray effect is generally most evident when the implant is positioned atop a flat surface.

FIG. 1 shows a conventional breast implant 50 having an apex 52 at an upper end thereof, a base 54 at a lower end thereof, a radius 56 that extends around the circumference of the implant, and a dome 58 having a convexly curved surface that extends between the apex 52 and the radius 56. The implant is not completely filled with gel, which results in the occurrence of the ashtray effect (i.e., the presence of craters, depressions, or concavities at the apex). Many efforts have been directed to eliminate the ashtray effect including upside down curing and adding extra gel. Both approaches may increase the cost of an implant or involve expensive tooling. Adding extra gel may add weight to the implant. Moreover, in many instances, upside down curing has not been deemed to efficiently remove the ashtray effect.

Breast implants are generally designed to be relatively soft and pliable, which make breast implants susceptible to rippling or wrinkling. One of the primary clinical complications with breast implants is rippling, which may be discernible through the skin as ripples, of which smaller framed women with larger implants are more susceptible. FIG. 2 shows a breast implant 70 having ripples 72. Avoiding or minimizing the occurrence of ripples has become an issue of enhanced importance with the increase of pre-pec procedures whereby implants are placed above the pectoralis muscle and closer to the skin. In any event, wrinkles and rippling are not desirable and technologies to reduce or eliminate their occurrence are sought without increasing the amount of gel, increasing shell tension, and/or increasing the outer diameter of the implant.

Another problem that occurs with mammary implants is the formation of wrinkles along one or more edges of the implant, which is commonly referred to as scalloping. Referring to FIG. 3, a conventional implant 80 has an upper pole 82 and a lower pole 84. Several creases 86 are shown on the upper pole 82 of the anterior face. The creases 86 (i.e., scalloping) radiate inwardly from the perimeter 88 of the prosthesis. The creases formed in the anterior face can be discerned through the skin of the patient and are not aesthetically desirable.

In many instances it is desirable to create implant devices that maintain or increase the projection of implants without requiring an increase in the amount of gel or the gel/shell ratio. Increasing gel adds additional weight, and increases the tension on the shell.

Referring to FIG. 4, in order to avoid the ashtray effect, rippling, wrinkling, and/or scalloping, and in order to improve the projection of the apex of the shell, some breast implant manufacturers provide breast implants 90 that are more fully filled with gel or saline solution. Many conventional implants contain about 400 cc of gel or saline. In one design, an additional 65 cc of gel or saline is introduced into the shell. The additional gel or saline added to the shell of the implant 90 improves the projection of the apex 92 of the implant. Unfortunately, increasing the volume of gel or saline within the implant 90 adds additional weight to the implant, and increases the tension on the shell.

The fatigue strength of a shell and/or implant is an important characteristic for providing for a long product life. One way to increase fatigue strength is to increase shell thickness, however, this may adversely affect the natural feel of the implant as thinner shells typically feel more natural. There is a continuing need for implant shells having improved fatigue strength while maintaining normal shell thickness and a more natural feel.

The form stability or ability to maintain the shape of the implant is an important consideration. Current means to afford improved form stability are directed toward increasing the cohesiveness of the gel. Increased gel cohesiveness changes the feel of the implant to less soft, while also increasing the risk of gel fracture as there are known incidences of highly cohesive gel implants exhibiting gel fracture.

In view of the above state of the art, there remains a need for mammary implants and tissue expanders that minimize the occurrence of the ashtray effect, rippling, wrinkling, and scalloping, while providing improved projection at the apex of the shell. In addition, there remains a need for systems, devices and methods that minimize the weight of implants. There also remains a need for implants having enhanced structural integrity, improved fatigue strength, and that maintain a soft feel to the touch.

SUMMARY OF THE INVENTION

The systems, devices, and methods disclosed herein are directed to overcoming the above-identified challenges that are confronted when designing and making implantable devices having shells such as mammary implants and tissue expanders.

In one embodiment, implant shells are made by dipping or spraying a mandrel with a biocompatible, curable material such as silicone, polymers, polyurethane, silicone-polyurethane co-polymers, elastomers or combinations thereof. After application of the biocompatible, curable material to the mandrel, the curable material is allowed to cure and the cured shell is removed from the mandrel.

In one embodiment, the mandrel may be made of a variety of materials including metals, metallic alloys, one or more polymers or copolymers, ceramic materials, wood, stone, or any combination thereof. In one embodiment, the mandrel may be made of a metal such as stainless steel. In one embodiment, the mandrel may be made of stainless steel and be coated with a polymer. In one embodiment, the mandrel may be made of polymers. Metals and certain polymers are preferably used for making mandrels because they are amenable to traditional machining techniques yet hold their dimensions at high temperatures.

In one embodiment, grooves having a known geometry are formed on the mandrel. The grooves may be created using well-known techniques including machining, molding, or three-dimensional printing, and hollow molding. The grooves may extend radially between an apex and a base of the mandrel, circumferentially around the sides of the mandrel, obliquely relative to the radial and circumferential directions, or in patterns involving radial, circumferential, and/or oblique directions. The grooves themselves need not be unidirectional and may be multi-directional as in a wave pattern. Those skilled in the art may discern that the grooves may be provided in select or different regions of the shell to affect the shell properties in that region.

In one embodiment, the grooves are amenable to being filled with a biocompatible, curable material used to make implant shells, such as silicone. In one embodiment, the grooves may have concave curved surfaces (rounds and fillets) that minimize the presence of sharp edges on the mandrel. In one embodiment, when a curable material (e.g., silicone) is applied to the mandrel through known methods the grooves create ribs that are integral with the shell.

In one embodiment, the mandrel preferably has an inverse of a shape and topography of a desired mammary implant or tissue expander.

In one embodiment, at least one groove has a geometry that results in the formation of a rib having a cross section to resist bending of the shell wall, yet be amenable to manual release of the shell. As such, the grooves preferably have a depth and a shape that enhances the structural integrity of the ribs while facilitating removal of the shell from the mandrel without damaging (e.g., tearing) the shell.

In one embodiment, the ribs are provided on an inner surface of the shell that does not contact the patient. The ribs preferably act as shell stiffeners to allow the shell to better resist folding onto itself, which minimizes the likelihood of wrinkles or ripples. In one embodiment, ribs may project from the outer surface of the shell. In one embodiment, ribs may project from both the inner surface and the outer surface of the shell.

In one embodiment, a shell has a least one rib. In one embodiment, the at least one rib is a circumferential rib. In one embodiment, the shell preferably includes two or more ribs that are circumferential ribs that are located in the radius region of the shell to increase the hoop stiffness of the shell. In one embodiment, the ribs are radially extending ribs (i.e., ribs that extend from the apex to the base of the shell). In one embodiment, the ribs are oblique ribs (i.e., angled relative to the radial and circumferential directions).

In one embodiment, the ribs resist bending of the shell while not significantly affecting the external compressibility or feel of the implant. A preferred cross-section may provide bending stiffness yet be releasable from the grooves of the mandrel during manufacturing. Preferred cross-sectional rib geometries may include tapered or rounded trapezoidal, rectangular, hemispherical, or triangular shaped ribs.

In one embodiment, the one or more ribs may be provided in at least the radial region of the implant. In one embodiment, the one or more ribs may be provided in the apex and/or dome region of the shell. The one or more ribs may run in the circumferential direction, radial direction, or both radial and circumferential directions.

In one embodiment, an implant preferably includes a shell enclosure having an inside surface, an outside surface, an apex, a radius section, and a dome section located between the apex and the radius section. In one embodiment, the shell is filled with a biocompatible material including but not limited to a gel, a silicone gel, saline, water, air, a biocompatible gas (e.g., nitrogen), or combinations thereof. In one embodiment, the shell has at least one elongated section that has a greater stiffness than the adjacent sections of the shell.

In one embodiment, the at least one elongated section extends from the inside surface of the shell and has a geometry that resembles one or more of the following shapes: rectangular, triangular, tapered or rounded trapezoidal, or hemispherical.

In one embodiment, the at least one elongated section extends circumferentially, radially, and/or at an oblique angle relative to the circumferential or radial directions.

In one embodiment, the at least one elongated section may be continuous or discontinuous.

In one embodiment, the at least one elongated section may be formed from the same material as the shell.

In one embodiment, the at least one elongated section may be formed integral with the shell during shell creation (e.g., spraying, dipping, molding, stenciling, injection molding, 3D printing, etc.).

In one embodiment, the at least one elongated section may be a separate piece that is assembled to the shell (e.g., insert molding, pre-cut sheeting).

In one embodiment, the at least one elongated section may be formed from a different material than that of the adjacent sections (e.g., a different silicone or the same silicone further cross-linked).

In one embodiment, the at least one elongated section may be further cross-linked to the shell as a result of selective strip-line exposure to a radiation source.

In one embodiment, the at least one elongated section may be a composite of a second material that is embedded within the shell wall (e.g., a monofilament or multifilament structure that is either polymeric (e.g., suture material) or metallic (e.g., a thin wire).

In one embodiment, the second material may be embedded during a layering or molding process used to form the shell.

In one embodiment, the embedded second material may include a portion that is adapted to extend outside the shell wall. In one embodiment, the portion that extends outside the shell wall may be in the form of a suturing tab used for fixation or anti-rotation especially for smooth implants.

In one embodiment, the embedded second material may provide surface texture, patterns, and/or barbs that will assist in resisting implant rotation after implantation.

In one embodiment, an implantable prosthesis includes a shell having an apex, a base, a radius located between the apex and the base, and a dome extending between the apex and the radius. In one embodiment, the shell has an outer surface that is smooth and an inner surface that surrounds an interior volume of the shell. In one embodiment, a biocompatible filler material (e.g., gel) is disposed within the interior volume of the shell. In one embodiment, the shell may be filled with 100 cc-1,445 cc of biocompatible filler material. In one embodiment, at least one rib is integrally formed with the shell and projects inwardly from the inner surface of the shell and into the interior volume of the shell.

In one embodiment, the at least one rib includes a plurality of circumferential ribs that project inwardly from the inner surface of the shell. In one embodiment, the circumferential ribs are evenly spaced from one another.

In one embodiment, each circumferential rib has a constant depth relative to the inner surface of the shell. In one embodiment, each circumferential rib has a depth of about 0.015-0.50 inches.

In one embodiment, each circumferential rib may have a variable depth relative to the inner surface of the shell. In one embodiment, the depth of each rib may vary, or some of the ribs may have different depths than other ribs on the shell.

In one embodiment, each circumferential rib has a height associated therewith that increases in size sequentially between the apex and the base of the shell.

In one embodiment, each circumferential rib has height that is constant.

In one embodiment, each circumferential rib has a variable depth relative to the inner surface of the shell that decreases in size sequentially between the apex and the base of the shell.

In one embodiment, the at least one rib integrally formed with the shell includes a mesh shaped rib pattern projecting inwardly from the inner surface of the shell and into the interior volume of the shell. In one embodiment, a mesh shaped rib pattern may include a combination of at least one circumferential rib and at least one radial rib that is orthogonal to the at least one circumferential rib.

In one embodiment, the mesh shaped rib pattern includes an upper circumferential rib projecting from the inner surface of the shell and aligned with the radius of the shell, an intermediate circumferential rib spaced from the upper circumferential rib, projecting from the inner surface of the shell, and aligned with the radius of the shell, and a lower circumferential rib spaced from the intermediate circumferential rib, projecting from the inner surface of the shell, and aligned with the radius of the shell. The intermediate circumferential rib is preferably located between the upper circumferential rib and the lower circumferential rib.

In one embodiment, the mesh shaped rib pattern includes a series of radially extending ribs that are spaced from one another around the radius of the shell and that project from the inner surface of the shell. In one embodiment, each radially extending rib intersects with the upper, intermediate, and lower circumferential ribs to form a lattice structure.

In one embodiment, the mesh shaped rib pattern includes a series of upper islands located between the upper circumferential rib and the intermediate circumferential rib, whereby each upper island is surrounded by the upper circumferential rib, the lower circumferential rib, and two of the radially extending ribs.

In one embodiment, the mesh shaped rib pattern also includes a series of lower islands located between the intermediate circumferential rib and the lower circumferential rib, whereby each lower island is surrounded by the intermediate circumferential rib, the lower circumferential rib, and two of the radially extending ribs.

The rib patterns disclosed in the present patent application preferably improve form stability or the ability of an implant to maintain its shape. The rib patterns disclosed herein preferably increase strength and rigidity without increasing the shell wall thickness, thus maintaining softness while improving form stability. Increasing the coverage and depth of the ribs greatly influence the form stability. Ribs may extend radially between the implant radius and apex, and circumferentially around the sides of the implant.

In one embodiment, the at least one rib integrally formed with the shell includes a star-shaped rib projecting inwardly from the inner surface of the shell. In one embodiment, the star-shaped rib pattern is aligned with the apex of the shell.

In one embodiment, the shell includes a biocompatible polymer material (e.g., silicone, a polymer), and the biocompatible filler material may be gel, silicone gel, saline, foam, air, gas, and combinations thereof.

In one embodiment, a method of making an implantable prosthesis such as a silicone shell may include obtaining a shell having a first major surface and a second major surface, applying at least one rib to the first major surface of the shell so that the at least one rib projects from the first major surface of the shell, and configuring the shell so that the second major surface of the shell defines a convexly curved smooth outer surface of the shell and the first major surface defines a concave inner surface of the shell. The at least one rib desirably projects inwardly from the concave inner surface of the shell and into an interior volume of the shell.

In one embodiment, the obtaining the shell step may include depositing a curable shell forming material over a convexly curved surface of a mandrel and at least partially curing the curable shell forming material to form the shell. In one embodiment, during the depositing step the second major surface of the shell is in contact with the convexly curved surface of the mandrel and the first major surface of the shell faces away from the convexly curved surface of the mandrel.

In one embodiment, the applying step may include juxtaposing the mandrel with a mold having a concave recess including one or more grooves formed in the concave recess so that the first major surface of the shell opposes the one or more grooves. In one embodiment, the applying step may include introducing a curable rib forming material into the one or more grooves of the mold and aligning the convexly curved surface of the mandrel with the concave recess so that the curable rib forming material contacts the first major surface of the shell.

In one embodiment, the configuring the shell step desirably includes, after the applying step, removing the shell from the mandrel and inverting the shell so that the second major surface of the shell defines a smooth outer surface of the shell and the first major surface of the shell defines an inner surface of the shell having the at least one rib projecting inwardly from the inner surface of the shell.

In one embodiment, a mandrel for making a prosthesis implant shell includes an apex defining an upper end of the mandrel, a base defining a lower end of the mandrel, a radius that is located between the apex and the base and that defines a side region of the mandrel, and a dome located between the apex and the radius. In one embodiment, the mandrel has a convexly curved outer surface that extends from the apex to the base of the mandrel. In one embodiment, the mandrel includes at least one groove formed in the convexly curved outer surface of the mandrel.

In one embodiment, the at least one groove preferably includes a plurality of circumferential grooves formed in the convexly curved outer surface of the mandrel. In one embodiment, the circumferential grooves are evenly spaced from one another between the apex and the base of the mandrel.

In one embodiment, each circumferential groove has a constant depth relative to the convexly curved outer surface of the mandrel. In one embodiment, the constant depth of each circumferential groove is about 0.015-0.50 inches.

In one embodiment, each circumferential groove in the mandrel has a height associated therewith that increases in size sequentially between the apex and the base of the mandrel.

In one embodiment, each circumferential groove of the mandrel has height that is constant.

In one embodiment, each circumferential groove of the mandrel has a different depth relative to the convexly curved outer surface of the mandrel that decreases in size sequentially between the apex and the base of the mandrel.

In one embodiment, the at least one groove comprises a mesh shaped groove pattern formed in the convexly curved outer surface of the mandrel.

In one embodiment, the mesh shaped groove pattern in the mandrel may include an upper circumferential groove formed in the convexly curved outer surface of the mandrel and aligned with the radius of the mandrel, an intermediate circumferential groove spaced from the upper circumferential groove, formed in the convexly curved outer surface of the mandrel, and aligned with the radius of the mandrel, and a lower circumferential groove spaced from the intermediate circumferential groove, formed in the convexly curved outer surfaced of the mandrel, and aligned with the radius of the mandrel. The intermediate circumferential groove may be located between the upper circumferential groove and the lower circumferential groove.

In one embodiment, the mandrel has a series of radially extending grooves that are spaced from one another around the radius of the mandrel and that are formed in the convexly curved outer surface of the mandrel. In one embodiment, each radially extending groove intersects with the upper, intermediate, and lower circumferential grooves to form a lattice structure.

In one embodiment, the mesh shaped groove pattern of the mandrel may include a series of upper islands located between the upper circumferential groove and the intermediate circumferential groove and formed in the convexly curved outer surface of the mandrel, whereby each of the upper islands is bounded by two of the radially extending grooves.

In one embodiment, the mesh shaped groove pattern preferably includes a series of lower islands located between the intermediate circumferential rib and the lower circumferential rib and formed in the convexly curved outer surface of the mandrel, whereby each of the lower islands is bounded by two of the radially extending grooves.

In one embodiment, a mandrel for making a ribbed shell for use as a mammary implant or tissue expander preferably includes an apex at an upper end of the mandrel, a base at a lower end of the mandrel, a radius that extends around the circumference of the mandrel, and a dome having a convexly curved shape that extends between the apex and the base. In one embodiment, the mandrel desirably has a convexly curved outer surface that extends between the apex and the base.

In one embodiment, a plurality of spaced grooves is formed in the outer surface of the mandrel. In one embodiment, the grooves extend around the circumference of the mandrel. In one embodiment, the grooves are evenly spaced from one another (e.g., 0.115 inches) between the apex and the base of the mandrel. In one embodiment, the grooves may be formed by removing material from the outer surface of the mandrel. In one embodiment, the grooves may be formed by adding material to the outer surface of the mandrel, such as by using three dimensional printing techniques.

In one embodiment, each of the grooves has a constant depth. In one embodiment, the constant depth of the grooves may be between about 0.025-0.050 inches. In other embodiments, the constant depth grooves may have a depth that is less than 0.025 inches or greater than 0.050 inches. In one embodiment, each of the respective grooves has a constant depth, but a different height. The heights of the respective grooves preferably increase sequentially between the apex and the base of the mandrel.

In one embodiment, a mandrel utilized for making shells for mammary implants and tissue expanders preferably has circumferential grooves that are evenly spaced from one another, whereby each of the grooves has a constant height but a different depth. In one embodiment, the depths of the circumferential grooves become shallower or decrease sequentially between the apex and the base of the mandrel. For example, a groove closer to the apex has a greater depth than a groove further away from the apex. In one embodiment, each of the circumferential grooves has a height of about 0.025 inches. In one embodiment, the circumferential grooves are evenly spaced from one another by a distance of about 0.150 inches.

In one embodiment, a mandrel for making shells used for mammary implants and tissue expanders preferably includes a mesh shaped groove pattern formed in the outer surface of the mandrel. The mesh shaped groove pattern may be formed by removing material from the mandrel, adding material to the outer surface of the mandrel (e.g., 3D printing), or using a mold to form the mandrel. In one embodiment, the mesh shaped groove pattern preferably extends around the circumference of the mandrel (i.e., in the region of the radius of the mandrel).

In one embodiment, the mesh shaped groove pattern preferably includes an upper circumferential groove that extends around the circumference of the mandrel, an intermediate circumferential groove that extends around the circumference of the mandrel, and a lower circumferential groove that extends around the circumference of the mandrel. In one embodiment, the intermediate circumferential groove is preferably located between the upper circumferential groove and the lower circumferential groove. In one embodiment, the circumferential grooves may lie in respective planes that are parallel with one another. In one embodiment, the circumferential grooves desirably define bands that extend around the circumference of the mandrel. The bands may extend completely or partially around the circumference of the mandrel.

In one embodiment, the mesh shaped groove pattern preferably includes radial grooves that extend from the upper circumferential groove, through the intermediate circumferential groove, and to the lower circumferential groove. The radial grooves preferably extend in a radial direction that runs from the apex to the base of the mandrel. In one embodiment, the radial grooves may be vertical grooves that are evenly spaced from one another around the circumference of the mandrel. The radial grooves preferably intersect the circumferential grooves and cooperatively divide the mesh shaped groove pattern into upper islands located above the intermediate circumferential groove and lower islands located below the intermediate circumferential groove. The respective upper and lower islands preferably extend around the circumference of the mandrel. The upper and lower islands may extend partially or completely around the circumference of the mandrel. In one embodiment, the radial grooves are spaced from one another. In one embodiment, the radial grooves are spaced from one another by a distance of about 0.010-0.50 inches. In one embodiment, the radial grooves are spaced from one another by a distance of about 0.10-0.25 and more preferably about 0.17 inches.

In one embodiment, the grooves preferably have rounded or concave surfaces to avoid the presence of sharp edges, which will facilitate the removal of cured shells from the mandrel without damaging (e.g., tearing) the shells.

In one embodiment, a mandrel utilized to make a shell for a mammary implant or tissue expander preferably includes a star-shaped groove pattern formed in an apex of the mandrel. In one embodiment, the star-shaped groove pattern preferably has a center and six radially extending grooves that extend outwardly from the center. In one embodiment, a circular groove is preferably formed in the outer surface of the mandrel and surrounds the outer ends of the radially extending grooves of the star-shaped groove pattern. In one embodiment, the circular groove has a height of about 0.010-0.050 inches and more preferably about 0.025 inches, and a depth of about 0.010-0.50 inches and more preferably about 0.070 inches, which is measured from the convexly curved outer surface of the mandrel.

In one embodiment, the grooved mandrels disclosed herein are used for making shells having ribs that project inwardly from the inner walls of the shells. The mandrels may be dipped in a solution containing shell forming material, or the shell forming material may be sprayed onto the mandrels whereupon the material preferably flows into the grooves. The ribs that are formed on the shells preferably have a size, shape, orientation, and dimension that mirror the size, shape, orientation, and dimension of the grooves.

In one embodiment, any of the shells disclosed herein may also include at least one external rib that projects from an external surface of a shell. Thus, a shell may have at least one internally projecting rib and at least one externally projecting rib. When a shell is implanted in tissue, the at least one external rib preferably holds the shell in place within the tissue. In one embodiment, the at least one external rib may be a circumferential rib, a radial rib, or a rib angled between the circumferential and radial configurations. In one embodiment, the at least one external rib may include a plurality of externally projecting ribs that are spaced from one another.

In one embodiment, a three-dimensional mold may be used for stamping a layer of viscous silicone to provide structural features (e.g., ribs) on an implant shell. In one embodiment, the mandrel has a concave recess having one or more grooves formed in a concave surface thereof. In one embodiment, an implant shell is pre-formed on a mandrel (i.e., a shell precursor), whereupon the pre-formed shell has smooth outer and inner surfaces. The mandrel and pre-formed shell combination is preferably dipped into an uncured silicone gel to apply a flowable silicone gel material over the exposed surface of the pre-formed shell. In one embodiment, the mandrel may be inserted into the three-dimensional mold whereupon the flowable silicone gel extrudes into the grooves of the three-dimensional mold to form ribs made of uncured silicone gel that are adhered to the exposed surface of the shell. The mold and mandrel assembly may be placed into an oven to apply heat to the shell for curing the ribs adhered to the pre-formed shell, whereby the ribs are integrally secured to the exposed surface of the pre-formed shell. After curing the ribs, the mold and the mandrel may be removed from the oven and the shell detached from the mandrel. In one embodiment, a room temperature vulcanizing silicone (RTV) may be used, which may eliminate the need for oven curing. After the shell is removed from the mandrel, the shell may be inverted so that the ribs secured to the shell project inwardly from the inner surface of the shell and are located on the inside of the shell. After inversion, the outer surface of the shell is preferably smooth and the inner surface of the shell preferably has the ribs that are integral with the shell and that project inwardly from the inner surface of the shell.

In one embodiment, rather than using a three-dimensional stamping of a viscous fluid to form integral ribs on a shell, a silicone sheet or a semi-cured silicone sheet may be used to form the ribs on a pre-formed shell or a shell precursor. The silicone sheet or the semi-cured silicone sheet may be placed on either a male surface with ribs or a female surface with grooves and be compressed between two opposing surfaces for forming the ribs for the shell.

In one embodiment, an injection mold may include a female mold having a smooth concave surface and a male mold including a mandrel having a grooved convex surface that opposes the smooth concave surface of the female mold. In one embodiment, an injection molding process preferably includes injecting an uncured fluid material (e.g., uncured silicone) under pressure into the injection mold. The uncured fluid material is preferably forced into the grooves on the grooved convex surface of the mandrel to form ribs. Additional uncured fluid material preferably flows between the convex surface of the mandrel and the smooth concave surface of the female mold to form a shell having a wall thickness with integral ribs projecting inwardly from an inner surface of the shell. In one embodiment, after the ribs and the shell having been formed by injection molding, the mandrel and the shell/rib structure may be fully cured and removed from the mold. Additional layers of shell formed material may be deposited onto a smooth outer surface of the shell by spraying and/or dipping. Applying additional layers will desirably increase the wall thickness of the shell. Different layers may have different materials incorporated therein. The curable material is preferably fully cured to provide a cured implant shell having ribs integral with the shell, whereby the ribs are secured to an inner surface of the shell and project inwardly.

In one embodiment, an injection mold preferably includes a male mold part including a convex mandrel having a smooth surface and a female mold part including a concave surface having grooves. In one embodiment, prior to inserting the mandrel into the injection mold, an implant shell may be formed on the smooth convex surface of the mandrel. In one embodiment, with the mandrel opposing the grooved concave surface of the female mold, a rib forming material (e.g., uncured silicone) is injected under pressure in liquid form whereupon it flows into the grooves of the grooved concave surface of the female mold for forming ribs. In one embodiment, after the ribs have been injection molded onto a shell, the shell and ribs are cured so that the ribs are integral with the shell. In one embodiment, the cured shell and rib assembly is removed from the mandrel and the shell is inverted so that the ribs are disposed inside the shell and project inwardly from an inner surface of the shell.

In one embodiment, a flat stencil may be used as a two dimensional compression mold for forming one or more ribs on an implant shell. In one embodiment, the implant shell may be fully or partially cured. The shell may be inverted and applied (e.g., stretched) over a disk or plate so that the shell overlies a top surface of the disk/plate with an inner surface of the shell exposed. The disk/plate may have a top surface that is flat or curved.

In one embodiment, a stencil having grooves may be applied over the exposed inner surface of the shell for forming ribs on the shell. The stencil may be made of metal, metal with a lubricious coating, or made of a polymer such as TEFLON. In one embodiment, the stencil may be rigid or flexible.

In one embodiment, a curable rib forming material may be applied to the grooves of the stencil, whereby the curable rib forming material is not under pressure. In one embodiment, the curable rib forming material may be sprayed into the grooves of the stencil. In one embodiment, the curable rib forming material may be poured into the grooves of the stencil. In one embodiment, heat may be applied to cure the rib forming material to provide an implant shell having integral ribs projecting from the exposed inner surface. After curing, the shell may be inverted so that the ribs are located on the inside of shell and project inwardly from the inner surface of the shell wall.

In one embodiment, ribs may be formed on an implant shell using compression molding. In one embodiment, a compression mold preferably includes a female mold part having a concave surface with grooves and a male mold part including a mandrel having a smooth convex surface. In one embodiment, a rib forming material in fluid form (e.g., fluid silicone) is introduced into the mold. In one embodiment, the curable rib forming material that is introduced into the mold is not under pressure. In one embodiment, pressure may be applied by the two opposing mold parts for forming ribs integral with the shell. The shell and the ribs are preferably cured such as by using heat. The shell may be removed from the mandrel and inverted so that the ribs are inside the shell and project inwardly from an inner surface of a shell wall.

In one embodiment, a compression mold preferably includes a female mold part having a smooth concave surface and a male mold part including a mandrel having a grooved convex surface. In one embodiment, a curable material in fluid form is introduced into the mold. The curable material is not under pressure. In one embodiment, pressure may be applied by the two opposing mold parts for forming ribs integral with the shell. The shell and the ribs are preferably cured such as by using heat. After the ribs have been formed, a shell precursor may overlie the mandrel. The mandrel may be removed from the mold for applying additional layers of curable shell forming material over the shell precursor. The additional layers may be applied using spraying and/or dipping techniques. The shell may be removed from the mandrel to provide an implant shell having a smooth outer surface and an inner surface having ribs that project inwardly.

In one embodiment, a compression molding process forms ribs on a shell by positioning a sheet of rib forming material (e.g., a partially cured or fully cured silicone sheet) between two mold halves. In one embodiment, a compression mold preferably includes a female mold part having a concave surface with grooves and a male mold part including a mandrel having a smooth convex surface. In one embodiment, a fully cured or partially cured shell is provided on the mandrel. The sheeting to form the ribs is placed between the shell on the mandrel and the grooved concave surface of the female mold part. Pressure may be applied by the two opposing mold parts to compress the sheeting to form ribs that are integrally connected with the shell. The shell and the ribs may be cured using heat and pressure. The shell may be removed from the mandrel and inverted so that the ribs are located inside the shell and project inwardly from an inner surface of the shell.

In one embodiment, ribs may be formed on a shell using stamps, stencils, and embossing tools. In one embodiment, a shell is premade using any known means. The shell may be fully or partially cured. In one embodiment, the shell is inverted and applied over disk so that an inner surface of the shell is exposed over the top surface of the disk. The shell may be stretched for being applied over the disk. The shell may be secured over a peripheral edge of the disk for holding the shell in the stretched configuration. In one embodiment, the top surface of the disk may be flat or have some curvature.

In one embodiment, an intervening sheet layer of rib forming material may be applied over the exposed inner surface of shell that is stretched over the disk. The intervening sheet layer may be uncured or partially cured. The intervening sheet layer may include a removable barrier layer to facilitate assembly with the exposed inner surface of the shell. The intervening sheet layer may have one or more layers that define the thickness of the sheet layer. The intervening layer, such as a release liner, may be applied between stencil and the sheet material to facilitate ease of separation and removal of the stencil from the sheet material.

In one embodiment, a stencil with grooves is applied over the intervening sheet layer for cutting ribs in the sheet layer. The stencil may be flat. In one embodiment, the stencil may be curved to facilitate flow of material into stencil grooves when flattened under pressure. In one embodiment, the stencil may be pliable or rigid. The stencil is preferably able to withstand pressure without distortion. The stencil may be made of metal. In one embodiment, the stencil may be made of metal with a lubricious coating. In one embodiment, the stencil may be made of a polymer material such as TEFLON®.

In one embodiment, the stencil grooves may include through grooves and/or blind grooves. In one embodiment, the stencil grooves may have chamfers on the sheet contact side of the stencil to facilitate the flow of the sheet material into the stencil grooves when the sheet material is under pressure.

In one embodiment, heat, pressure and/or time may be applied to the sheet and the shell to force the sheet material into the stencil grooves for forming the ribs on the exposed surface of the shell.

In one embodiment, an embossing roller may be used for embossing a rib pattern onto a shell. In one embodiment, a shell may be fully or partially cured. The shell may be applied (e.g., stretched) over a disk (e.g., a flat plate, a curved plate) so that the shell overlies a top surface of the disk with an inner surface of the shell exposed.

In one embodiment, an intervening sheet layer may be applied over the exposed inner surface of the shell. The sheet layer may include one or more layers. The sheet layer may be uncured or partially cured, and may have a removable barrier layer to facilitate assembly with the shell.

In one embodiment, an embossing roller (e.g., a cylindrical roller, a rolling pin) with grooves or a pattern may be rolled over the sheet layer to apply pressure to the sheet layer to improve and/or form a rib pattern on the sheet layer. In one embodiment, heat may be applied to the sheet material to force the sheet material into stencil grooves.

In one embodiment, three-dimensional (3D) printing equipment may be used for forming one or more ribs on an implant shell. In one embodiment, the implant shell may be fully or partially cured. The shell may be applied (e.g., stretched) over a disk so that the shell overlies a top surface of the disk with an inner surface of the shell exposed. The disk may be flat or slightly curved with the shell conforming to the shape of the disk. The 3D printer may be used to form one of more ribs that are integrally secured to the exposed inner surface of the shell. The shell and the ribs may be cured. The shell may be removed from the disk and inverted so that the 3D printed ribs are located inside the shell and project inwardly from the inner surface of the shell.

In one embodiment, a pre-cut rib pattern may be adhered to an exposed inner surface of an implant shell. The pre-cut rib pattern may be formed using conventional methodologies such as stamping, laser cutting, etc. In one embodiment, the pre-cut rib pattern may include a combination of a sheeting and a release liner, which are cut together to form a rib pattern in the sheeting.

In one embodiment, an implant shell may be fully or partially cured. The shell may be inverted and applied (e.g., stretched) over a disk so that the shell overlies a top surface of the disk with an inner surface of the shell exposed. The top surface of the disk may be flat or slightly curved with the shell conforming to the shape of the top surface of the disk.

In one embodiment, the release liner may be removed to expose a surface of the cut sheet that contains the rib pattern, and the exposed surface of the rib pattern is laid over the exposed inner surface of the implant shell. Heat is preferably applied to secure the ribs to the exposed inner surface of the implant shell.

In one embodiment, the rib pattern laid over the exposed inner surface of the implant shell may be made from molding, by cutting the rib pattern from a sheet, from 3D printing, extrusion, and/or any known methodology to form and apply a desired rib pattern to the inside surface of an implant shell.

In one embodiment, the rib pattern is applied over the exposed inner surface of the shell that is stretched out. In one embodiment, heat may be applied to the implant shell and the rib pattern to vulcanize the components together. In one embodiment, pressure may be used for joining the rib pattern and the shell together. In one embodiment, pressure is not required for joining the rib pattern and the shell together.

In one embodiment, the pre-cut rib pattern may be laid over the exposed inner surface of the shell in 3D form (e.g., an inverted shell over a mandrel). In one embodiment, the pre-cut rib pattern may be laid over the exposed inner surface of the shell in 2D form (e.g., stretching the shell over a flat or slightly curved disk). In one embodiment, the pre-cut rib pattern may be dyed a different color to facilitate inspection of the implant shell to confirm that all of the components are intact (e.g., that the rib pattern is properly aligned with and secured over the inner surface of the implant shell).

In one embodiment, the releasable backing liner preferably keeps the pre-cut rib pattern in proper alignment during transportation to the shell. In one embodiment, the inner surface of the shell may be applied to a pre-cut rib pattern to minimize travel of the pre-cut rib pattern with the shell stretched over a flat disk. In one embodiment, the rib pattern is continuous and has one integral pattern, which may be termed a snowflake pattern.

The rib pattern preferably includes the actual ribs that are attached to the inner surface of the implant shell, and not the grooves that are used to create the ribs. The "backing sheet" may be temporary (e.g., a removable polymer film that is removed and discarded), or permanent (e.g., a thin silicone layer substrate), whereby the permanent layer serves as a thin bonding layer that enables the ribs to be bonded directly to the inner surface of the shell.

These and other preferred embodiments of the systems, devices and methods disclosed herein will be described in more detail below.

BRIEF DESCRIPTION OF THE DRAWINGS

FIG. 9 shows a schematic view of a portion of the mandrel shown in FIGS. 8A and 8B.

FIG. 32A shows a side view of a series of implants including a conventional implant, an implant having a shell with a mesh shaped rib pattern, and an implant having a shell filled with an increased volume of gel.

FIG. 32B shows a perspective view of the implants shown in FIG. 32A.

FIG. 45B-1 is a cross-sectional view of the shell molding system of FIG. 45B.

DETAILED DESCRIPTION OF PREFERRED EMBODIMENTS

In one embodiment, the elements of the mammary implants and/or tissue expanders disclosed herein may be defined as set forth below.

Device. A mammary implant or tissue expander, which is filled with gel or saline. A device may be pre-filled, filled intraoperatively, or may be filled in situ. Breast implants are typically pre-filled. Tissue expanders are typically filled in situ.

Shell. The outer envelope of the device, which contains the gel or saline. The shell is typically made of biocompatible polymers such as silicone, however, other materials may be used.

Shell precursor. A shell subassembly from which a fully formed implantable shell is derived. A shell precursor may have a wall thickness that is thinner than the wall thickness of a shell and one or more layers of a shell forming material may be added to the shell precursor to form a shell.

Ribs. Male protrusions provided on the shell, which are integral with the shell. The ribs may be internal ribs projecting from the inner, non patient contacting surface of the shell. The ribs may be external ribs that project from the outer surface of the shell. A device may have a single rib or multiple ribs referred to herein as ribs.

Radius. The side region of the device where the dome of the shell comes down to intersect with the base of the shell.

Dome. The rounded region of the shell running from the apex to the radius region.

Apex. The top of the dome of the shell.

Integral. Manufactured in such a way such that one piece is created (e.g., the ribs are integral with the shell).

Radial direction. Running in general direction from the apex to the base of the shell and/or running in a plane that is perpendicular to the base.

Circumferential direction. A direction that extends around the sides of an implant and/or in a plane that is parallel with the base, such as the radius region of a mammary implant or tissue expander.

Figure 5A:
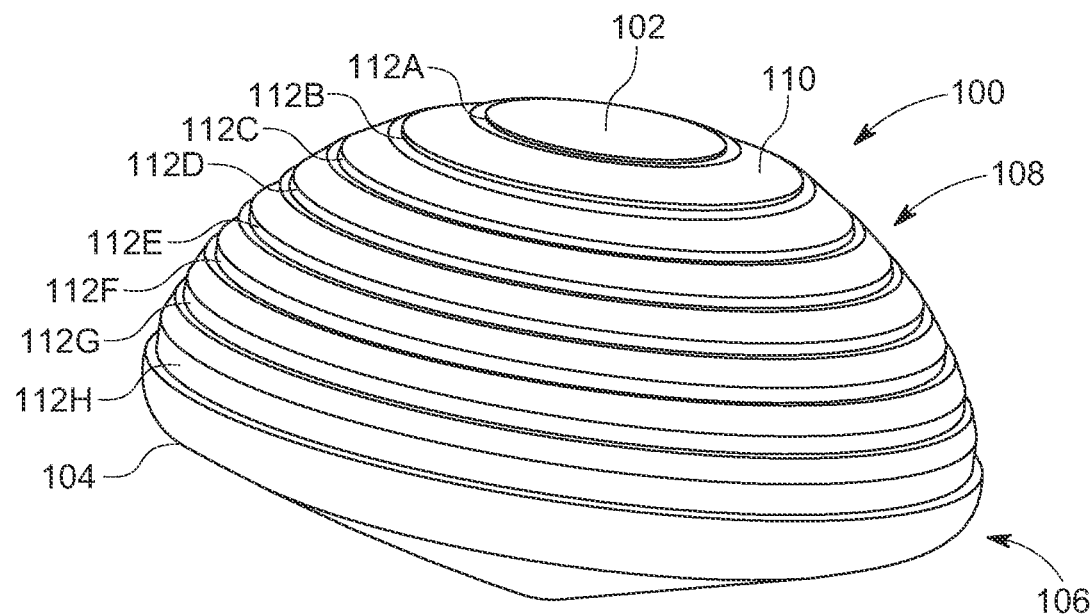
FIG. 5A shows a perspective view of a mandrel having constant depth grooves formed in an outer surface thereof, in accordance with one embodiment of the present patent application.
Figure 5B:
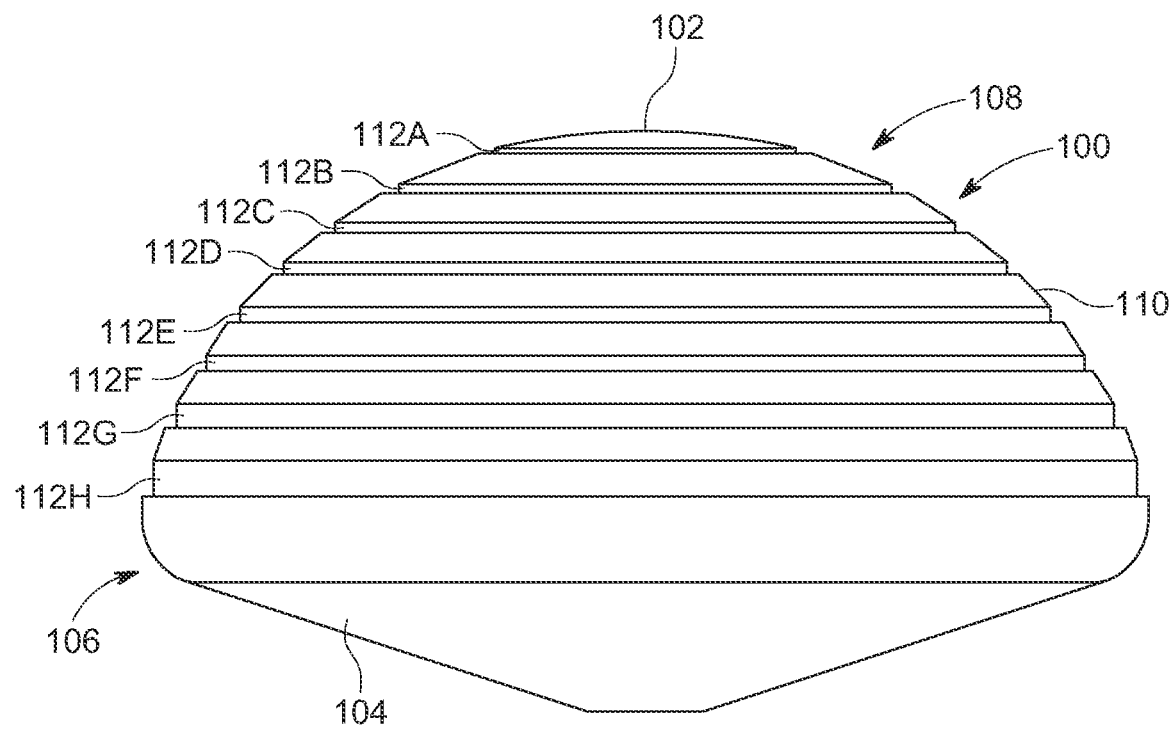
FIG. 5B shows a front elevation view of the mandrel shown in FIG. 5A.

Referring to FIGS. 5A and 5B, in one embodiment, a mandrel 100 for making a ribbed shell for use as a mammary implant or tissue expander preferably includes an apex 102 at an upper end of the mandrel, a base 104 at a lower end of the mandrel, a radius 106 that extends around the circumference of the mandrel 100, and a dome 108 having a convexly curved shape that extends between the apex 102 and the base 104. The mandrel 100 has a convexly curved outer surface 110 that extends between the apex 102 and the base 104.

In one embodiment, a plurality of spaced grooves 112A-112H is formed in the outer surface 110 of the mandrel 100. In one embodiment, the grooves 112A-112H extends around the circumference of the mandrel. In one embodiment, the grooves 112A-112H are evenly spaced from one another between the apex 102 and the base 104 of the mandrel. In one embodiment, the grooves 112A-112H may be formed by removing material from the outer surface 110 of the mandrel 100. In one embodiment, the grooves 112A-112H may be formed by adding material to the outer surface of the mandrel, such as by using 3D printing techniques.

Figure 6:
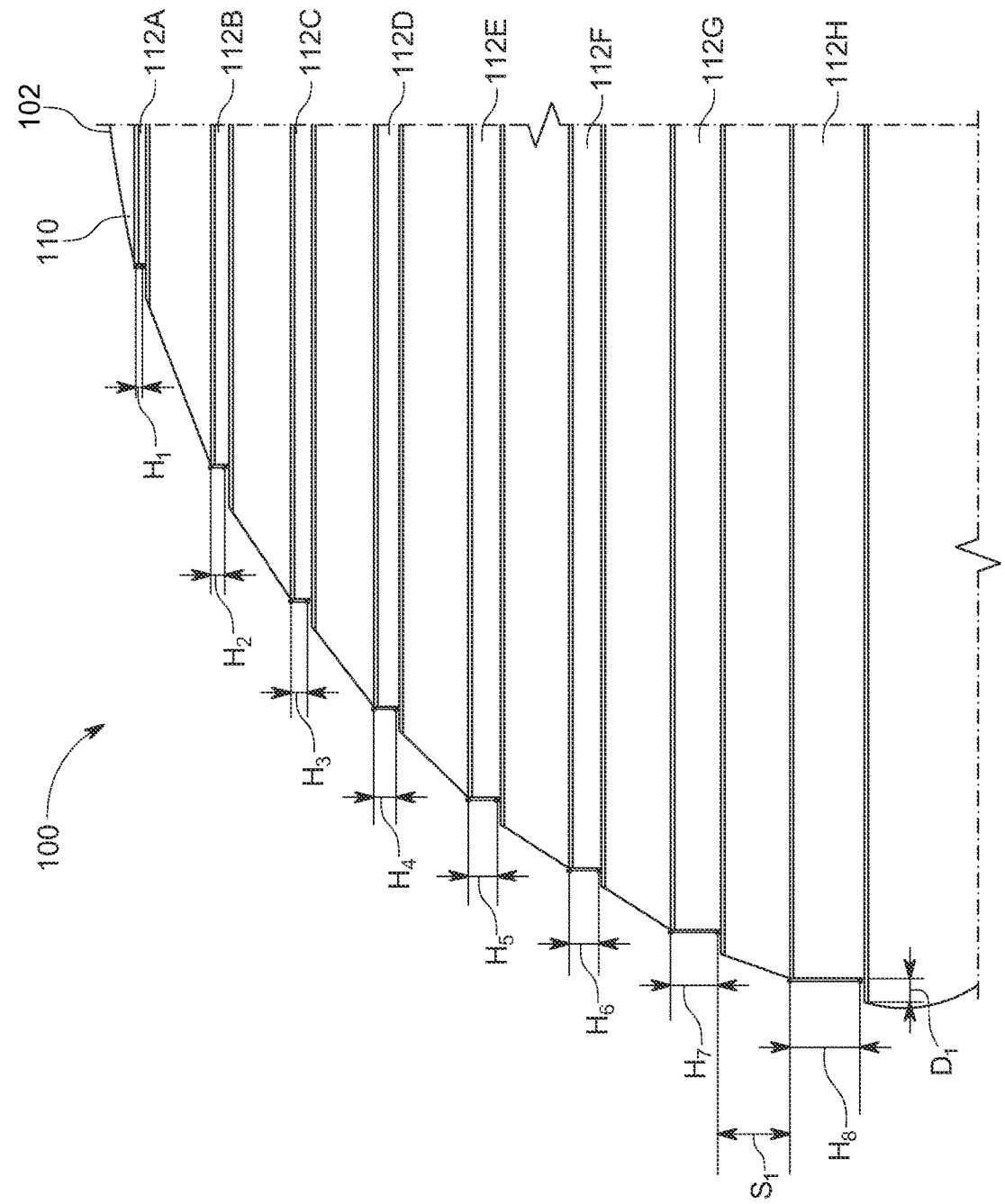
FIG. 6 shows a schematic view of a portion of the mandrel shown in FIGS. 5A and 5B.

Referring to FIG. 6, in one embodiment, the grooves 112A-112H shown in FIGS. 5A and 5B are formed in the outer surface 110 of the mandrel 100. In one embodiment, each of the grooves 112A-112H has a constant depth. In one embodiment, the constant depth $D_1$ of the grooves 112A-112H is about 0.050 inches. In other embodiments, the grooves may have a depth that is less than 0.050 inches or greater than 0.050 inches. In one embodiment, each of the grooves 112A-112H are evenly spaced from one another between the apex 102 and the base 104 by a distance $S_1$ of about 0.150 inches. For example, in one embodiment, the distance between an upper end of a seventh groove 112H and a lower end of a sixth groove 112G is the distance designated $S_1$, which is about 0.150 inches.

In one embodiment, each of the respective grooves 112A-112H has a constant depth, but a different height. In one embodiment, the heights of the respective grooves 112A-112H increase sequentially between the first groove 112A adjacent the apex 102 and the seventh groove 112H adjacent the base 102. For example, in one embodiment, the second groove 112B has a height $H_2$ that is greater than the height $H_1$ of the first groove 112A, the third groove has a height $H_3$ that is greater than the height $H_2$ of the second groove 112B, the fourth groove 112D has a height $H_4$ that is greater than the height $H_3$ of the third groove 112C, etc. In one embodiment, the first groove 112A has a height $H_1$ of about 0.009 inches, the second groove 112B has a height $H_2$ of about 0.027 inches, the third groove 112C has a height $H_3$ of about 0.037 inches, and the fourth groove 112D has a height $H_4$ of about 0.051 inches. In addition, in one embodiment, the fifth groove 112E has a height $H_5$ of about 0.069 inches, the sixth groove 112F has a height $H_6$ of about 0.073 inches, the seventh groove 112G has a height $H_7$ of about 0.107 inches, and the eighth groove 112H has a height $H_8$ of about 0.163 inches. In one embodiment, a mandrel may have less than seven grooves or more than seven grooves. In one embodiment, the grooves may extend circumferentially around the radius 106 (FIG. 5B) of the mandrel, radially between the apex and the base of the mandrel, or at an angle or slope relative to the circumferential configuration and the radial configuration.

In one embodiment, the mandrel 100 shown and described above in FIGS. 5A-5B and 6 may be utilized for forming a shell (e.g., a silicone shell) that is utilized for a mammary implant or a tissue expander. In one embodiment, the shell may be formed by dipping the mandrel 100 in a curable solution, such as curable silicone, whereupon the silicone fills the grooves 112A-112H and coats the outer surface 110 of the mandrel. In one embodiment, the shell may be formed by spraying silicone onto the outer surface 110 of the mandrel 100, whereby the silicone fills the grooves 112A-112H formed on the outer surface 110 of the mandrel 100 and coats the outer surface 110. In one embodiment, a shell having inwardly extending ribs may be formed using a hollow mold.

Figure 7A:
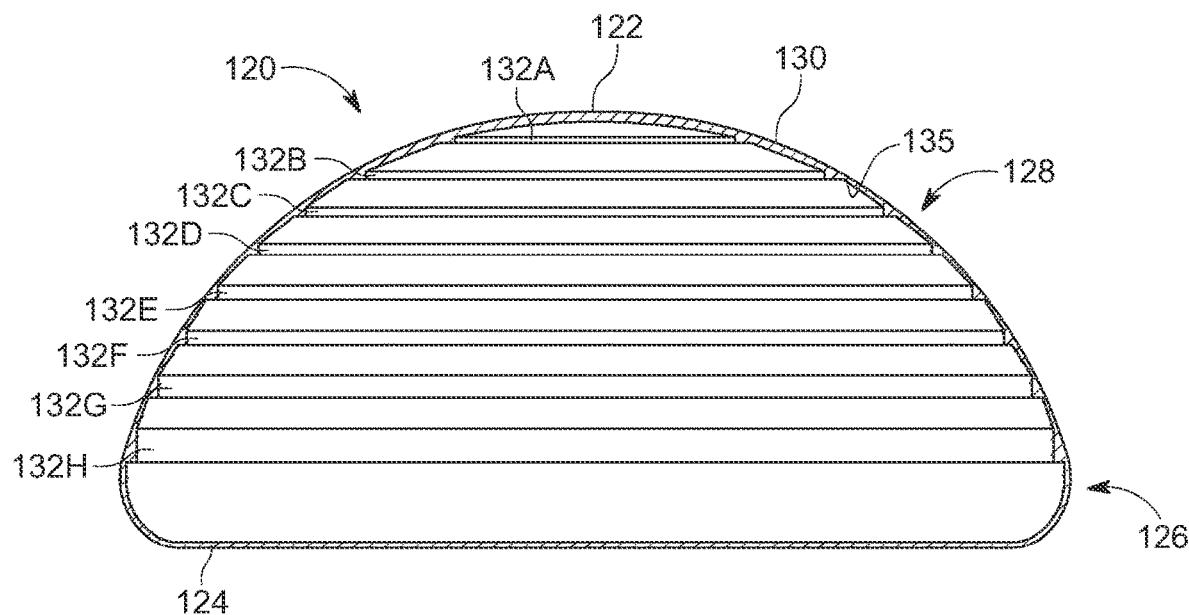
FIG. 7A shows a cross-sectional view of a shell that is made using the mandrel shown in FIGS. 5A-5B and 6, in accordance with one embodiment of the present patent application.
Figure 7B:
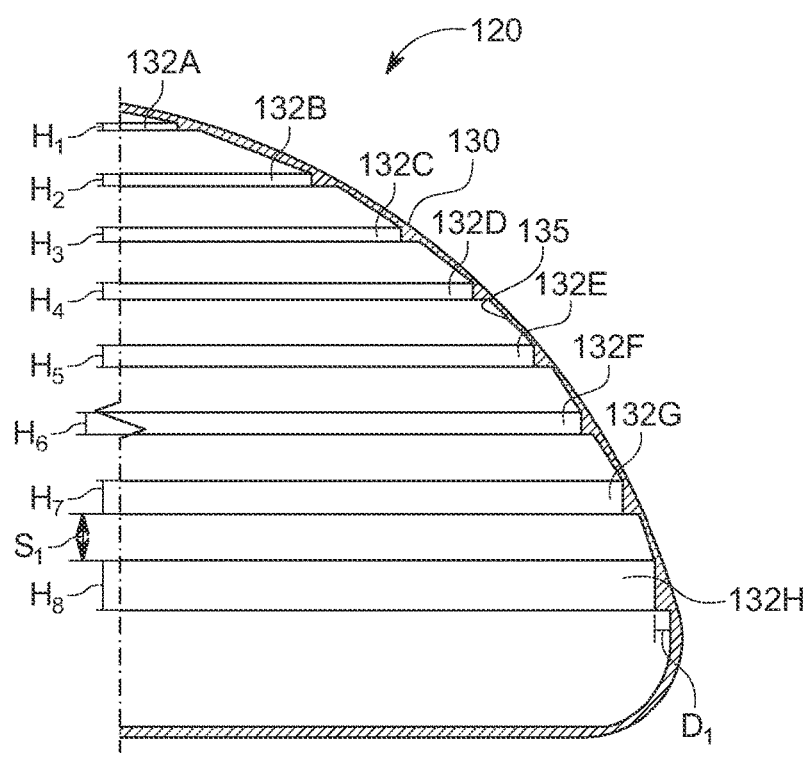
FIG. 7B shows a partial cross-sectional view of the shell of FIG. 7A.

Referring to FIGS. 7A and 7B, in one embodiment, a shell 120 may be formed on the outer surface 110 of the mandrel 100 shown and described above in FIGS. 5A-5B and 6. In one embodiment, the shell 120 preferably includes an apex 122, a base 124, a radius 126 that extends around the circumference or side of the shell 120, and a dome 128 that extends from the apex 122 to the radius 126 of the shell.

In one embodiment, the shell has a convexly curved outer surface 130 and a concavely curved inner surface 135 that surrounds an interior volume of the shell 120. In one embodiment, the interior volume of the shell 120 is preferably filled with a gel or saline solution. The shell 120 desirably includes ribs 132A-132H that project inwardly from the inner surface 135 of the shell 120. In one embodiment, the ribs are desirably mirror images of the grooves 112A-112H provided on the mandrel shown and described above in FIGS. 5A-5B and 6. The ribs 132A-132H preferably have dimensions that match the dimensions of the grooves 112A-112H provided on the mandrel. In one embodiment, the inwardly projecting ribs preferably include a first rib 132A having a height $H_1$ of about 0.009 inches, a second rib 132B having a height $H_2$ of about 0.027 inches, a third rib 132C having a height $H_3$ of about 0.036 inches, and a fourth rib 132D having a height $H_4$ of about 0.051 inches. The shell 120 preferably includes a fifth rib 132E having a height $H_5$ of about 0.069 inches, a sixth rib 132F having a height $H_6$ of about 0.073 inches, a seventh rib 132G having a height $H_7$ of about 0.107 inches, and an eighth rib 132H having a height $H_8$ of about 0.163 inches.

In one embodiment, each of the ribs 132A-132H projects inwardly from the inner surface 135 of the shell 120. In one embodiment, each rib projects inwardly a depth $D_1$ of about 0.050 inches. In one embodiment, the spacing between each of the ribs 132A-132H may be constant. In one embodiment, the spacing $S_1$ between each of the ribs 132A-132H may be about 0.150 inches. In one embodiment, the shell 120 may be filled with a filling material such as a gel, saline, a gas, or a combination of two or more of the above-listed filler materials. In one embodiment, the shell may include a patch secured over a mandrel opening, which is typically located at a posterior face of the shell.

Figure 8A:
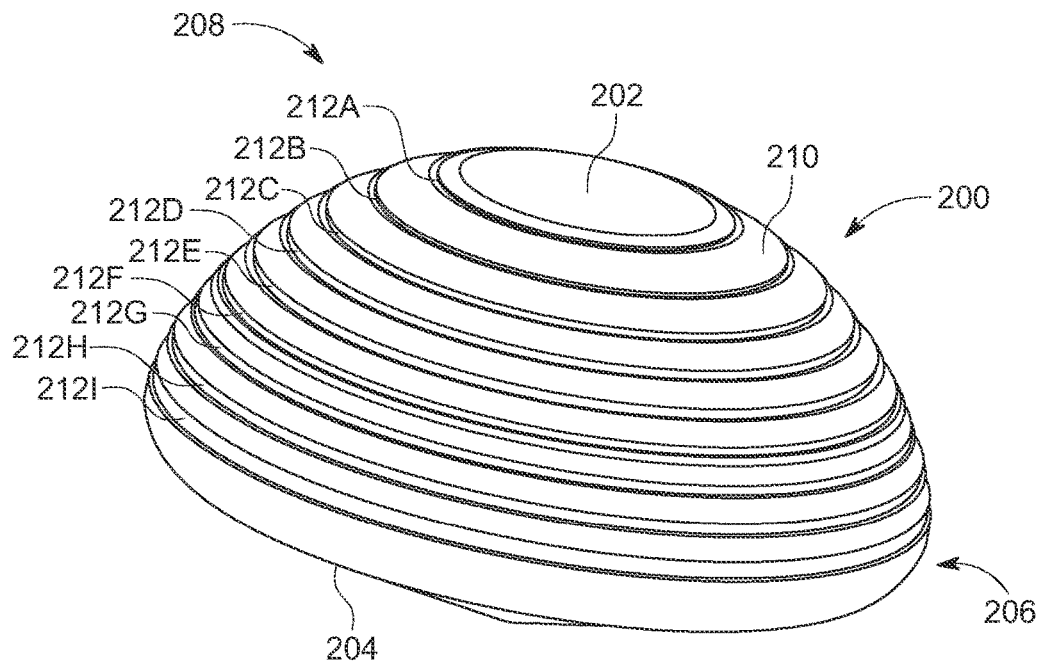
FIG. 8A shows a perspective view of a mandrel having constant depth grooves formed in an outer surface thereof, in accordance with one embodiment of the present patent application.
Figure 8B:
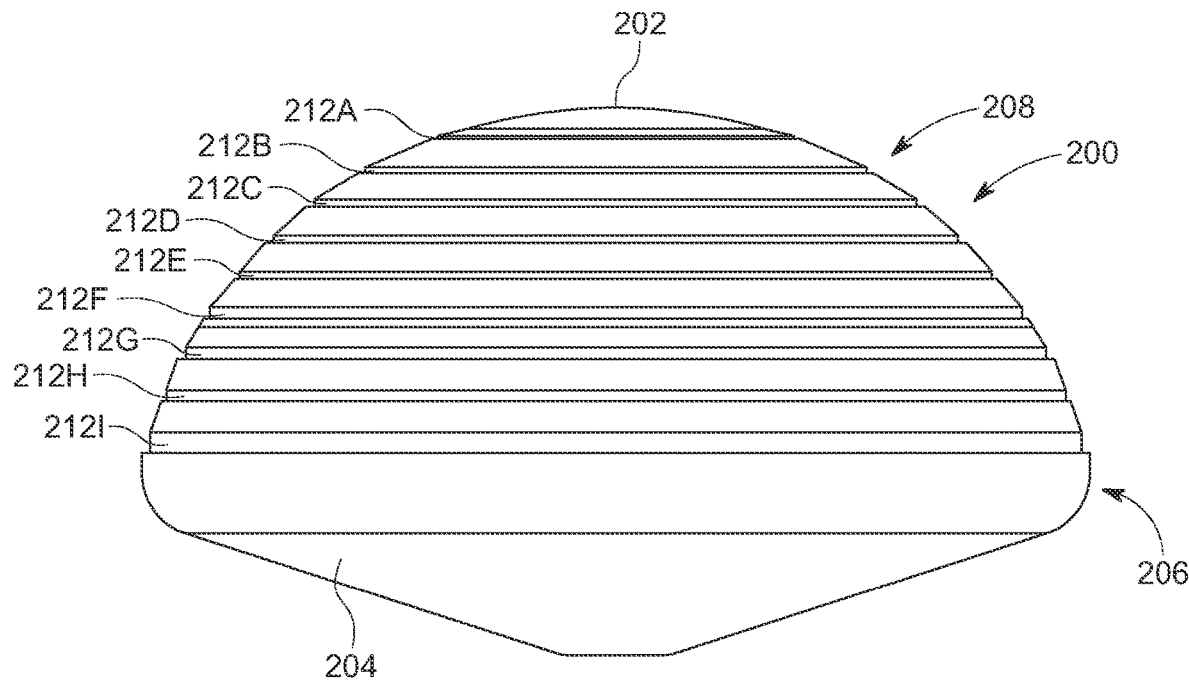
FIG. 8B shows a front elevation view of the mandrel shown in FIG. 8A.

Referring to FIGS. 8A and 8B, in one embodiment, a mandrel 200 utilized to make shells for mammary implants and tissue expanders preferably includes an apex 202, a base 204, a radius 206 that extends around the circumference or side of the mandrel, a dome 208 that extends between the apex 202 and the radius 206, and a convexly curved outer surface 210 that extends from the apex 202 to the radius 206.

In one embodiment, the mandrel 200 desirably includes a plurality of grooves 212A-212I that are formed in the outer surface 210 of the mandrel. The grooves may be circumferential grooves. The grooves may have a depth that is less than the depth of the grooves shown and described above for the embodiment of FIGS. 5A-5B and 6. In one embodiment, the grooves 212A-212I formed in the mandrel 200 have a constant depth, however, the height of each successive groove desirably increases between the apex 202 and the base 204 of the mandrel. In one embodiment, the grooves 212A-212I are evenly spaced from one another between the apex 202 and the base 204 of the mandrel 200.

Referring to FIG. 9, in one embodiment, the mandrel 200 has nine grooves 212A-212I formed in the convexly curved outer surface 210 thereof. In one embodiment, the mandrel 200 may have less than nine grooves or more than nine grooves. In one embodiment, each of the grooves 212A-212I desirably has a constant depth $D_2$ of about 0.025 inches as measured from the convexly curved outer surface 210 of the mandrel 200. In one embodiment, each of the grooves 212A-212I are evenly spaced from one another by a distance $S_2$ of about 0.150 inches.

In one embodiment, the mandrel 200 (FIGS. 8A and 8B) preferably has a first groove 212A having a height $H_{11}$ of about 0.009 inches, a second groove 212B having a height $H_{12}$ of about 0.014 inches, a third groove 212C having a height $H_{13}$ of about 0.019 inches, a fourth groove 212D having a height $H_{14}$ of about 0.024 inches, and a fifth groove 212E having a height $H_{15}$ of about 0.029 inches. In one embodiment, the mandrel 200 desirably includes a sixth groove 212F having a height $H_{16}$ of about 0.036 inches, a seventh groove 212G having a height $H_{17}$ of about 0.045 inches, an eighth groove 212H having a height $H_{18}$ of about 0.061 inches, and a ninth groove 212I having a height $H_{19}$ of about 0.094 inches.

In one embodiment, the grooves may extend circumferentially around the side of the mandrel, radially between the apex and the base of the mandrel, or at an angle or slope that is between a circumferential orientation and a radial orientation.

Figure 10A:
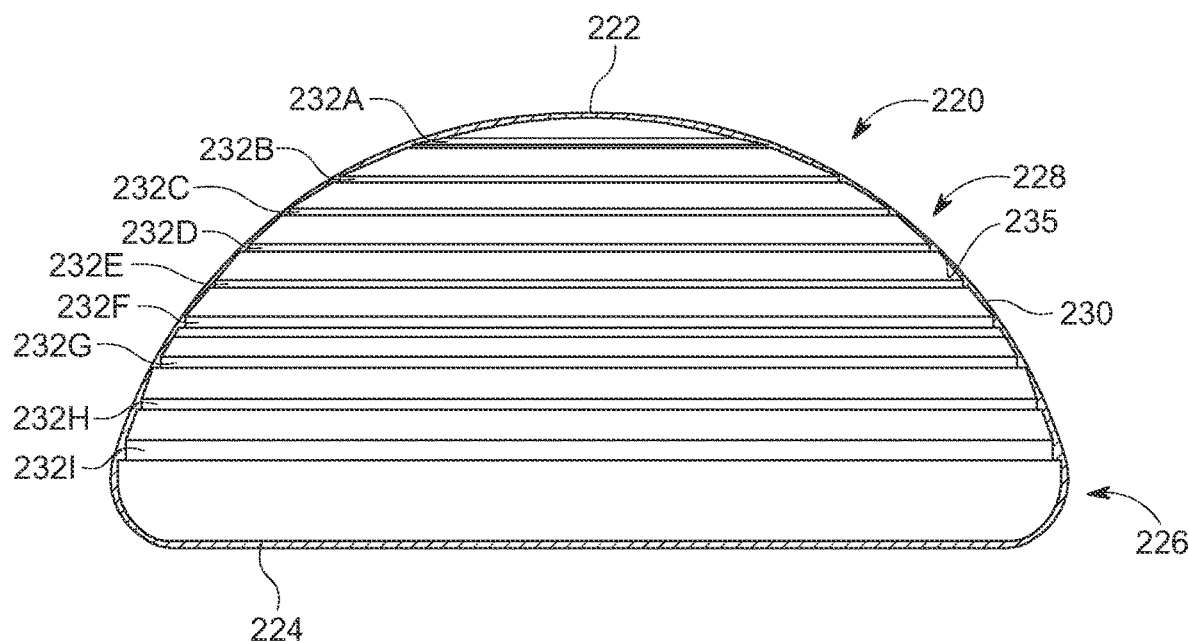
FIG. 10A shows a cross-sectional view of a shell that is made using the mandrel shown in FIGS. 8A-8B and 9, in accordance with one embodiment of the present patent application.
Figure 10B:
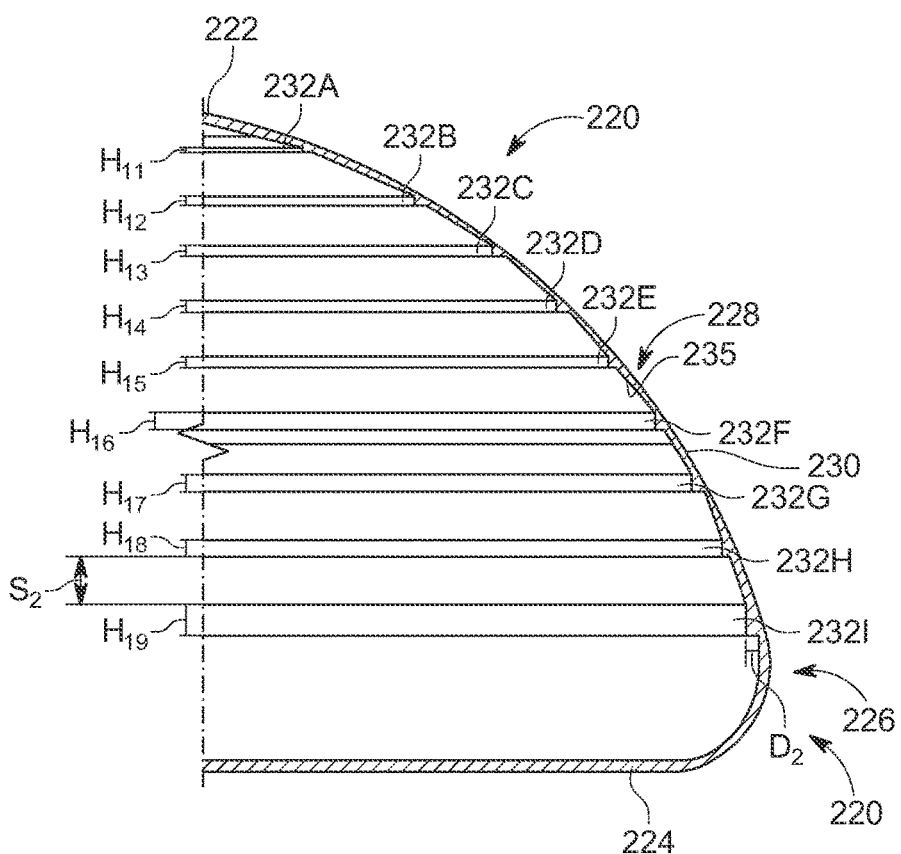
FIG. 10B shows a partial cross-sectional view of the shell of FIG. 10A.

Referring to FIGS. 10A and 10B, in one embodiment, the mandrel shown and described above in FIGS. 8A-8B and 9 may be utilized to form a shell 220 such as a silicone shell that may be used to make a mammary implant or a tissue expander. In one embodiment, the shell 220 preferably includes an apex 222, a base 224, a radius 226 that extends around a circumference or side of the shell, and a dome 228 that extends between the apex 222 and the radius 226. In one embodiment, the shell 220 preferably includes an outer surface 230 having a convexly curved shape and an inner surface 235 having a concave curved shape that surrounds an interior volume of the shell 220.

In one embodiment, the shell 220 desirably includes a plurality of ribs 232A-232I that project inwardly from the interior surface 235 of the shell 220. The inwardly projecting ribs 232A-232I preferably mirror the shape and dimension of the circumferential grooves 212A-212I of the mandrel 200 shown and described above in FIGS. 8A-8B and 9.

In one embodiment, the shell 220 desirably includes a first rib 232A having a height $H_{11}$ of about 0.009 inches, a second rib 232B having a height $H_{12}$ of about 0.014 inches, a third rib 232C having a height $H_{13}$ of about 0.019 inches, a fourth rib 232D having a height $H_{14}$ of about 0.024 inches, and a fifth rib 232E having a height $H_{15}$ of about 0.029 inches. In one embodiment, the shell 220 desirably includes a sixth rib 232F having a height $H_{16}$ of about 0.036 inches, a seventh rib 232G having a height $H_{17}$ of about 0.045 inches, an eighth rib 232H having a height $H_{18}$ of about 0.061 inches, and a ninth rib 232I having a height $H_{19}$ of about 0.094 inches. In one embodiment, the ribs 232A-232I are circumferential ribs that lie in planes that are parallel to one another.

In one embodiment, each of the ribs 232A-232I desirably projects inwardly from the inner surface 232 of the shell 220 by a constant distance $D_2$ of about 0.025 inches. In one embodiment, each of the ribs 232A-232I are evenly spaced from one another by a constant distance $S_2$ of about 0.150 inches. For example, in one embodiment, the distance $S_2$ between a lower end of the first rib 232A and an upper end of the second rib 232B is about 0.150 inches.

Figure 11A:
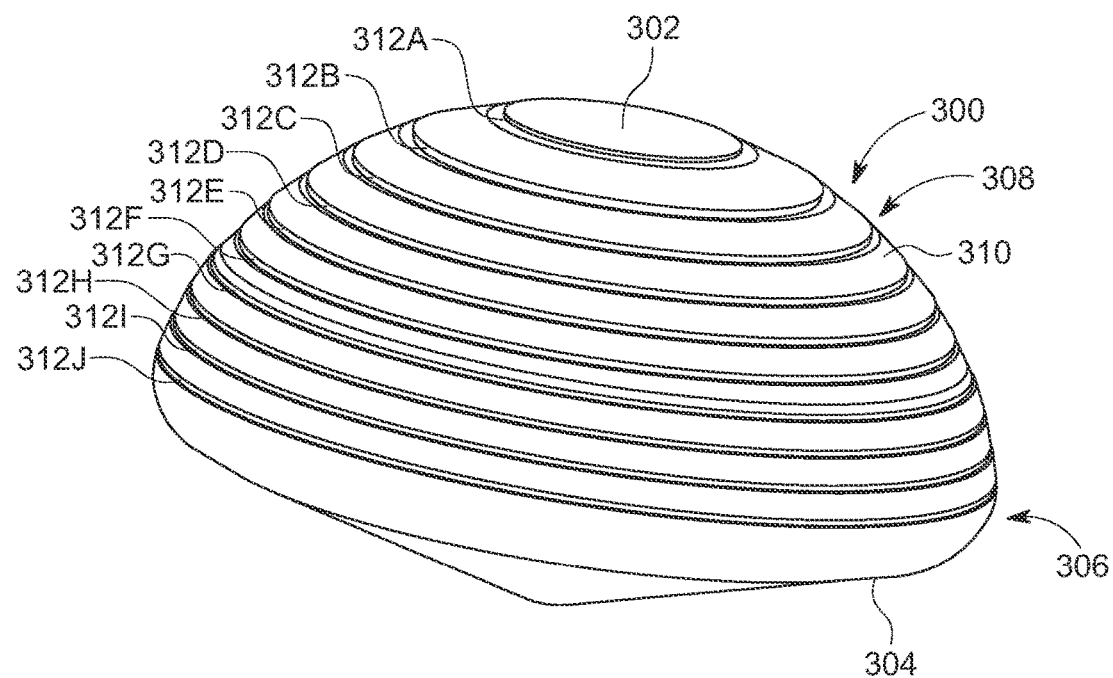
FIG. 11A shows a perspective view of a mandrel having constant height grooves formed in an outer surface thereof, in accordance with one embodiment of the present patent application.
Figure 11B:
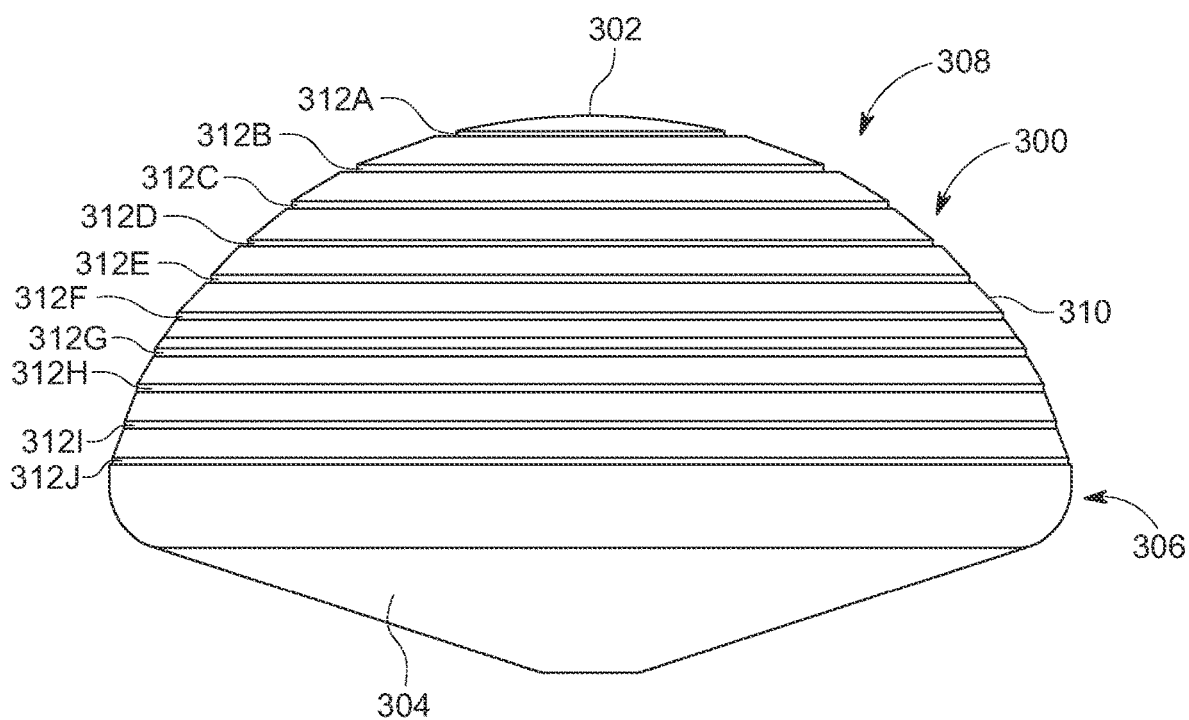
FIG. 11B shows a front elevation view of the mandrel shown in FIG. 11A.

Referring to FIGS. 11A and 11B, in one embodiment, a mandrel 300 utilized for making shells for mammary implants and tissue expanders preferably has grooves that are evenly spaced, that have a constant height, and that have different depths. In one embodiment, the mandrel 300 preferably has an apex 302, a base 304, a radius 306 extending around the side of the mandrel, and a dome 308 that extends between the apex 302 and the radius 306. In one embodiment, the mandrel 300 preferably has a convexly curved outer surface 310 that extends from the apex 302 to the base 304. In one embodiment, a series of grooves 312A-312J (e.g., circumferential grooves) are formed in the outer surface 310 of the mandrel. In one embodiment, the respective grooves 312A-312J have a constant height and different depths. In one embodiment, the depths of the respective grooves become shallower or decrease in size sequentially between the apex and the base of the mandrel. For example, a groove closer to the apex has a greater depth than a groove further away from the apex.

Figure 12:
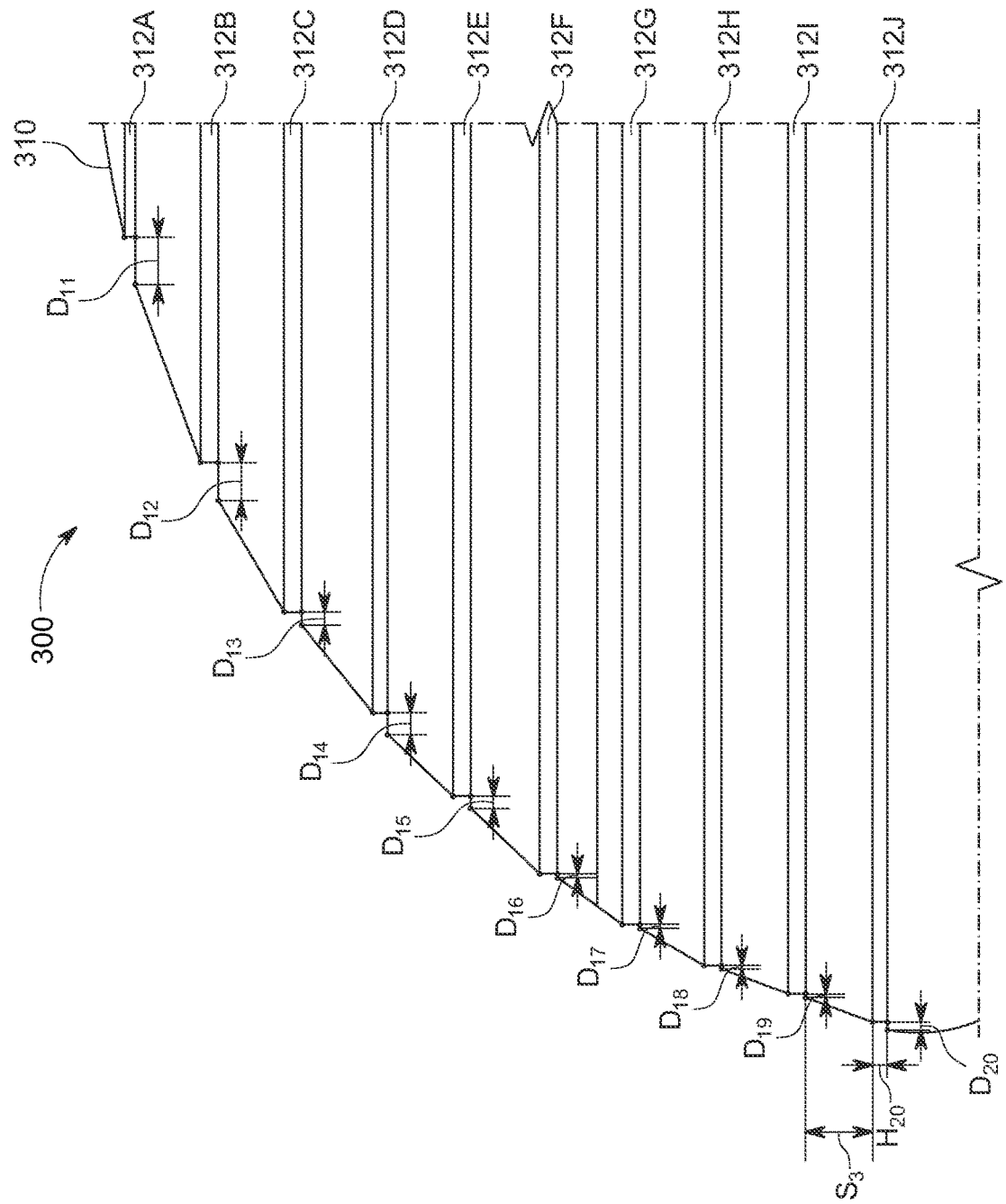
FIG. 12 shows a schematic view of a portion of the mandrel shown in FIGS. 11A and 11B.

Referring to FIG. 12, in one embodiment, the mandrel 300 of FIGS. 11A and 11B preferably has circumferential grooves 312A-312J formed in the outer surface 310 thereof. In one embodiment, each of the circumferential grooves 312A-312J has a height $H_{20}$ of about 0.025 inches. In one embodiment, the circumferential grooves 312A-312J are evenly spaced from one another by a distance $S_3$ of about 0.150 inches.

In one embodiment, each respective circumferential groove 312A-312J has a different depth relative to the outer surface 310 of the mandrel 300. In one embodiment, the respective depths of the grooves increase in size sequentially between the apex and the base of the mandrel 300. In one embodiment, a first groove 312A has a depth $D_{11}$ of about 0.094 inches, a second groove 312B has a depth $D_{12}$ of about 0.049 inches, a third groove 312C has a depth $D_{13}$ of about 0.035 inches, a fourth groove 312D has a depth $D_{14}$ of about 0.027 inches, and a fifth groove 312E has a depth $D_{15}$ of about 0.022 inches. In one embodiment, the mandrel desirably includes a sixth groove 312F having a depth $D_{16}$ of about 0.018 inches, a seventh groove 312G having a depth $D_{17}$ of about 0.015 inches, an eighth groove 312H having a depth $D_{18}$ of about 0.012 inches, a ninth groove 312I having a depth $D_{19}$ of about 0.009 inches, and a tenth 312J having a depth $D_{20}$ of about 0.006 inches. In one embodiment, the mandrel 300 may have fewer than ten grooves or more than ten grooves.

Figure 13A:
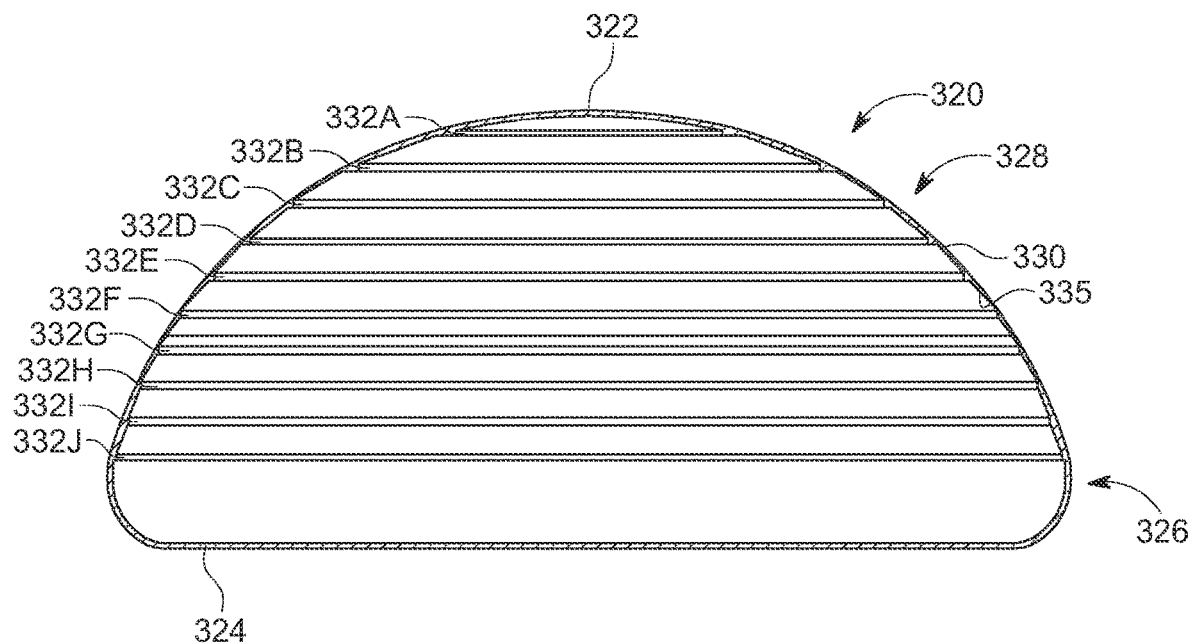
FIG. 13A shows a cross-sectional view of a shell that is made using the mandrel shown in FIGS. 11A-11B and 12, in accordance with one embodiment of the present patent application.
Figure 13B:
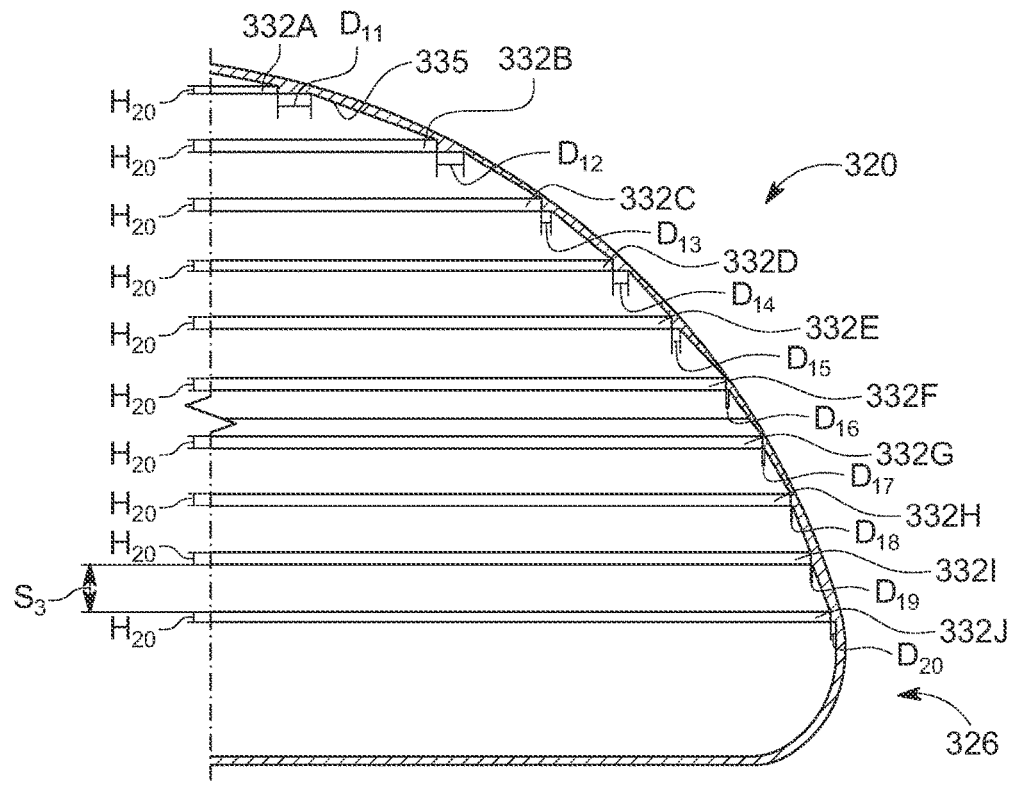
FIG. 13B shows a partial cross-sectional view of the shell of FIG. 13A.

Referring to FIGS. 13A and 13B, in one embodiment, the mandrel shown in FIGS. 11A-11B and 12 is utilized to make a shell 320 for a mammary implant or a tissue expander. In one embodiment, a shell 320 includes an apex 322, a base 324, a radius 326 that extends around the circumference or side of the shell, and a dome region 328 that extends between the apex 322 and the radius 326. In one embodiment, the shell 320 has a convexly curved outer surface 330 and a concave curved inner surface 335 that surrounds an interior region of the shell. In one embodiment, the shell 320 desirably includes a plurality of ribs 332A-332J (e.g., circumferential ribs) that project inwardly from the concave inner surface 335 of the shell 320. The inwardly projecting ribs 332A-332J preferably have the same size, shape, and dimension as the circumferential grooves 312A-312J formed in the mandrel shown above in FIGS. 11A-11B and 12.

In one embodiment, each of the ribs 332A-332J desirably has a constant height designated $H_{20}$ of about 0.025 inches. In one embodiment, the ribs 332A-332J are evenly spaced from one another between the apex 322 and the base 324 by a distance $S_3$ of about 0.150 inches.

In one embodiment, each of the respective ribs 332A-332J projects inwardly from the inner surface 335 of the shell 320 by different distances. In one embodiment, a first rib 332A has a depth $D_{11}$ of about 0.094 inches, a second rib 332B has a depth $D_{12}$ of about 0.049 inches, a third rib 312C has a depth $D_{13}$ of about 0.035 inches, a fourth rib 332D has a depth $D_{14}$ of about 0.027 inches, and a fifth rib 332E has a depth $D_{15}$ of about 0.022 inches. In one embodiment, the shell 320 preferably includes a sixth rib 332F having a depth $D_{16}$ of about 0.018 inches, a seventh rib 332G having a depth $D_{17}$ of about 0.015 inches, an eighth circumferential rib 332H having a depth $D_{18}$ of about 0.012 inches, a ninth rib 332I having a depth $D_{19}$ of about 0.009 inches, and a tenth rib 332J having a depth $D_{20}$ of about 0.006 inches. In one embodiment, the ribs are circumferential ribs that extend in planes that are parallel to one another. In one embodiment, the ribs extend radially between the apex and the base of the shell. In one embodiment, the ribs slope between the apex and the base.

Figure 14A:
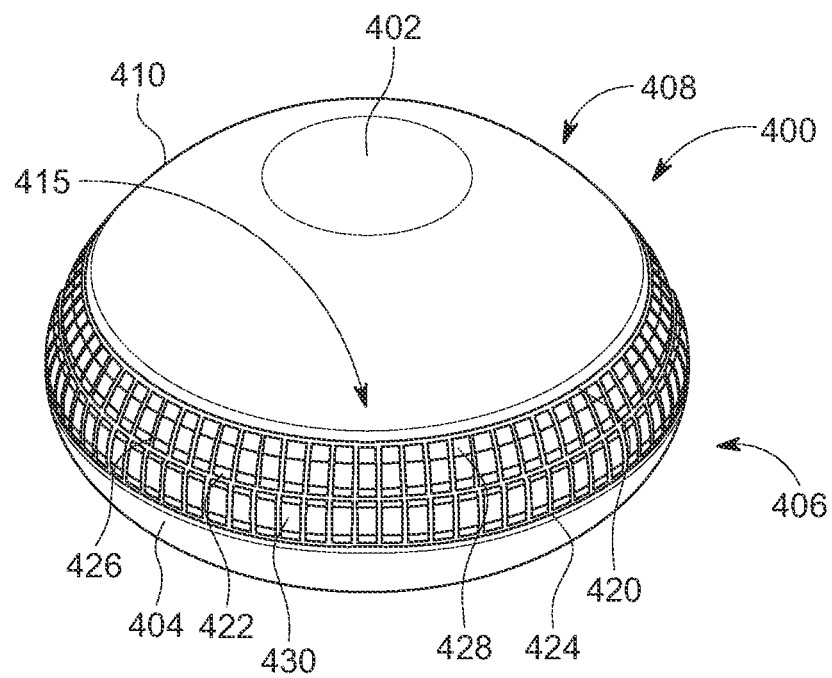
FIG. 14A shows a perspective view of a mandrel having a mesh shaped groove pattern formed in an outer surface thereof, in accordance with one embodiment of the present patent application.
Figure 14B:
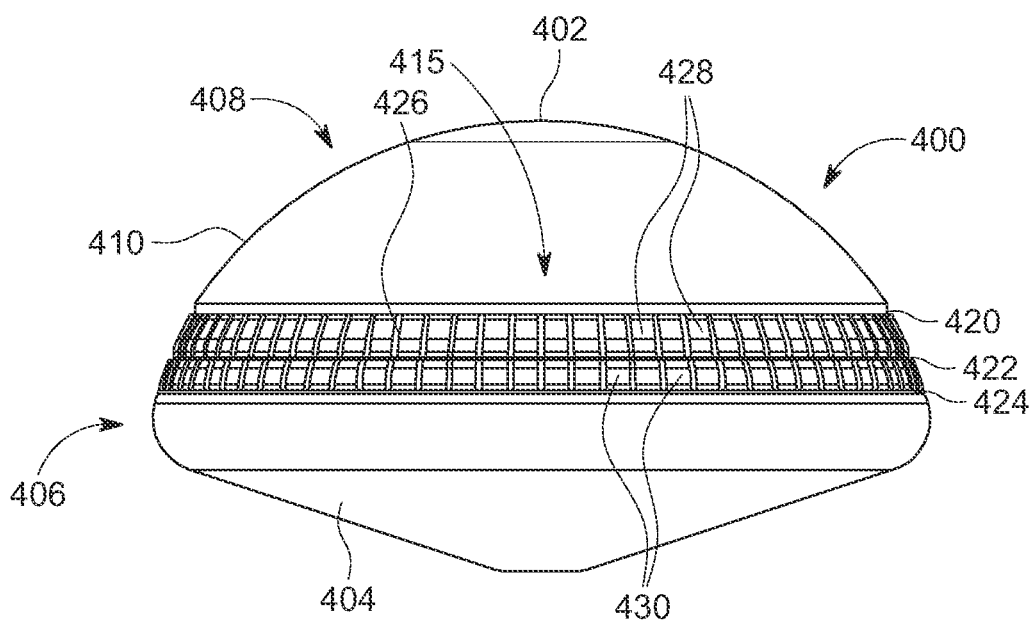
FIG. 14B shows a front elevation view of the mandrel shown in FIG. 14A.
Figure 14C:
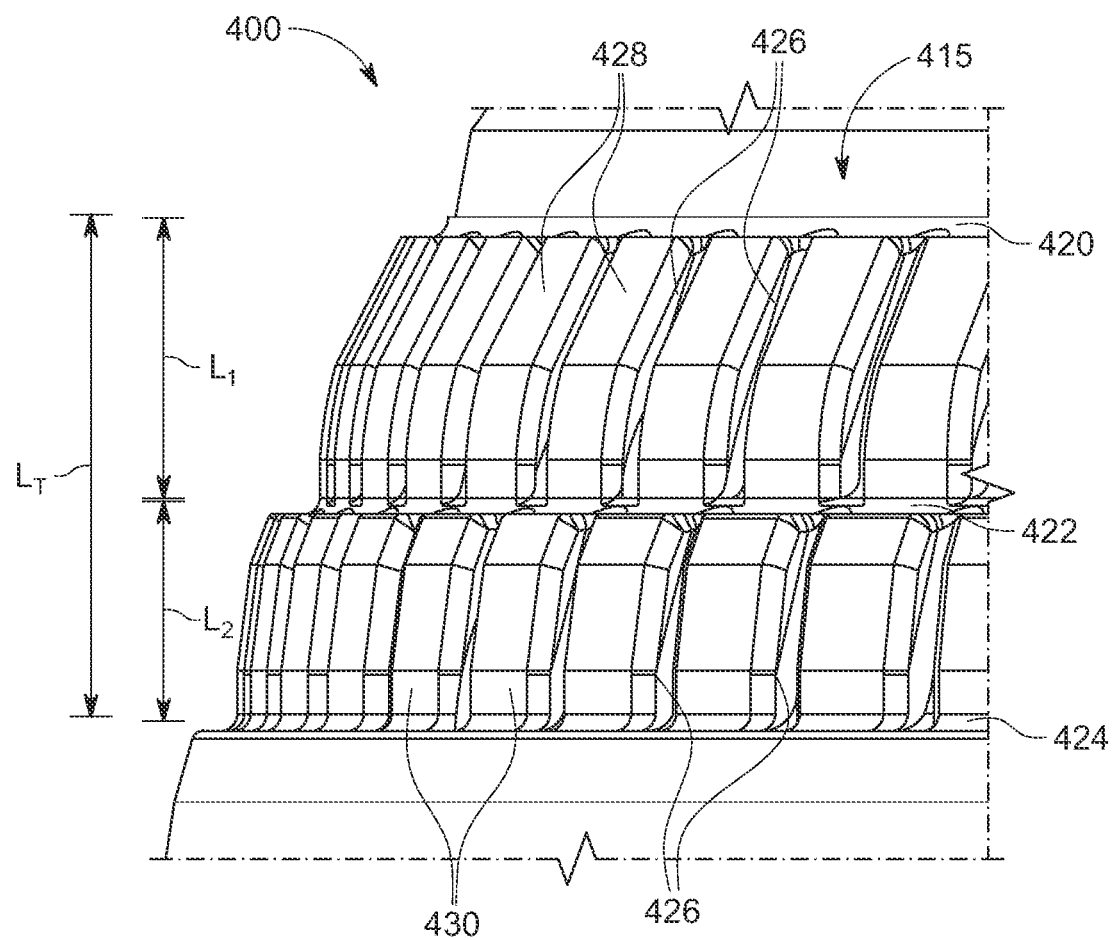
FIG. 14C shows a magnified view of a section of the mesh shaped groove pattern shown in FIGS. 14A and 14B.

Referring to FIGS. 14A-14C, in one embodiment, a mandrel 400 for making shells used for mammary implants and tissue expanders preferably includes an apex 402 that defines an upper end of the mandrel, a base 404 that defines a lower end of the mandrel, a radius 406 that extends around the circumference or side of the mandrel 400, and a dome 408 that extends from the apex 402 to the radius 406. In one embodiment, the apex 402 and the dome 408 of the mandrel 400 define an outer surface 410 of the mandrel having a convexly curved shape. In one embodiment, a mesh shaped groove pattern 415 is formed in the outer surface 410 of the mandrel 400. The mesh shaped groove pattern 415 may be formed by removing material from the mandrel, adding material to the outer surface of the mandrel (e.g., 3D printing), or using a mold to form the mandrel. The mesh shaped groove pattern 415 preferably extends around the circumference of the mandrel in the region of the radius 406 of the mandrel.

In one embodiment, the mesh shaped groove pattern 415 preferably includes an upper circumferential groove 420 that extends around the circumference of the mandrel, an intermediate circumferential groove 422 that extends around the circumference of the mandrel, and a lower circumferential groove 424 that extends around the circumference of the mandrel. The intermediate circumferential groove is preferably located between the upper circumferential groove and the lower circumferential groove. In one embodiment, the circumferential grooves 420, 422 and 424 may lie in respective planes that are parallel with one another. In one embodiment, the circumferential grooves 420, 422, and 422 desirably define bands that extend around the circumference of the mandrel. The bands may extend completely or partially around the circumference of the mandrel.

In one embodiment, the mesh shaped groove pattern 415 preferably includes radial grooves 426 that extend from the upper circumferential groove 420, through the intermediate circumferential groove 422, and to the lower circumferential groove 424. The radial grooves 426 preferably extend in a radial direction that runs from the apex 402 to the base 404 of the mandrel 400. In one embodiment, the radial grooves 426 may be vertical grooves that are evenly spaced from one another around the circumference of the mandrel 400. The radial grooves 426 preferably intersect the circumferential grooves 420, 422 and 424 and cooperatively divide the mesh shaped groove pattern 415 into upper islands 428 located above the intermediate circumferential groove 422 and lower islands 430 located below the intermediate circumferential groove 422. The respective upper and lower islands 428, 430 preferably extend around the circumference of the mandrel. The upper and lower islands 428, 430 may extend partially or completely around the circumference of the mandrel. In one embodiment, the vertical grooves 426 are spaced from one another by a distance $W_1$ of about 0.170 inches.

Figure 15:
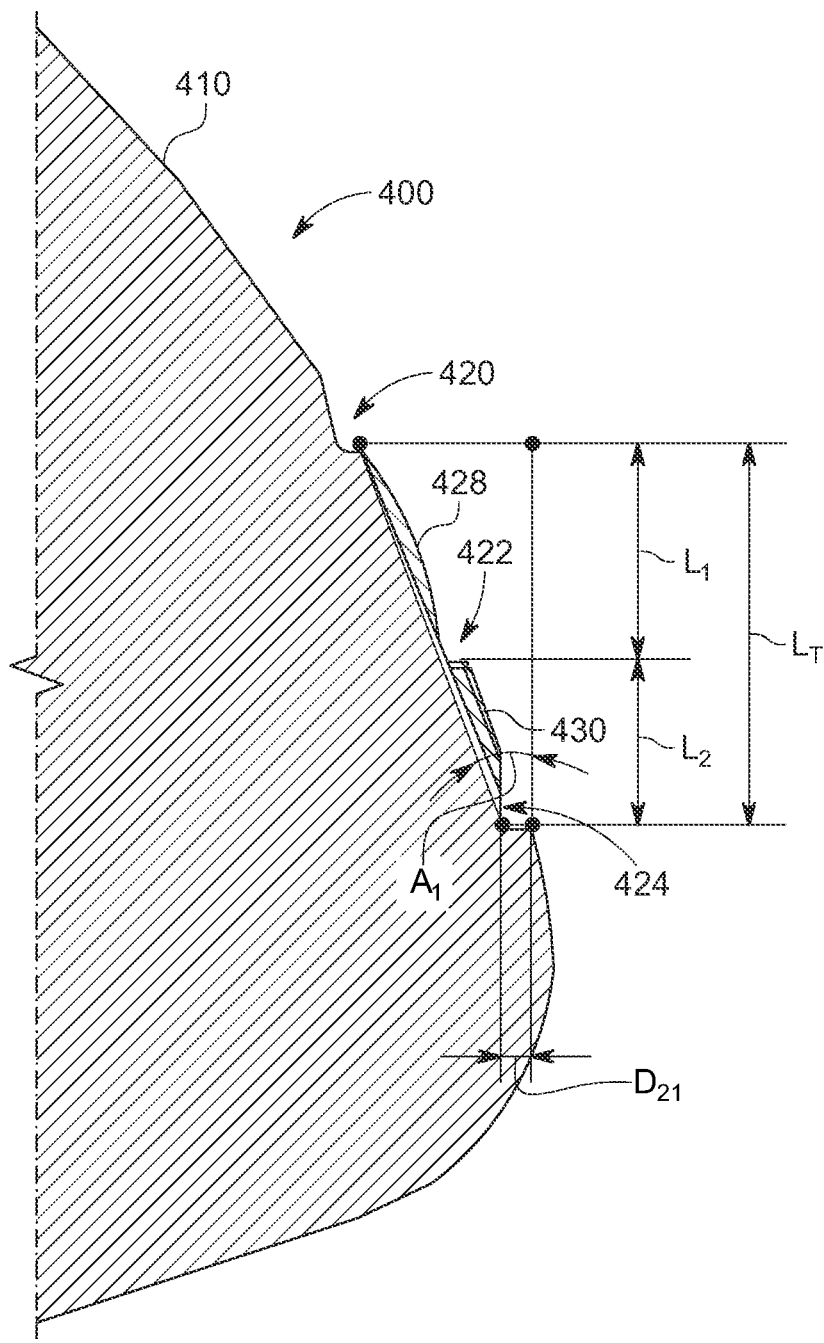
FIG. 15 shows a magnified side view of a portion of the mesh shaped groove pattern shown in FIGS. 14A-14C.

Referring to FIGS. 14C and 15, in one embodiment, the distance between the upper circumferential groove 420 and the intermediate circumferential groove 422 is $L_1$ or about 0.25 inches. In one embodiment, the distance between the intermediate circumferential groove 422 and the lower circumferential groove 424 is $L_2$ or about 0.20 inches. In one embodiment, the distance between the upper circumferential groove 420 and the lower circumferential groove 424 is $L_T$ or about 0.45 inches.

Referring to FIG. 15, in one embodiment, each of the circumferential grooves 420, 422, 424 is formed in the outer surface 410 of the mandrel 400 and has a depth $D_{21}$ of about 0.03 inches. In one embodiment, the vertically extending groove 426 preferably extends along a slope that defines an angle $\alpha_1$ with a vertical axis $A_1$ that is about 21 degrees. The upper island 428 is bounded by the upper circumferential groove 420 and the intermediate circumferential groove 422. The lower island 430 is bounded by the intermediate circumferential groove 422 and the lower circumferential groove 424. The grooves preferably have rounded or concave surfaces to avoid the presence of sharp edges, which will facilitate the removal of cured shells from the mandrel without damaging (e.g., tearing) the shells.

Figure 16:
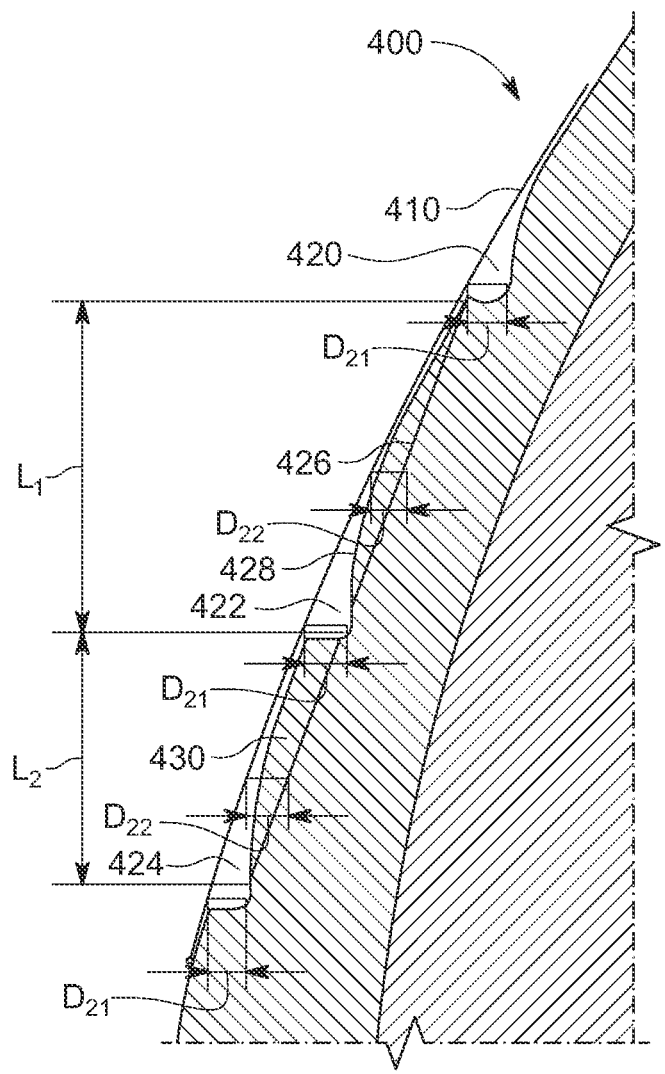
FIG. 16 shows another magnified side view of a portion of the mesh shaped groove pattern shown in FIGS. 14A-14C.

Referring to FIG. 16, in one embodiment, the circumferential grooves 420, 422, 424 and the vertical grooves 426 are cut into the outer surface 410 of the mandrel 400 to form the upper islands 428 and the lower islands 430 of the mesh shaped groove pattern 415 (FIG. 14C). Each of the circumferential grooves 420, 422, 424 is preferably cut to a depth $D_{21}$ of about 0.03 inches. In one embodiment, the upper circumferential groove 420 is spaced from the intermediate circumferential groove 422 by a distance $L_1$ of about 0.25 inches. In one embodiment, the intermediate circumferential groove 422 is spaced from the lower circumferential groove 424 by a distance $L_2$ of about 0.20 inches. The vertical groove 426 has a depth $D_{22}$ of about 0.03 inches relative to an arc that defines the outer surface 410 of the mandrel 400.

Figure 17:
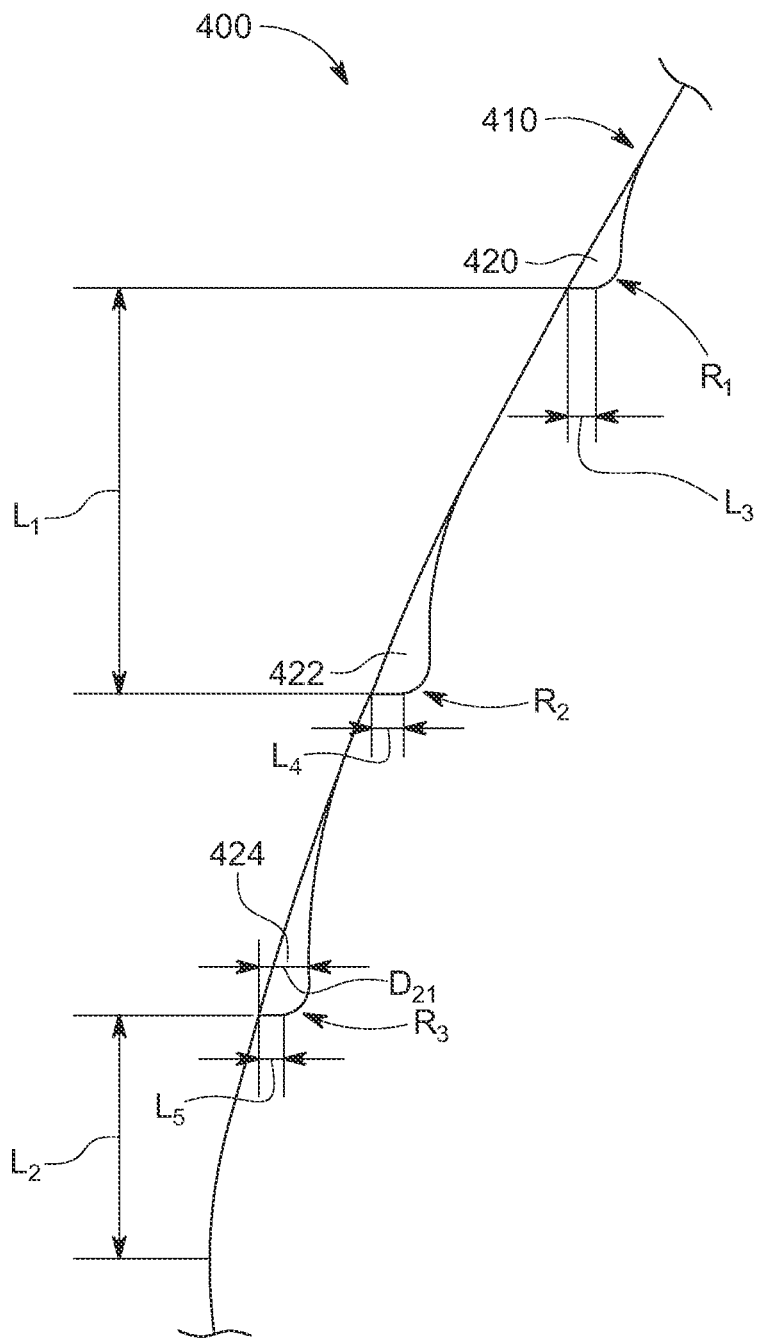
FIG. 17 shows a schematic view of the mesh shaped groove pattern shown in FIGS. 15 and 16.

Referring to FIG. 17, in one embodiment, the upper circumferential groove 420 is desirably formed (e.g., cut) in the outer surface 410 of the mandrel 400. The upper circumferential groove 420 has a horizontal section having a length $L_3$ of about 0.020 inches and a concave surface have a radius $R_1$ of about 0.016 inches. In one embodiment, the intermediate circumferential groove 422 has a first section with a length $L_4$ of about 0.020 inches and a concave surface having a radius $R_2$ of about 0.016 inches. In one embodiment, the lower circumferential groove 422 has a first section with a length $L_5$ of about 0.016 inches and a concave surface having a radius $R_3$ of about 0.016 inches. Providing circumferential grooves 420, 422, and 424 having concave surfaces preferably minimizes damage to shells as the shells are removed (e.g., peeled away from) the mandrel. In one embodiment, each respective circumferential groove 420, 422, 424 has a respective depth $D_{21}$ of about 0.03 inches. The distance between the base of the upper circumferential groove 420 and the base of the intermediate circumferential groove 422 is designated $L_1$ or about 0.25 inches. The distance between the base of the intermediate circumferential groove 422 and the lower circumferential groove 424 is designated $L_2$ or about 0.20 inches.

Figure 18A:
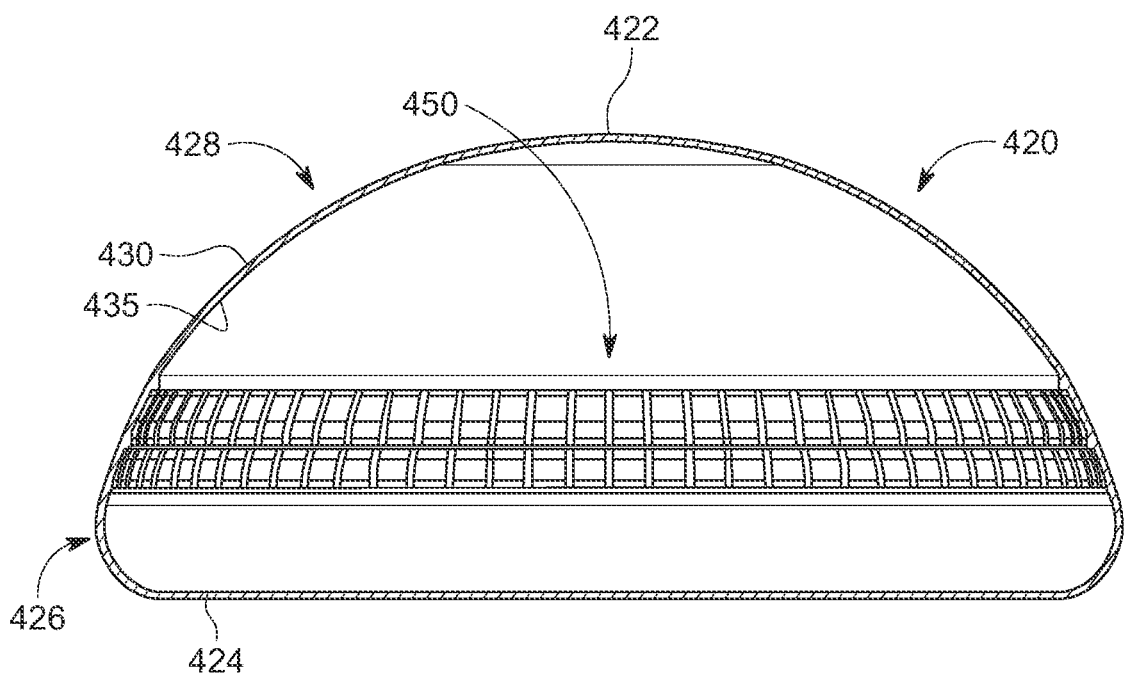
FIG. 18A shows a cross-sectional view of a shell that is made using the mandrel shown in FIGS. 14A-14C, 15, 16, and 17, in accordance with one embodiment of the present patent application.
Figure 18B:
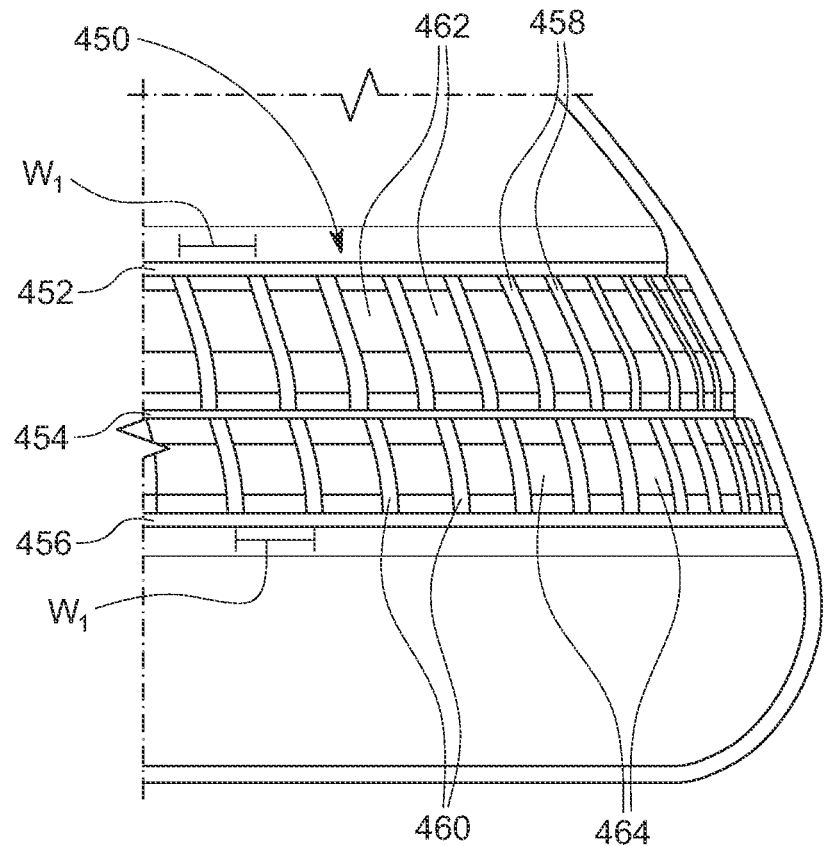
FIG. 18B shows a partial cross-sectional view of the shell of FIG. 18A.

Referring to FIGS. 18A and 18B, in one embodiment, the mandrel shown and described above in FIGS. 14A-14C and 15-17 may be utilized to make a shell 420 for mammary implants and tissue expanders. The shell 420 preferably has a meshed shaped rib pattern that mirrors the mesh shaped groove pattern 415 shown and described above in FIGS. 14A-14C and 15-17. In one embodiment, the shell 420 preferably includes an apex 422, a base 424, a radius 426 that extends around the circumference of the shell 420, and a dome 428 that extends between the apex 422 and the radius 426. In one embodiment, the shell 420 has a mesh shaped rib pattern 450 molded therein that projects inwardly from the inner surface 435 of the shell 420. The mesh shaped rib pattern 450 preferably enhances the structural integrity and stability of the shell 420 to enhance projection of the apex 422, and minimize the occurrence of the ashtray effect, rippling, wrinkling, and/or scalloping.

In one embodiment, the mesh shaped rib pattern 450 formed in the shell 420 preferably includes an upper circumferential rib 452, an intermediate circumferential rib 454, and a lower circumferential rib 456 that extend around the circumference of the shell 420 and that project inwardly from the inner surface 435 of the shell. The circumferential ribs 452, 454 and 456 preferably match and mirror the size, shape and dimension of the circumferential grooves 420, 422 and 424 shown and described above in the mandrel 400 of FIGS. 14A-14C and 15-17.

In one embodiment, the mesh shaped rib pattern 450 desirably includes vertically extending upper ribs 458 that extend between the circumferential upper rib 452 and the circumferential intermediate rib 454, and vertically extending lower ribs 460 that extend between the circumferential intermediate rib 454 and the circumferential lower rib 456. The vertically extending upper and lower ribs 458, 460 preferably match and mirror the size, shape and dimension of the vertical grooves 426 shown and described above in the mandrel 400 of FIGS. 14A-14C and 15-17. In one embodiment, the mesh shaped rib pattern of the shell matches the mesh shaped groove pattern of the mandrel shown in FIGS. 14A-14C.

In one embodiment, the vertically extending upper ribs 458 are evenly spaced from one another around the circumference of the shell, and upper islands 462 are located between the vertically extending upper ribs 458. In one embodiment, the spacing between adjacent vertically extending upper ribs 458 is designated $W_1$ or about 0.170 inches. In one embodiment, the vertically extending lower ribs 460 are evenly spaced from one another around the circumference of the shell, and lower islands 464 are located between the vertically extending lower ribs 460. In one embodiment, the spacing between the vertically extending lower ribs 460 is $W_1$ or about 0.170 inches.

Figure 19:
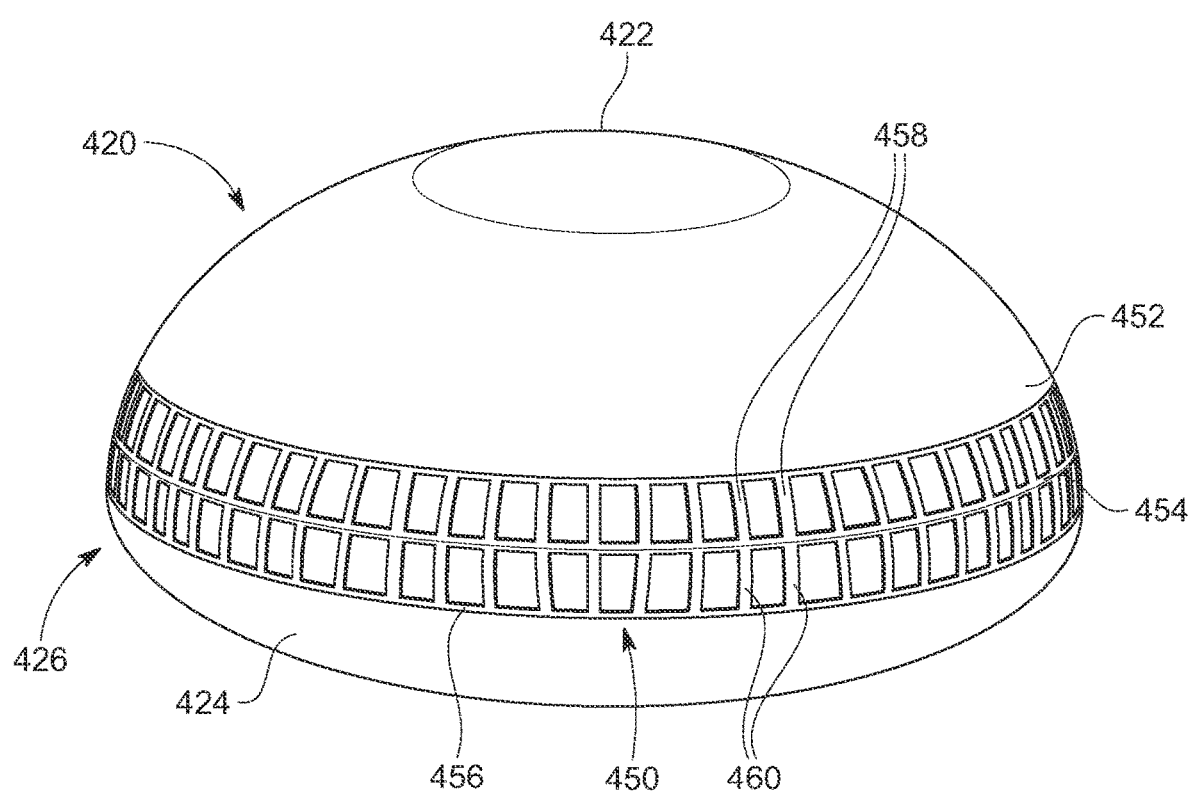
FIG. 19 shows a perspective view of a solution filled shell that is made using the mandrel shown in FIGS. 14A-14C, 15, 16, and 17, in accordance with one embodiment of the present patent application.

FIG. 19 shows a perspective view of the shell 420 shown and described above in FIGS. 18A-18B. In one embodiment, the shell 420 is filled with gel, saline, foam, gas, or a combination of two or more of the above-listed elements. The shell 420 preferably has an apex 422, a base 424, and a radius 426 that extends around the circumference of the shell. The shell 420 includes the mesh shaped rib pattern 450 that projects inwardly from the inner surface of the shell 420 for stabilizing the radius 426 of the shell and enhancing the projection of the shell. The mesh shaped rib pattern desirably includes the circumferential upper groove 452, the circumferential intermediate groove 454, the circumferential lower groove 456, the vertically extending upper ribs 458, and the vertically extending lower ribs 460. Upper islands 462 are bounded by the vertically extending upper ribs 458, the circumferential upper rib 452, and the circumferential intermediate rib 454. Lower islands 464 are bounded by the vertically extending lower ribs 460, the circumferential intermediate rib 454, and the circumferential lower rib 456.

The rib patterns disclosed in the present patent application preferably improve form stability or the ability of an implant to maintain its shape. The rib patterns disclosed herein preferably increase strength and rigidity without increasing the shell wall thickness, thus maintaining softness while improving form stability. Increasing the coverage and depth of the ribs greatly influence the form stability. Ribs may extend radially between the implant radius and apex, and circumferentially around the sides of the implant.

Figure 20A:
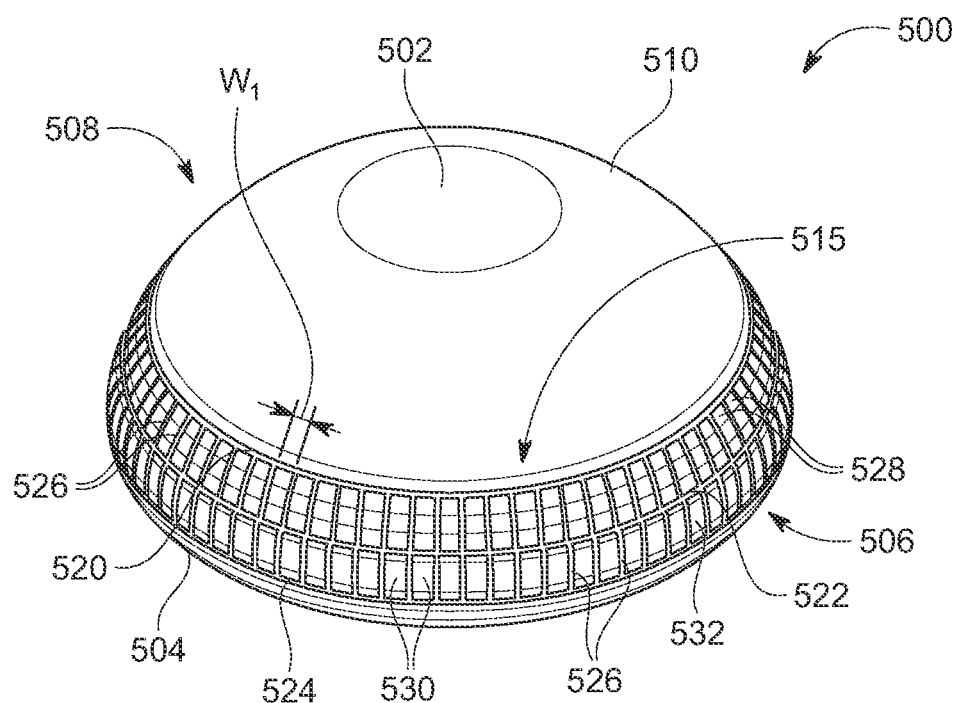
FIG. 20A shows a perspective view of a mandrel having a mesh shaped groove pattern formed in an outer surface thereof, in accordance with one embodiment of the present patent application.
Figure 20B:
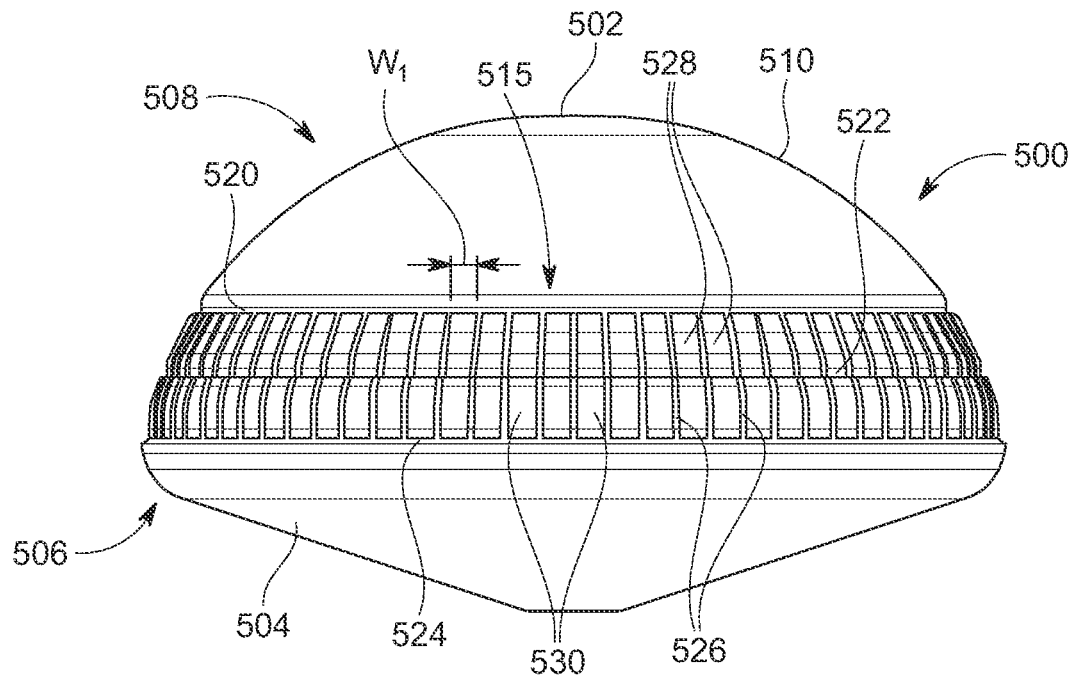
FIG. 20B shows a front elevation view of the mandrel shown in FIG. 20A.
Figure 20C:
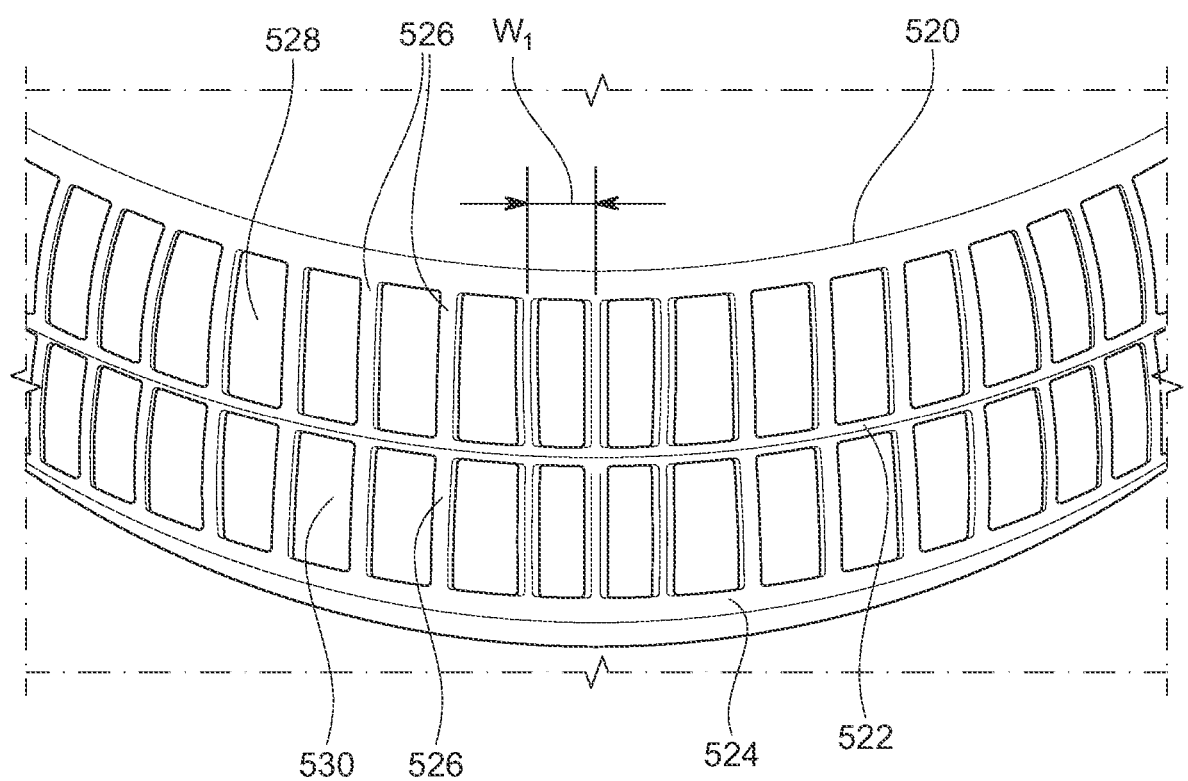
FIG. 20C shows a magnified view of a section of the mesh shaped groove pattern shown in FIGS. 20A and 20B.

Referring to FIGS. 20A-20C, in one embodiment, a mandrel 500 for making shells used for mammary implants and tissue expanders preferably includes an apex 502 that defines an upper end of the mandrel, a base 504 that defines a lower end of the mandrel, a radius 506 that extends around the circumference or sides of the mandrel 500, and a dome 508 that extends from the apex 502 to the radius 506. In one embodiment, the apex 502 and the dome 508 of the mandrel 500 define an outer surface 510 of the mandrel having a convexly curved shape. In one embodiment, the mandrel 500 has a mesh shaped groove pattern 515 formed in the outer surface 510 thereof. The mesh shaped groove pattern 515 may be formed by removing material from the mandrel, adding material to the outer surface of the mandrel (e.g., 3D printing), or using a mold to form the mandrel. The mesh shaped groove pattern 515 preferably extends around the circumference of the mandrel in the region of the radius 506 of the mandrel.

In one embodiment, the mesh shaped groove pattern 515 preferably includes an upper circumferential groove 520 that extends around the circumference of the mandrel, an intermediate circumferential groove 522 that extends around the circumference of the mandrel, and a lower circumferential groove 524 that extends around the circumference of the mandrel. In one embodiment, the circumferential grooves 520, 522 and 524 may lie in respective planes that are parallel with one another. In one embodiment, the circumferential grooves 520, 522, and 522 desirably form bands that extend completely around the circumference of the mandrel. In one embodiment, the circumferential grooves have rounded, curved and/or concave curved surfaces to avoid the presence of sharp edges, thereby minimizing the potential for damaging a shell as a shell is removed from the mandrel.

In one embodiment, the mesh shaped groove pattern 515 preferably includes vertically extending or radial grooves 526 that extend from the upper circumferential groove 520, through the intermediate circumferential groove 522, and to the lower circumferential groove 524. The radial grooves 526 preferably extend in a radial direction that runs from the apex 502 to the base 504 of the mandrel 500. In one embodiment, the radial grooves 526 may be vertical grooves that are evenly spaced from one another around the circumference of the mandrel 500. The radial grooves 526 preferably intersect the circumferential grooves 520, 522 and 524 and cooperatively divide the mesh shaped groove pattern 515 into upper islands 528 located above the intermediate circumferential groove 522 and lower islands 530 located below the intermediate circumferential groove 522. The respective upper and lower islands 528, 530 preferably extend around the circumference of the mandrel. In one embodiment, the radial grooves 526 are spaced from one another a distance $W_1$ of about 0.170 inches. In one embodiment, the upper islands 528 are spaced and divided from one another by the radial grooves 526. In one embodiment, the lower islands 530 are spaced and divided from one another by the radial grooves 526.

Figure 21:
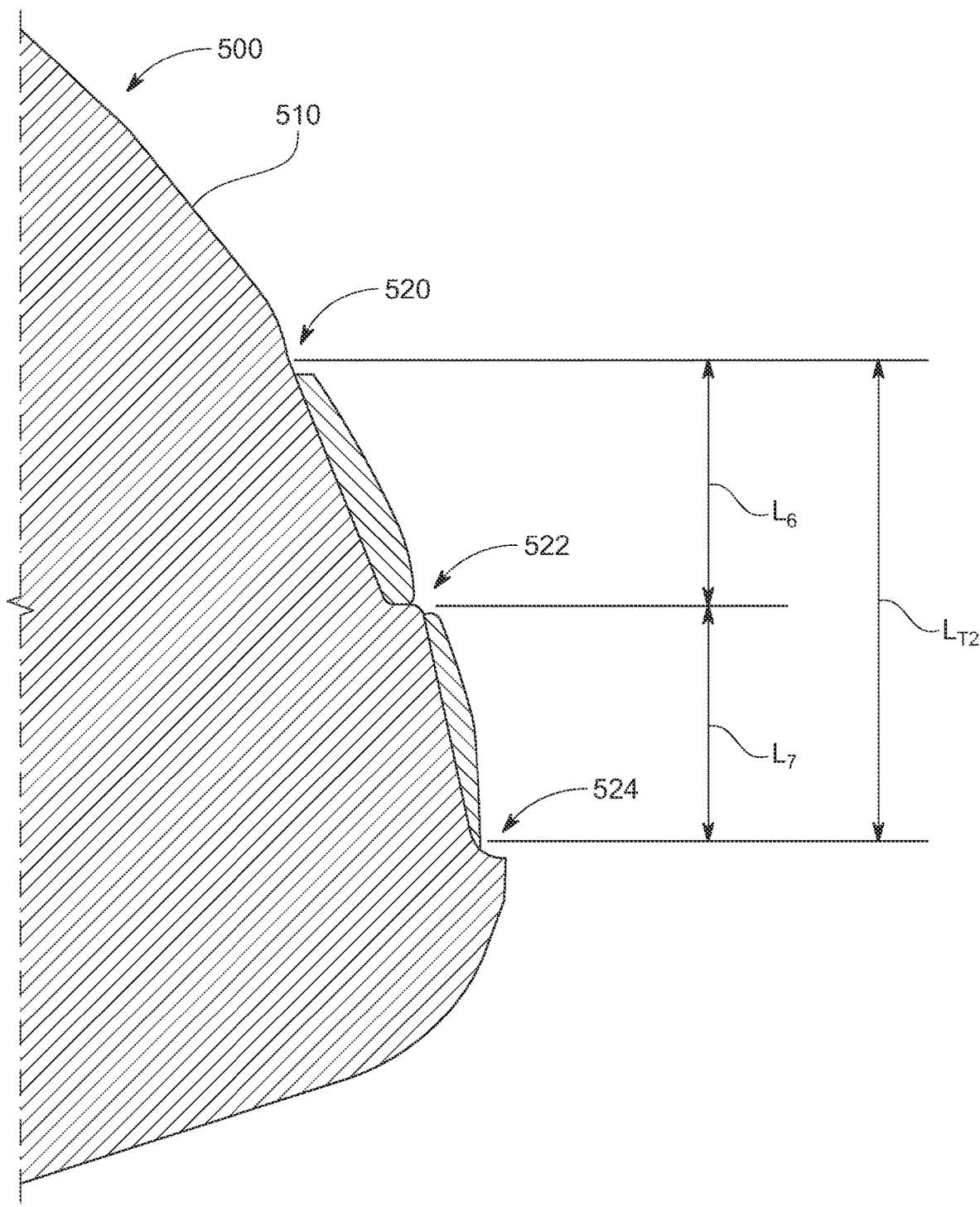
FIG. 21 shows a magnified side view of a portion of the mesh shaped groove pattern shown in FIGS. 20A-20C.

Referring to FIG. 21, in one embodiment, the distance between the upper circumferential groove 520 and the intermediate circumferential groove 522 is $L_6$ or about 0.34 inches. In one embodiment, the distance between the intermediate circumferential groove 522 and the lower circumferential groove 524 is $L_7$ or about 0.34 inches. In one embodiment, the distance between the upper circumferential groove 520 and the lower circumferential groove 524 is $L_{T2}$ or about 0.68 inches.

Figure 22:
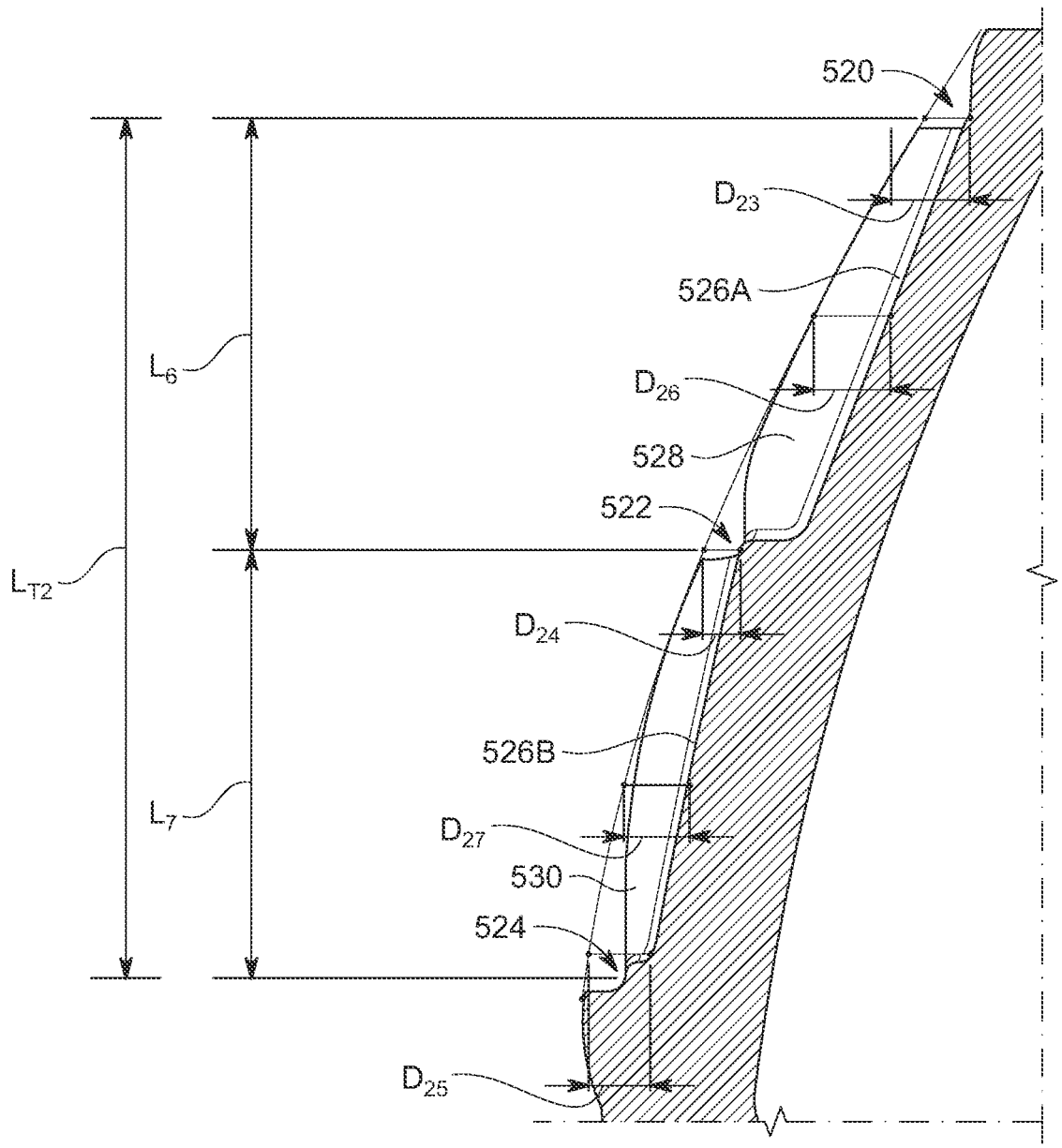
FIG. 22 shows another magnified side view of a portion of the mesh shaped groove pattern shown in FIGS. 20A-20C.

Referring to FIG. 22, in one embodiment, each of the circumferential grooves 520, 522, 524 is formed in the outer surface 510 of the mandrel 500. In one embodiment, the upper circumferential groove 520 has a depth $D_{23}$ of about 0.04 inches. In one embodiment, the intermediate circumferential groove 522 has a depth $D_{24}$ of about 0.03 inches. In one embodiment, the lower circumferential groove 524 has a depth $D_{25}$ of about 0.04 inches. In one embodiment, the vertically extending groove 526 preferably extends along a slope. In one embodiment, the vertically extending groove has an upper portion 526A that passes by the upper island 528 having a depth $D_{26}$ of about 0.06 inches and a lower portion 526B that passes by the lower island 530 having a depth $D_{27}$ of about 0.05 inches. The upper island 528 is bounded by the upper circumferential groove 520 and the intermediate circumferential groove 522. The lower island 530 is bounded by the intermediate circumferential groove 522 and the lower circumferential groove 524. The circumferential grooves and the vertical grooves preferably have rounded or curved surfaces to minimize the presence of sharp edges coming in contact with a shell formed on the mandrel.

Figure 23A:
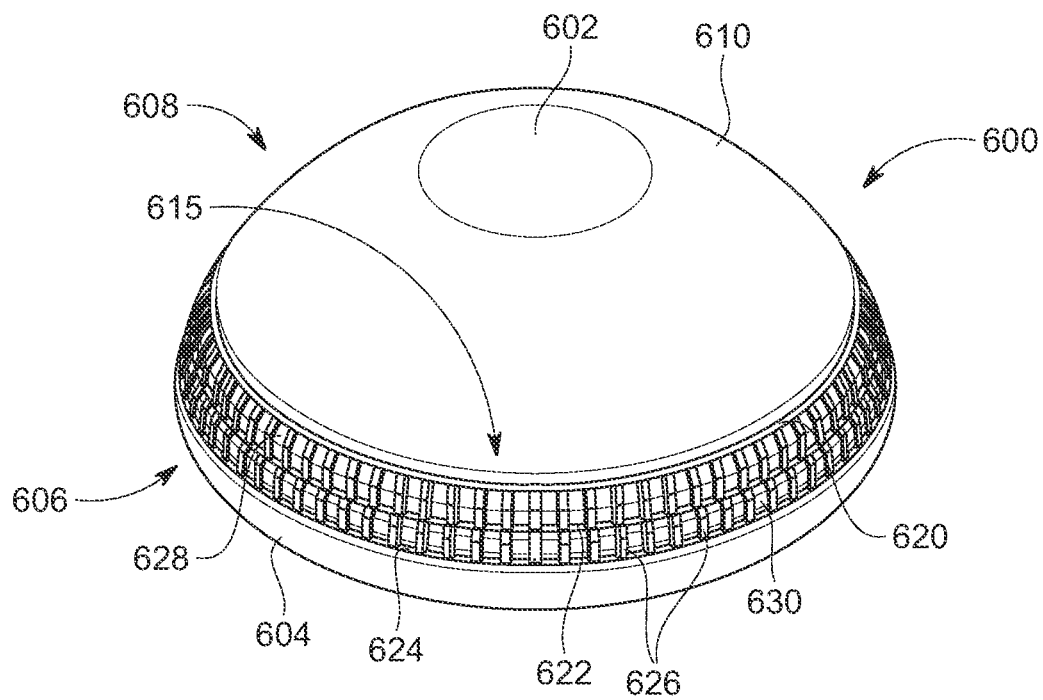
FIG. 23A shows a perspective view of a mandrel having a mesh shaped groove pattern formed in an outer surface thereof, in accordance with one embodiment of the present patent application.
Figure 23B:
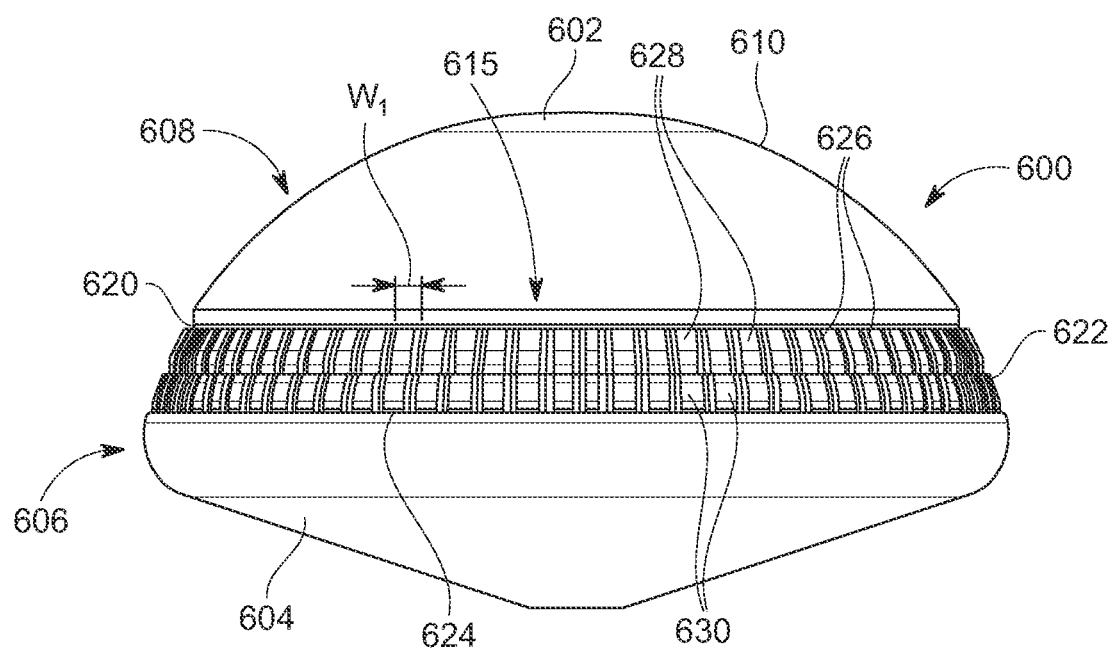
FIG. 23B shows a front elevation view of the mandrel shown in FIG. 23A.

Referring to FIGS. 23A and 23B, in one embodiment, a mandrel 600 for making shells used for mammary implants and tissue expanders preferably includes an apex 602 that defines an upper end of the mandrel, a base 604 that defines a lower end of the mandrel, a radius 606 that extends around the sides of the mandrel 600, and a dome 608 that extends from the apex 602 to the radius 606. In one embodiment, the apex 602 and the dome 608 of the mandrel 600 define an outer surface 610 of the mandrel having a convexly curved shape. In one embodiment, the mandrel 600 has a mesh shaped groove pattern 615 formed in the outer surface 610 thereof. The mesh shaped groove pattern 615 may be formed by removing material from the mandrel, adding material to the outer surface of the mandrel (e.g., 3D printing), or by using a mold to form the mandrel. The mesh shaped groove pattern 615 preferably extends around the circumference of the mandrel in the region of the radius 606 of the mandrel.

In one embodiment, the mesh shaped groove pattern 615 preferably includes an upper circumferential groove 620 that extends around the circumference of the mandrel, an intermediate circumferential groove 622 that extends around the circumference of the mandrel, and a lower circumferential groove 624 that extends around the circumference of the mandrel. In one embodiment, the intermediate circumferential groove is located between the upper circumferential groove and the lower circumferential groove. In one embodiment, the circumferential grooves 620, 622 and 624 may lie in respective planes that are parallel with one another. In one embodiment, the circumferential grooves 620, 622, and 622 desirably form bands that extend completely around the circumference of the mandrel.

In one embodiment, the mesh shaped groove pattern 615 preferably includes radial grooves 626 that extend from the upper circumferential groove 620, through the intermediate circumferential groove 622, and to the lower circumferential groove 624. The radial grooves 626 preferably extend in a radial direction (e.g., a vertical direction) that runs from the apex 602 to the base 604 of the mandrel 600. In one embodiment, the radial grooves 626 may be vertical grooves that are evenly spaced from one another around the circumference of the mandrel 600. The radial grooves 626 preferably intersect the circumferential grooves 620, 622 and 624 and cooperatively divide the mesh shaped groove pattern 615 into upper islands 628 located above the intermediate circumferential groove 622 and lower islands 630 located below the intermediate circumferential groove 622. The respective upper and lower islands 628, 630 preferably extend around the circumference of the mandrel. In one embodiment, the vertical grooves 626 are spaced from one another a distance $W_1$ of about 0.170 inches.

Figure 24:
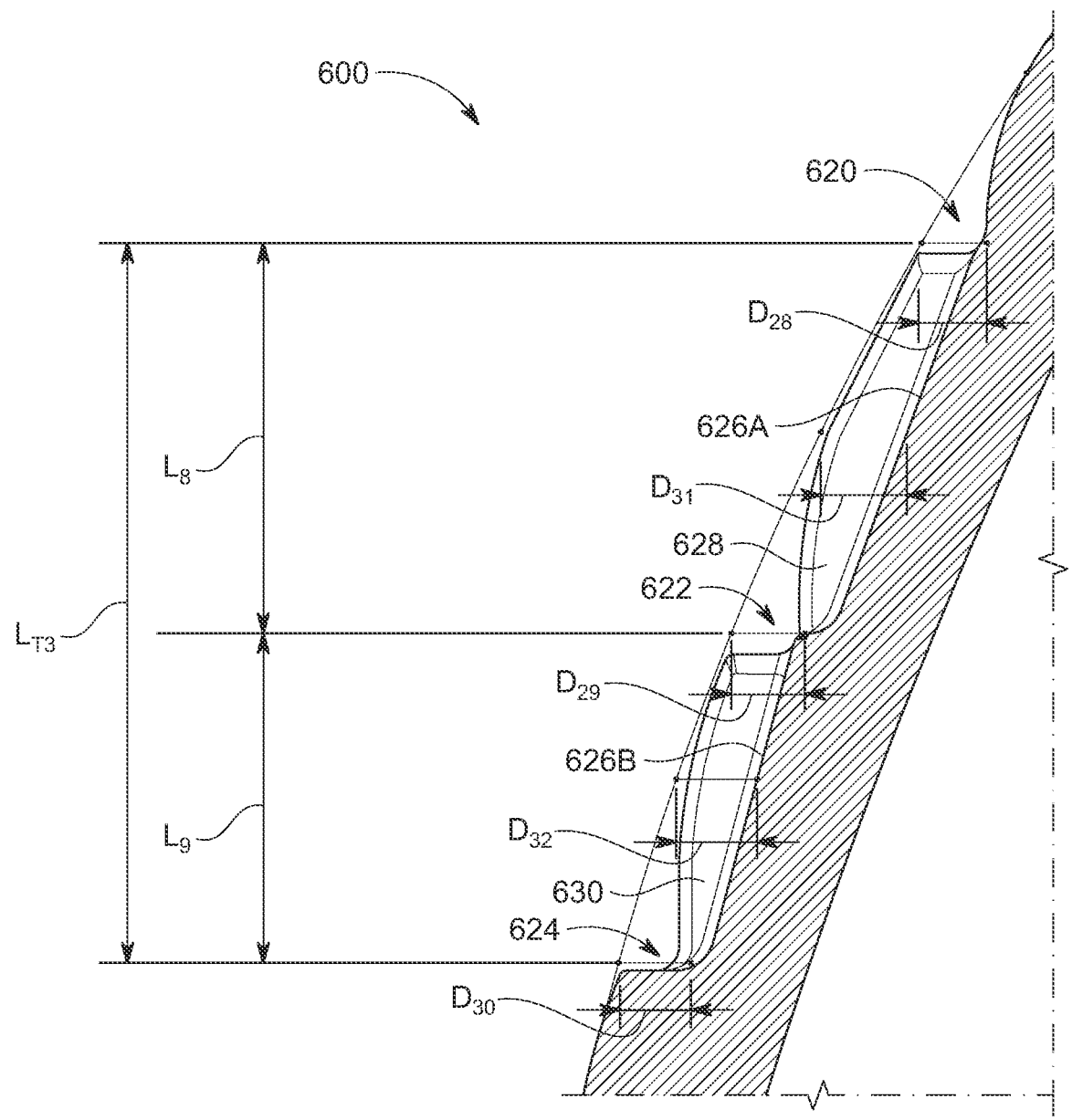
FIG. 24 shows a magnified view of a section of the mesh shaped groove pattern shown in FIGS. 23A and 23B.

Referring to FIG. 24, in one embodiment, the distance between the upper circumferential groove 620 and the intermediate circumferential groove 622 is $L_8$ or about 0.25 inches. In one embodiment, the distance between the intermediate circumferential groove 622 and the lower circumferential groove 624 is $L_9$ or about 0.20 inches. In one embodiment, the distance between the upper circumferential groove 620 and the lower circumferential groove 624 is $L_{T3}$ or about 0.45 inches.

In one embodiment, each of the circumferential grooves 620, 622, 624 is formed in the outer surface 610 of the mandrel 600. In one embodiment, the upper circumferential groove 620 has a depth $D_{28}$ of about 0.04 inches. In one embodiment, the intermediate circumferential groove 622 has a depth $D_{29}$ of about 0.045 inches. In one embodiment, the lower circumferential groove 624 has a depth $D_{30}$ of about 0.04 inches. In one embodiment, the vertically extending groove 626 (FIG. 23B) preferably extends along a slope. In one embodiment, the vertically extending groove desirably has an upper portion 626A that passes by the upper island 628 having a depth $D_{31}$ of about 0.053 inches and a lower portion 626B that passes by the lower island 630 having a depth $D_{32}$ of about 0.05 inches. The upper island 628 is bounded by the upper circumferential groove 620 and the intermediate circumferential groove 622. The lower island 630 is bounded by the intermediate circumferential groove 622 and the lower circumferential groove 624. The grooves are preferably rounded or have concave surfaces to minimize the presence of sharp edges, which may result in damage (e.g., tearing) to shells formed on the mandrel.

Figure 25:
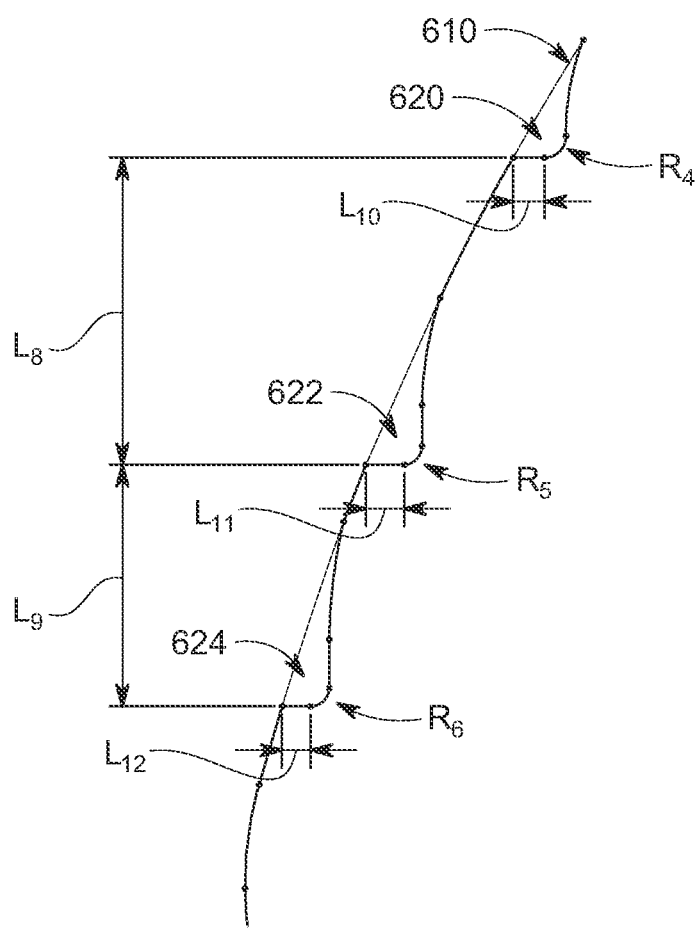
FIG. 25 shows a magnified side view of a portion of the mesh shaped groove pattern shown in FIGS. 23A-23B.

Referring to FIG. 25, in one embodiment, the upper circumferential groove 620 is cut into the outer surface 610 of the mandrel 600. The upper circumferential groove 620 has a first horizontal section (e.g., a flat surface) having a length $L_{10}$ of about 0.025 inches and a concave surface having a radius $R_4$ of about 0.015 inches. In one embodiment, the intermediate circumferential groove 622 has a first horizontal section (e.g., a flat surface) with a length $L_{11}$ of about 0.030 inches and a concave surface having a radius $R_5$ of about 0.015 inches. In one embodiment, the lower circumferential groove 624 has a first horizontal section (e.g., a flat surface) with a length $L_{12}$ of about 0.023 inches and a concave surface having a radius $R_6$ of about 0.015 inches. Providing concave surfaces on the circumferential grooves 620, 622, and 624 preferably minimizes damage to shells as the shells are peeled away from the mandrel. The distance between the base of the upper circumferential groove 620 and the base of the intermediate circumferential groove 622 is designated $L_8$ or about 0.25 inches. The distance between the base of the intermediate circumferential groove 622 and the lower circumferential groove 624 is designated $L_9$ or about 0.20 inches.

Figure 26A:
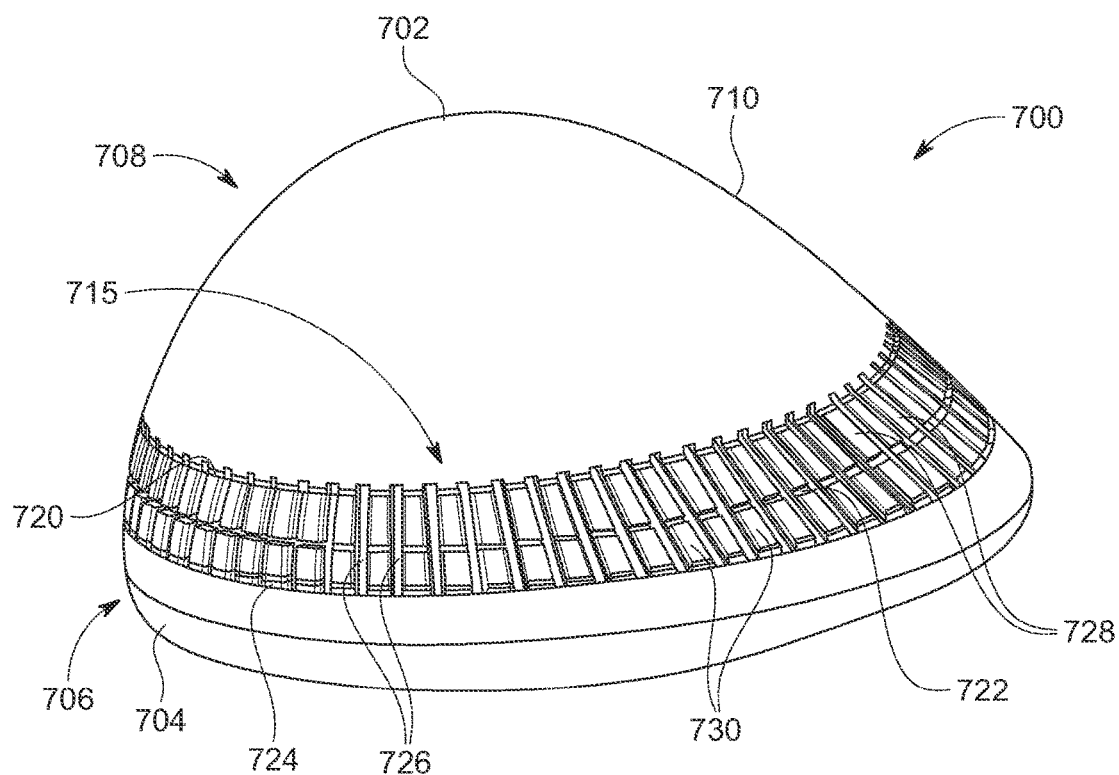
FIG. 26A shows a perspective view of a mandrel having an asymmetric base and a mesh shaped groove pattern formed in an outer surface thereof, in accordance with one embodiment of the present patent application.
Figure 26B:
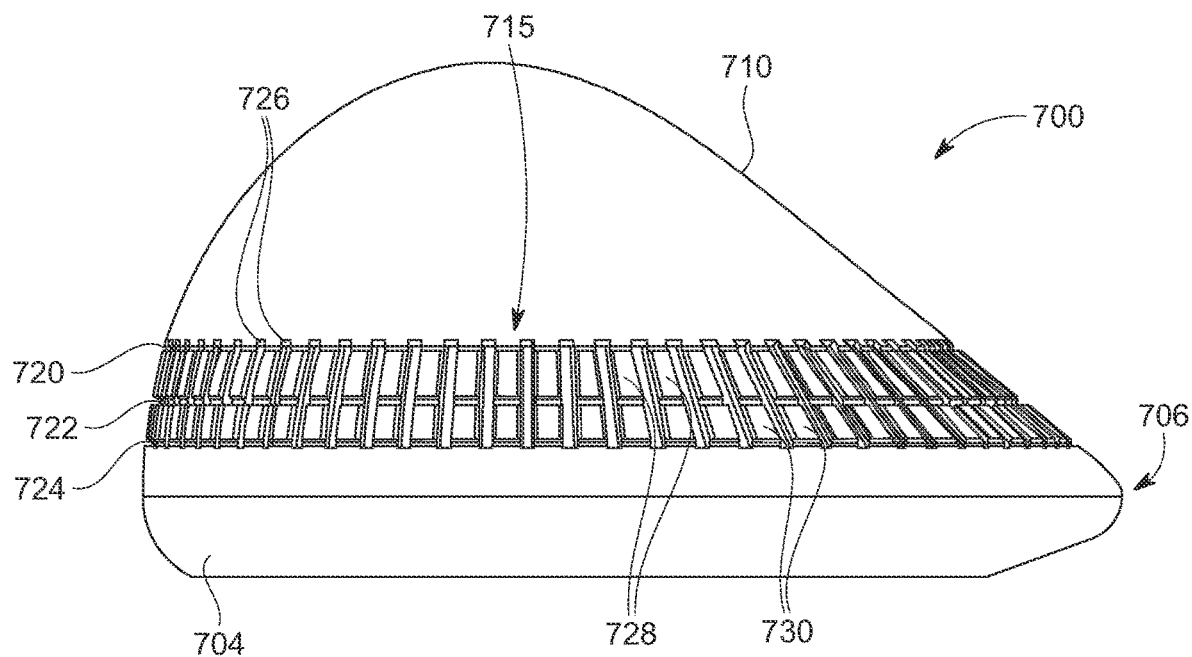
FIG. 26B shows a front elevation view of the mandrel shown in FIG. 26A.

Referring to FIGS. 26A and 26B, in one embodiment, a mandrel 700 has an apex 702, a base 704, a radius 706 that extends around the circumference thereof and a dome 708 that extends between the apex 702 and the base 704. In one embodiment, the base 704 and the radius 706 define an asymmetric or non-circular structure. In one embodiment, a mesh shaped groove pattern 715 is formed in the outer surface 710 of the mandrel. The mesh shaped groove structure 715 preferably includes an upper circumferential groove 720, an intermediate circumferential groove 722 and a lower circumferential groove 724. The circumferential grooves 720, 722 and 724 preferably extend around the circumference of the mandrel 700 at the radius region 706 thereof. In one embodiment, the mesh shaped groove pattern 715 preferably includes vertically extending grooves 726 that intersect with and extend across the respective upper circumferential groove 720, intermediate circumferential groove 722 and lower circumferential groove 724. The circumferential grooves 720, 722 and 724 and the vertically extending grooves 726 cooperatively form a square or rectangular lattice pattern including a band of upper islands 728 and a band of lower islands 730 that extend around the circumference of the mandrel. The circumferential grooves 720, 722 and 724 and the vertical grooves 726 may have the same spacing and/or dimensions as those described above for the mandrels shown in FIGS. 14A-25.

The mandrel 700 shown in FIGS. 26A and 26B may be used to form a shell having an asymmetric base. The shell may include a mesh shaped rib pattern that projects inwardly from an inner surface of the shell. The mesh shaped rib pattern preferably mirrors the mesh shaped groove pattern 715 formed in the outer surface 710 of the mandrel 700 (FIG. 26B).

Figure 27A:
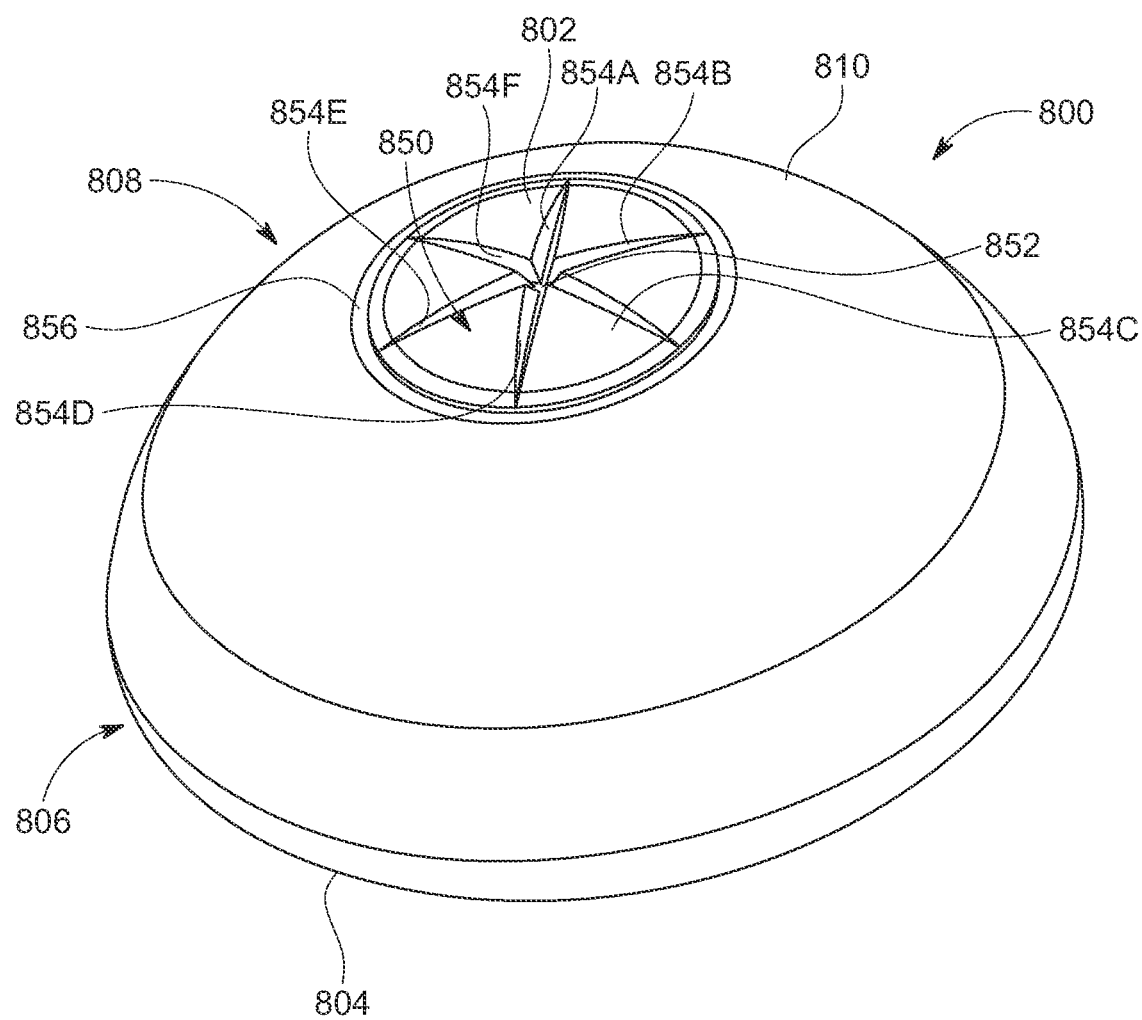
FIG. 27A shows a perspective view of a mandrel having a star-shaped groove pattern that is surrounded by a circular groove, in accordance with one embodiment of the present patent application.
Figure 27B:
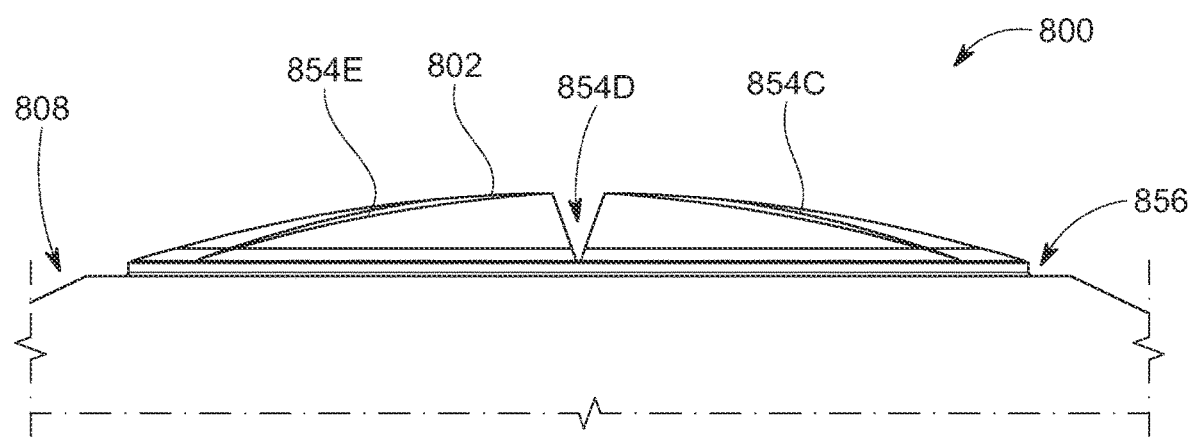
FIG. 27B shows a partial cross-sectional view of the mandrel of FIG. 27A.
Figure 27C:
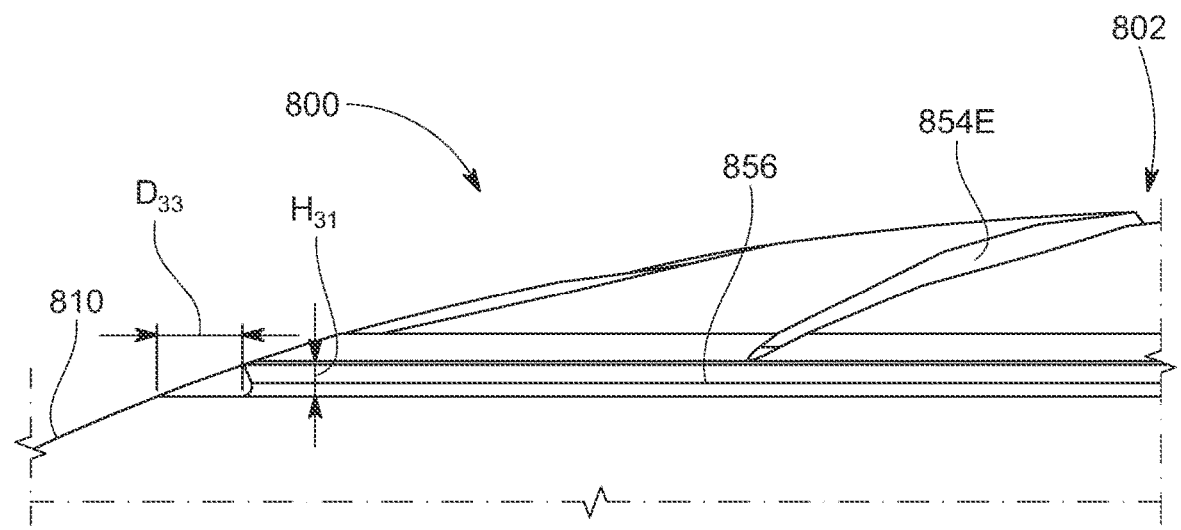
FIG. 27C shows a magnified view of a portion of the mandrel shown in FIG. 27B.

Referring to FIGS. 27A-27C, in one embodiment, a mandrel 800 utilized to make a shell for a mammary implant or tissue expander preferably includes an apex 802, a base 804 (FIG. 27A), a radius 806 (FIG. 27A) that extends around the circumference of the mandrel, and a dome 808 that extends between the apex 802 and the radius 806. In one embodiment, the apex and the dome of the mandrel 800 form a convexly curved outer surface 810. In one embodiment, a star-shaped groove pattern 850 is formed in the apex 802 of the mandrel 800. In one embodiment, the star-shaped groove pattern 850 preferably has a center 852 and six radially extending grooves 854A-854F that extend outwardly from the center 852. A circular groove 856 is preferably formed in the outer surface 810 of the mandrel 800 and surrounds the outer ends of the radially extending grooves 854A-854E of the star-shaped groove pattern 850.

Referring to FIG. 27C, in one embodiment, the circular groove 856 has a height $H_{31}$ of about 0.025 inches and a depth $D_{33}$ of about 0.071 inches. In one embodiment, the depth $D_{33}$ of the circular groove 856 is measured from the convexly curved outer surface 810 of the mandrel 800.

Figure 28:
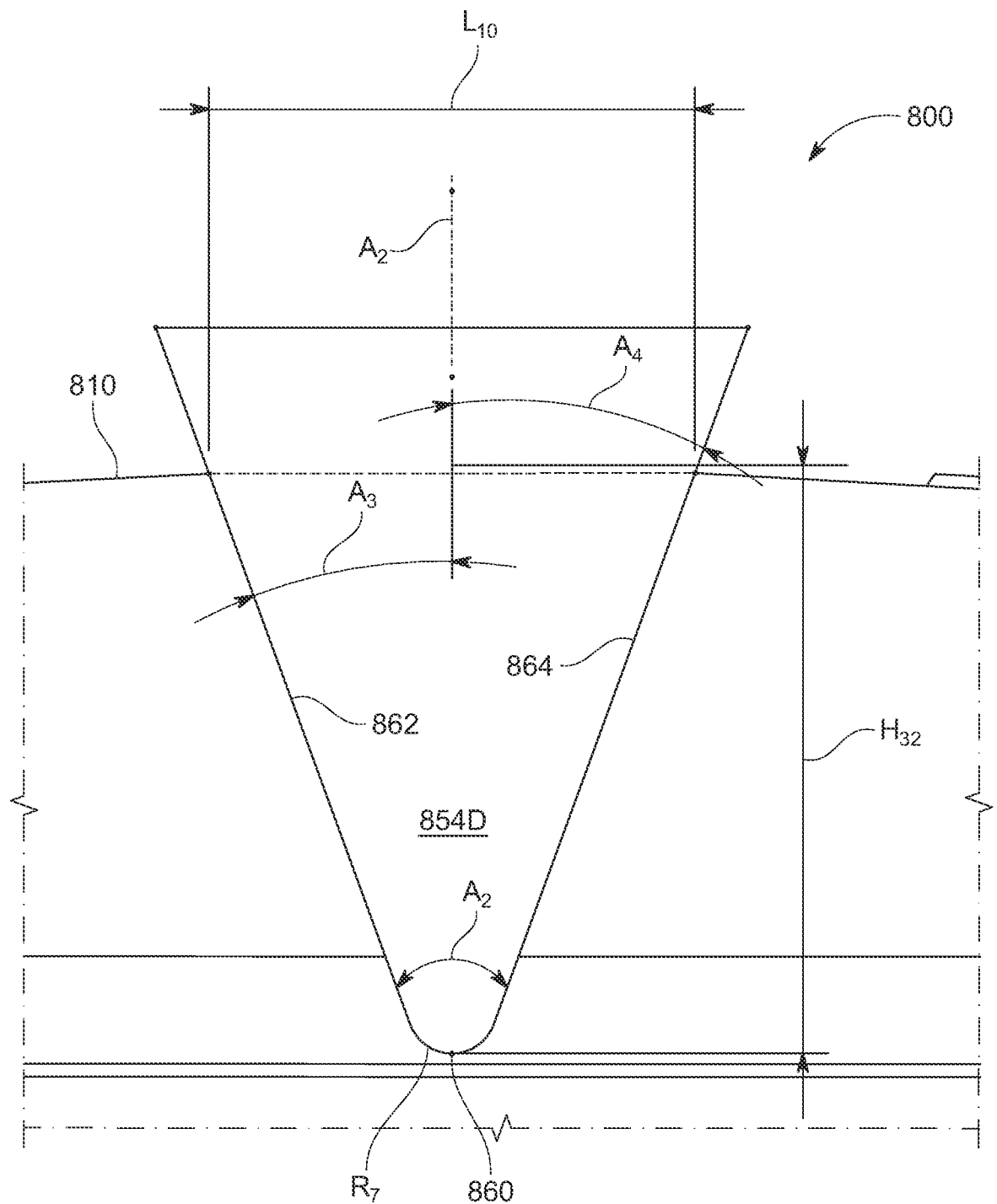
FIG. 28 shows a schematic cross-sectional view of one of the legs of the star-shaped groove pattern of FIGS. 27A-27C, in accordance with one embodiment of the present patent application.

Referring to FIG. 28, in one embodiment, a radially extending groove 854D is cut into the outer surface 810 of the mandrel 800. The radially extending groove 854D has a height $H_{32}$ of about 0.125 inches. The lower end of the groove 854D defines a curved surface 860 having a radius $R_7$ of about 0.010 inches. The radial groove 854D has opposing sloping walls 862, 864 that define an angle $\alpha_2$ of about 40°. In one embodiment, the first sloping wall 862 slopes away from a vertical axis $A_2$ at an angle $\alpha_3$ of about 20°. Similarly, the second sloping wall 864 slopes away from the vertical axis $A_2$ at angle $\alpha_4$ of about 20°. At the upper ends of the sloping walls 862, 864 where the walls intersect with the outer surface 810 of the mandrel 800, the distance $L_{10}$ is about 0.102 inches.

Figure 29A:
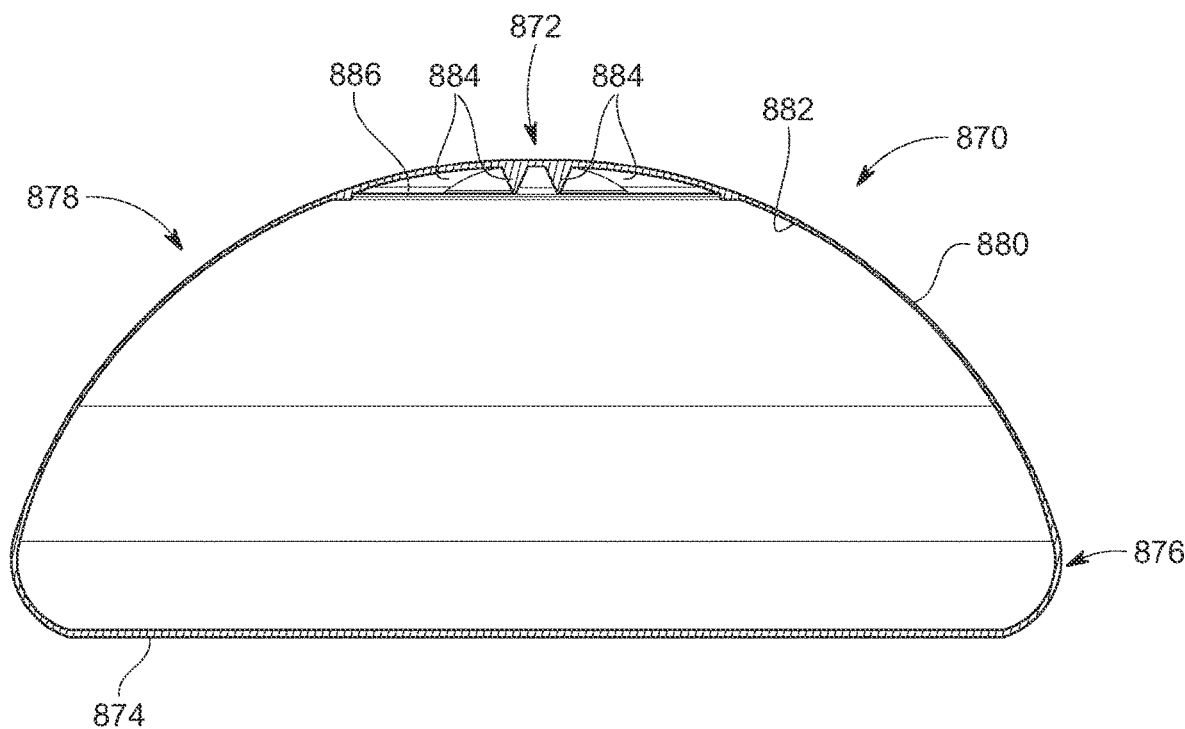
FIG. 29A shows a cross-sectional view of a shell having star-shaped ribs and a circular rib that is made using the mandrel of FIGS. 27A-27C and 28, in accordance with one embodiment of the present patent application.
Figure 29B:
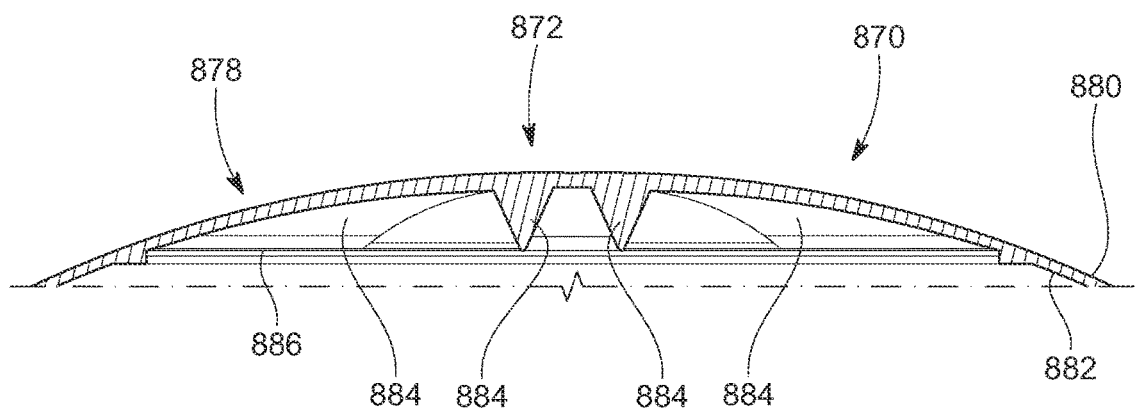
FIG. 29B shows a magnified, partial cross-sectional view of the shell of FIG. 29A.

Referring to FIGS. 29A and 29B, in one embodiment, the mandrel shown and described above in FIGS. 27A-27C and 28 may be utilized to form a shell 870 having an inwardly projecting star-shaped rib 884 that is surrounded by an inwardly projecting circular rib 886. In one embodiment, the shell 870 preferably includes an apex 872, a base 874, a radius 876 (FIG. 29A) that extends around the circumference of the shell, and a dome region 878 that extends from the apex 872 to the radius 876 (FIG. 29A). In one embodiment, the shell 870 preferably includes an outer surface 880 and an inner surface 882 that defines an interior volume of the shell. In one embodiment, the shell 870 preferably includes star-shaped ribs 884 that project inwardly from the inner surface 882 of the shell 870 at the apex 872 and a circular rib 886 that projects inwardly from the inner surface 882 of the shell 870 and that surrounds the outer ends of the star-shaped ribs 884. In one embodiment, the star-shaped ribs 884 mirror and have the same size, shape and dimension as the star-shaped grooves 854A-854F shown and described above in FIGS. 27A-27C and 28. Similarly, the circular rib 886 mirrors and has the same size, shape and dimension as the circular groove 856 shown and described above in FIGS. 27A-27C and 28. The star-shaped ribs 884 and the circular rib 886 preferably improve the structural integrity of the shell 870 and enhance projection at the apex 872 of the shell 870.

Figure 30A:
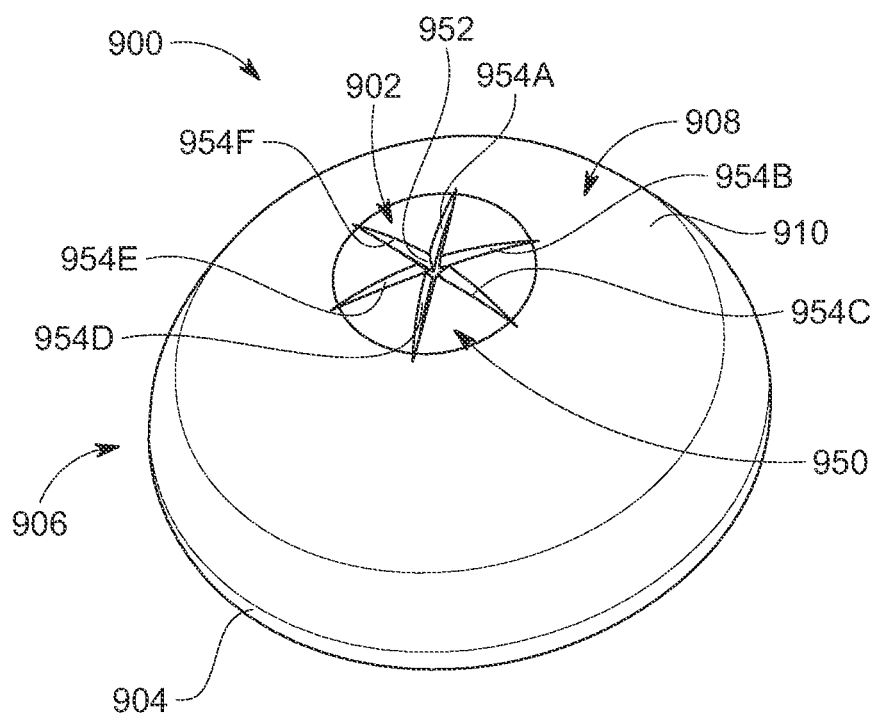
FIG. 30A shows a perspective view of a mandrel having a star-shaped groove pattern, in accordance with one embodiment of the present patent application.
Figure 30B:
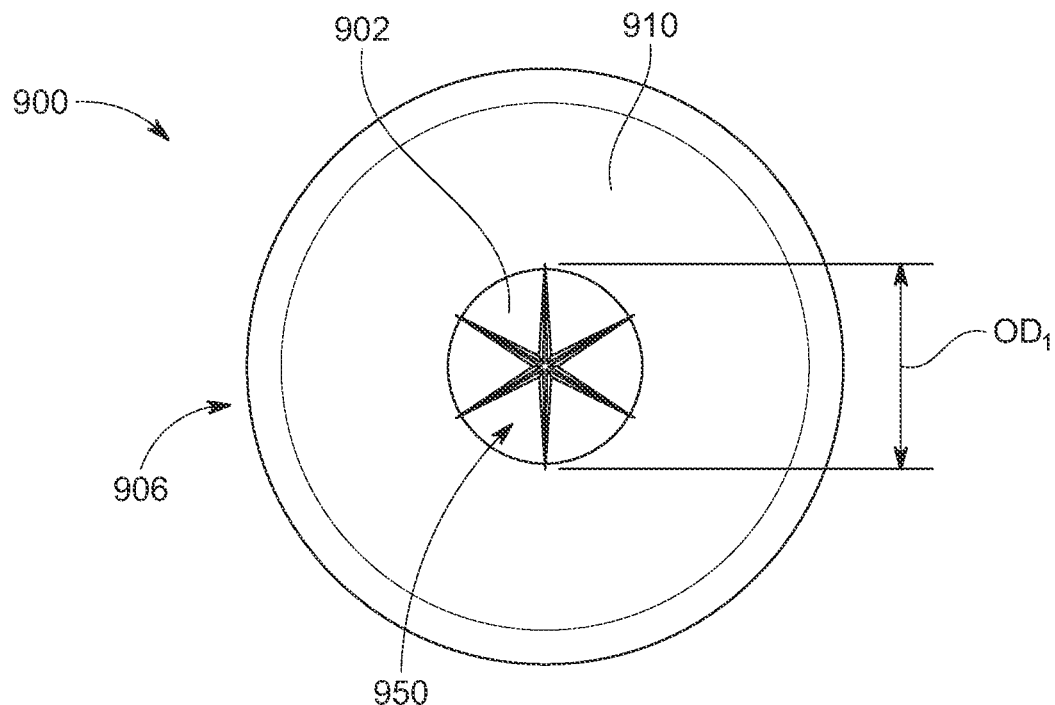
FIG. 30B shows a top plan view of the mandrel of FIG. 30A.

Referring to FIGS. 30A and 30B, in one embodiment, a mandrel 900 that is utilized to make a shell for a mammary implant or tissue expander preferably includes an apex 902, a base 904, a radius 906 that extends around the circumference of the mandrel, and a dome 908 that extends between the apex 902 and the radius 906. In one embodiment, the apex and the dome of the mandrel 900 form a convexly curved outer surface 910. In one embodiment, a star-shaped groove pattern 950 is formed in the apex 902 of the mandrel 900. In one embodiment, the star-shaped groove pattern 950 preferably has a center 952 and six radially extending grooves 954A-954F that extend outwardly from the center 952. The star-shaped groove pattern has an outer diameter $OD_1$ of about 1.25-1.75 inches and more preferably about 1.64 inches.

In one embodiment, the mandrel shown and described above in FIGS. 30A and 30B may be utilized to form a shell having inwardly projecting star-shaped ribs. In one embodiment, the shell preferably includes an outer surface and an inner surface that defines an interior volume of the shell. In one embodiment, the shell preferably includes star-shaped ribs that project inwardly at the apex. In one embodiment, the star-shaped ribs mirror and have the same size, shape and dimension as the star-shaped grooves 854A-854F shown and described above in FIGS. 30A and 30B.

Figure 31:
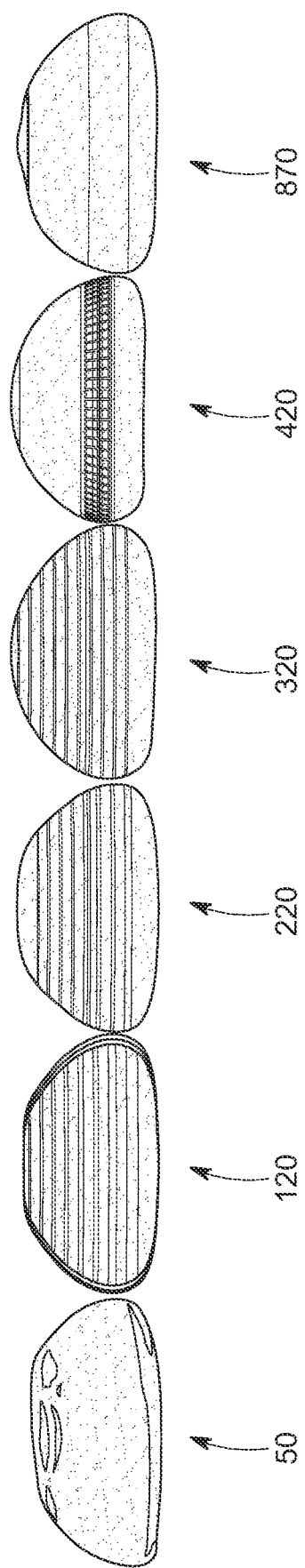
FIG. 31 shows a side view of a series of implants including a conventional implant, an implant having a shell with constant depth ribs of 0.05 inches, an implant having a shell with constant depth ribs of 0.025 inches, an implant having a shell with constant height ribs, an implant having a shell with a mesh shaped rib pattern, and an implant having a shell with a star-shaped rib pattern.

FIG. 31 shows a series of implants having shells filed with a gel. A first implant 50 (FIG. 1) has concavities 60 at the apex, which results in the undesirable ashtray effect. A second implant 120 (FIGS. 7A and 7B) has circumferential ribs having a constant depth of about 0.05 inches. A third implant 220 (FIGS. 10A and 10B) has circumferential ribs having a constant depth of about 0.025 inches. A fourth implant 320 (FIGS. 13A and 13B) has circumferential ribs having a constant height. A fifth implant 420 (FIGS. 18A and 18B) has a mesh shaped rib pattern with ribs that project inwardly from an inner surface of the shell. A sixth implant 870 (FIGS. 29A and 29B) has star-shaped ribs and a circular rib that surrounds the star-shaped ribs. As shown in FIG. 31, the implants with ribs formed in the shell (i.e., implants 120, 220, 320, 420, 870) provide a greater projection at the apex of the shell than the implant 50 that does not have ribs formed therein.

Figure 4:
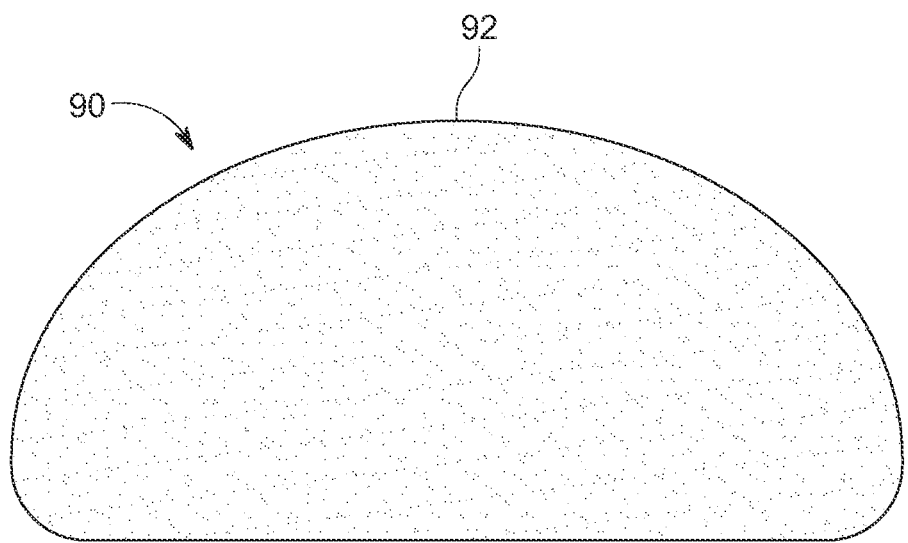
FIG. 4 shows a prior art implant having additional gel inserted into the shell to increase the projection at the apex of the shell.

FIGS. 32A and 32B show a series of implants having shells filed with a gel. A first implant 50 (FIG. 1) has concavities 60 at the apex, which results in the undesirable ashtray effect. A second implant 420 (FIGS. 18A and 18B) has a mesh shaped rib pattern with ribs that project inwardly from an inner surface of the shell. A third implant 90 (FIG. 4) has an additional 65 cc of gel inserted into the shell, which adds extra weight to the implant. The second implant 420 with the mesh ribbed design is preferred because it provides the desired projection that the first implant 50 lacks while avoiding the excess weight found in the third implant 90.

It is desirable for mammary implants to be soft and maintain a natural look and feel. Gel filled implants are generally softer than saline filled implants. Mammary implants are often tested to evaluate softness levels.

Figure 33:
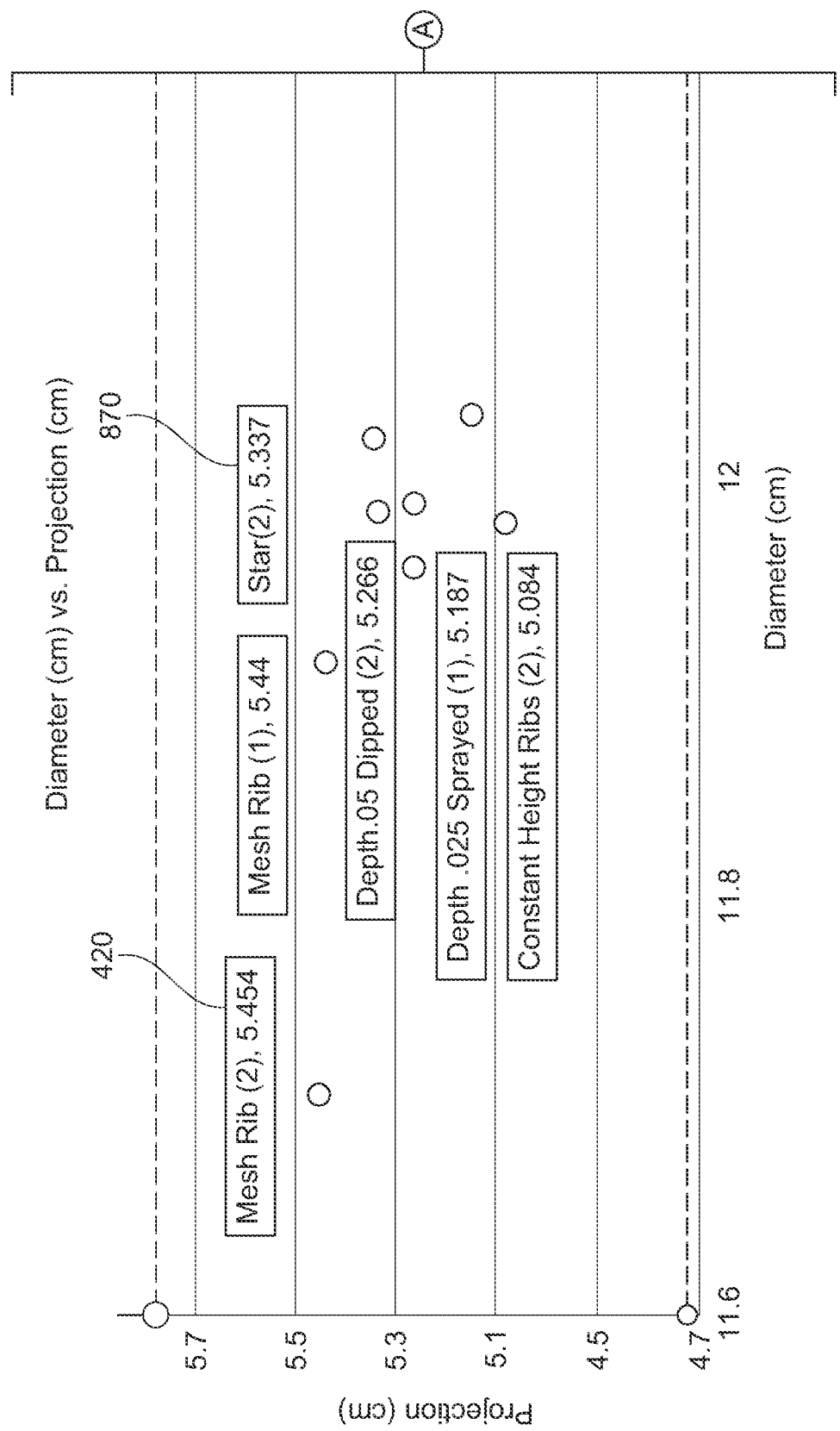
FIG. 33 is a chart plotting the diameters and projections of implant shells having various designs.
Figure 33:
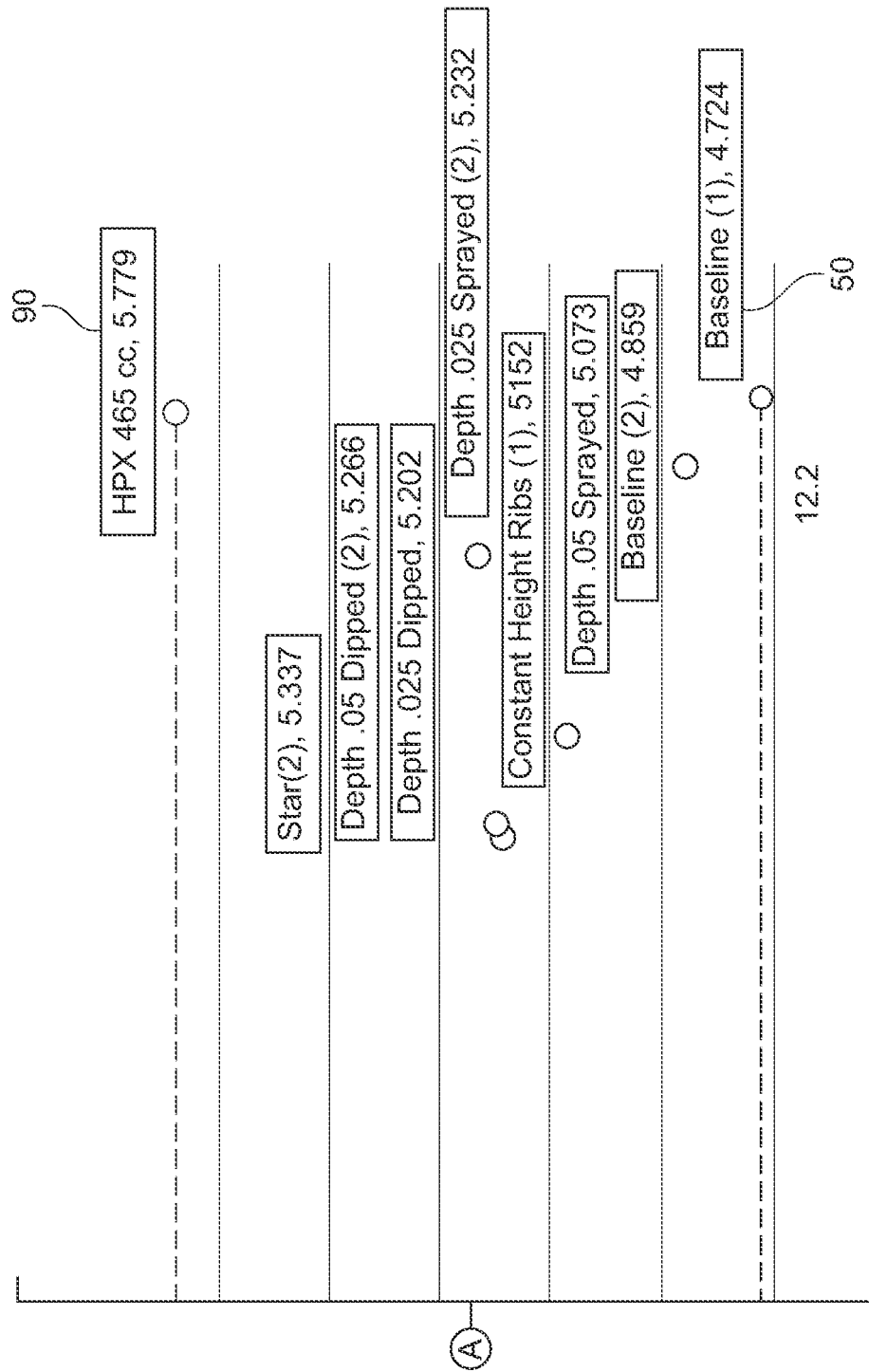

Referring to FIG. 33, in one embodiment, when compared to the baseline design 50 (FIG. 1) the mesh ribbed design provided the greatest positive change in the projection and the diameter of the implant. The projection of the mesh ribbed design increased by +7.3 mm compared to the baseline design. The outer diameter of the mesh ribbed design decreased by −5.36 mm compared to the baseline design.

Figure 34:
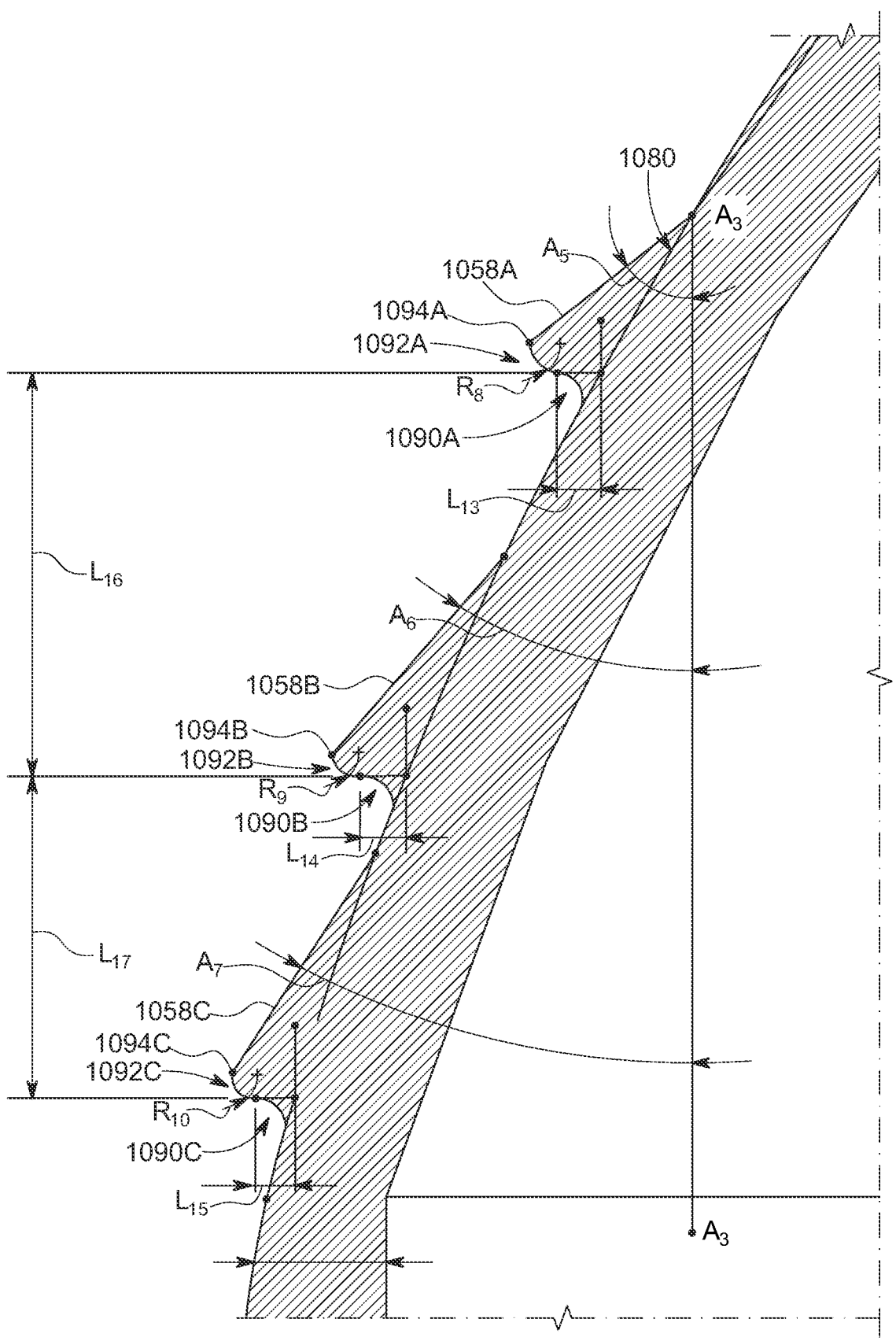
FIG. 34 shows a partial cross-sectional view of a shell having externally projecting ribs, in accordance with one embodiment of the present patent application.

Referring to FIG. 34, in one embodiment, a shell 1070 preferably has external ribs 1058A-1058C projecting from an outer surface 1080 thereof. The external ribs may be provided on any of the shells disclosed herein having internal ribs that project from an inner surface of a shell.

In one embodiment, a first external rib 1058A has a topside surface that projects away from an axis $A_3$ at an angle $\alpha_5$ of about 52 degrees. The first external rib 1058A preferably includes an underside surface having a concave section 1090A, extending away from the outer surface 1080 of the shell, having a length $L_{13}$ of about 0.025 inches, which transforms to a convex section 1092A, adjacent a tip 1094A of the rib 1058A, having a radius $R_8$ of about 0.018 inches. In one embodiment, a second external rib 1058B has a topside surface that projects away from an axis $A_3$ at an angle $\alpha_6$ of about 41 degrees. The second external rib 1058B preferably includes an underside surface having a concave section 1090B, extending away from the outer surface 1080 of the shell, having a length $L_{14}$ of about 0.030 inches that transforms to a convex section 1092B, adjacent a tip 1094B of the rib 1058B, having a radius $R_9$ of about 0.015 inches. In one embodiment, a third external rib 1058C has a topside surface that projects away from an axis $A_3$ at an angle $\alpha_7$ of about 33 degrees. The third external rib 1058C preferably includes an underside surface having a concave section 1090C, extending away from the outer surface 1080 of the shell, having a length $L_{15}$ of about 0.023 inches that transforms to a convex section 1092C, adjacent a tip 1094C of the rib 1058C, having a radius $R_{10}$ of about 0.016 inches. In one embodiment, the spacing $L_{16}$ between the tip 1094A of the first external rib 1058A and the tip 1094B of the second external rib 1058B is about 0.253 inches. In one embodiment, the spacing $L_{17}$ between the tip 1094B of the second external rib 1058B and the tip 1094C of the third external rib 1058C is about 0.20 inches.

Figure 35:
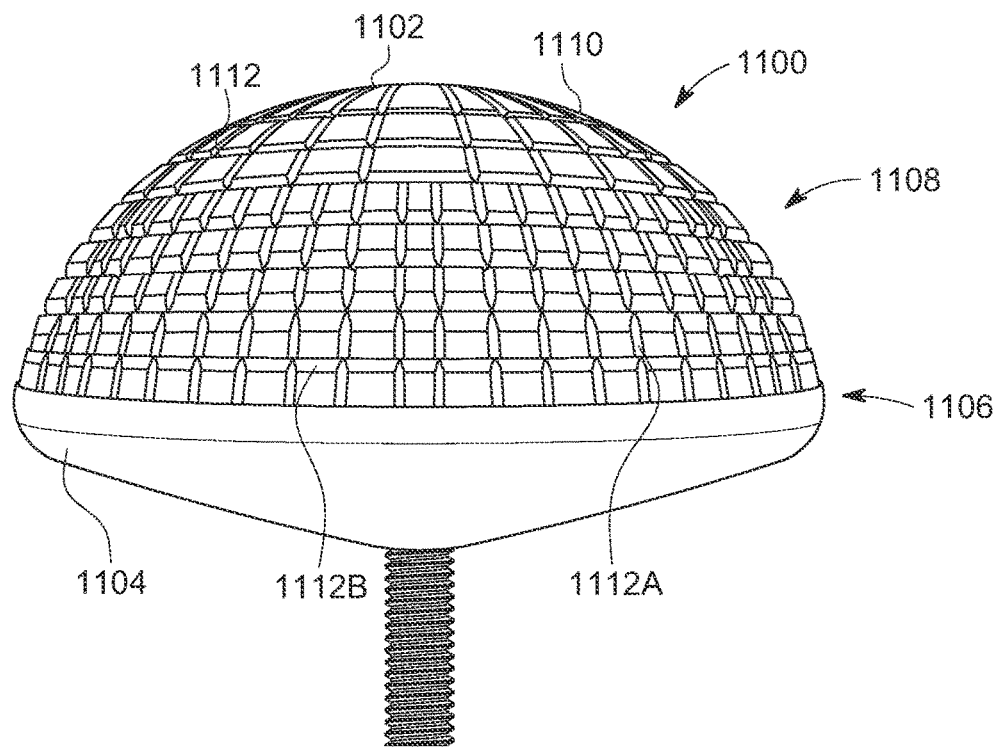
FIG. 35 is a front elevation view of a mandrel having grooves formed in an outer surface, in accordance with one embodiment of the present patent application.

Referring to FIG. 35, in one embodiment, a mandrel 1100 is configured for making a shell having integral ribs that extend inwardly from an inner surface of the shell. The mandrel 1100 desirably includes an apex 1102 located at an upper end of the mandrel, a base 1104 located at a lower end of the mandrel, a radius 1106 that extends around the circumference of the mandrel 1100, and a dome 1108 having a convexly curved outer surface 1110 that extends between the apex 1102 and the base 1104. In FIG. 35, the mandrel 1100 is in an upright configuration.

In one embodiment, the mandrel 1100 preferably has a plurality of spaced grooves 1112 that are formed in the convexly curved outer surface 1110 of the mandrel 1100. The grooves 1112 may extend in any direction over the convexly curved surface of the mandrel (e.g., horizontally, vertically, diagonally, radially).

In one embodiment, the grooves 1112 may include radially extending grooves 1112A that extend between the apex 1102 and the base 1104 of the mandrel 1100. In one embodiment, the grooves may include circumferential grooves 1112B that extend around the circumference of the mandrel 1100. In one embodiment, the grooves 1112 may be formed by removing material from the convexly curved outer surface 1110 of the mandrel 1100. In one embodiment, the grooves 1112 may be formed by adding material to the convexly curved outer surface 1110 of the mandrel, such as by using 3D printing techniques.

In one embodiment, the outer surface of the mandrel may be machined for forming the convexly curved outer surface 1110 and/or the grooves 1112. In one embodiment, the mandrel 1100 may be made of materials such as polymers (e.g., Ertalyte), metal, wood, stone, and ceramic.

In one embodiment, a shell for use as an implant may be formed by depositing (e.g., spraying, dipping) a biocompatible curable material over the convexly curved outer surface 1110 of the mandrel 1100. In one embodiment, the curable material that is applied over the convexly curved outer surface 1110 of the mandrel may be a curable silicone material. In one embodiment, the curable silicone material may be sprayed over the convexly curved outer surface 1110 of the mandrel 1100, whereupon the curable material flows over the convexly curved surface and into the grooves 1112 formed in the convexly curved outer surface. In one embodiment, the curable silicone material may be applied over the convexly curved outer surface 1110 by dipping the mandrel in a curable silicone solution. In one embodiment, the shell may have multiple layers that are built up over the convexly curved outer surface of the mandrel using multiple spraying and/or dipping steps, whereby multiple layers of the curable material are deposited for increasing the wall thickness of shell. In one embodiment, prior to spraying a curable solution or dipping the mandrel in a curable solution, the grooves 1112 formed in the convexly curved outer surface 1110 of the mandrel 1100 may be prefilled with a material utilized for forming ribs (e.g., uncured, partially cured or cured silicone; a web of cured silicone) followed by one or more of the spraying and/or dipping steps described herein. In one embodiment, the rib forming material that is pre-filled into the grooves of the mandrel may be made of a different material than the material utilized for making the implant shell. In one embodiment, the rib forming material that is pre-filled into the grooves may include suture or wire material.

In one embodiment, a shell may be made using one or more of the systems, devices and methods disclosed in U.S. Pat. No. 4,472,226 to Redinger et al. or U.S. Patent Application Publication No. US 2014/0088703 to Schuessler, the disclosures of which are hereby incorporated by reference herein.

Figure 36:
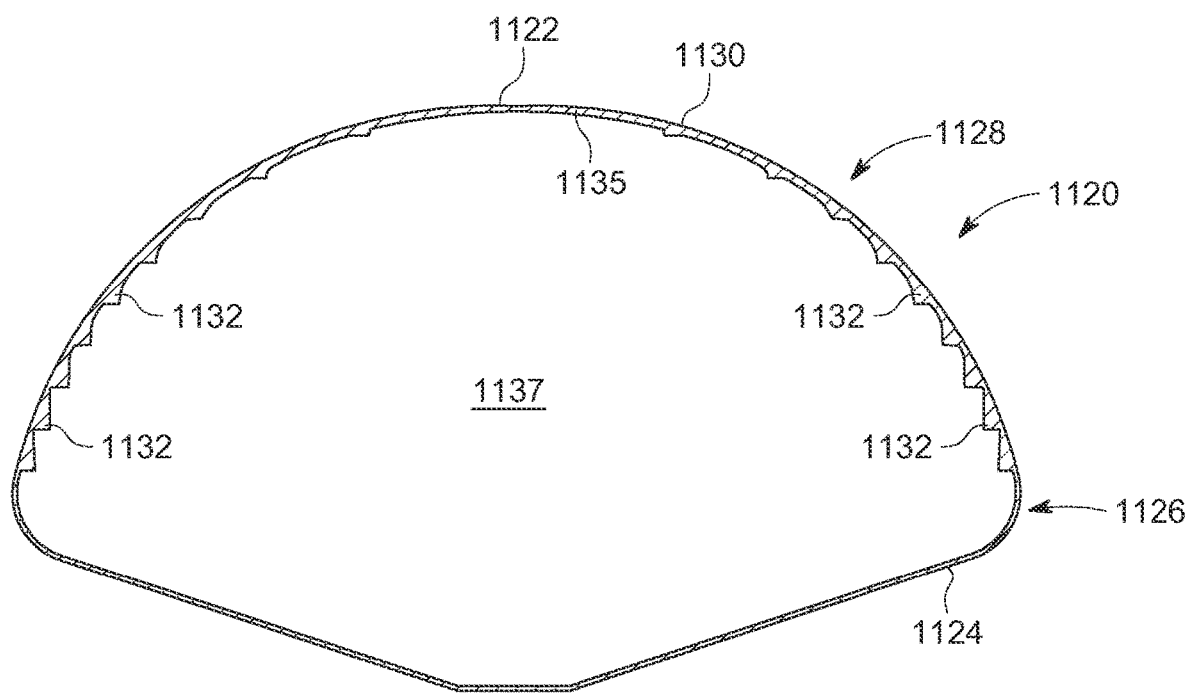
FIG. 36 shows a cross-sectional view of a shell that is manufactured using the mandrel having grooves of FIG. 35.

Referring to FIG. 36, in one embodiment, a shell 1120 for an implant (e.g., a mammary implant, a tissue expander) may be formed using the mandrel 1100 having the grooved convex surface that is shown and described above in FIG. 35. In one embodiment, the shell 1120 may be formed on the convexly curved outer surface 1110 of the mandrel 1100 (FIG. 35). In one embodiment, the shell 1120 preferably includes an apex 1122, a base 1124, a radius 1126 that extends around the circumference or side of the implant shell 1120, and a dome 1128 that extends from the apex 1122 to the radius 1126 of the shell 1120.

In one embodiment, the shell 1120 desirably has a convexly curved outer surface 1130 and a concave curved inner surface 1135 that surrounds an interior volume 1137 of the shell 1120. In one embodiment, the interior volume 1137 of the shell 1120 is preferably filled with a gel or saline solution. In one embodiment, the shell 1120 desirably includes integral ribs 1132 that project inwardly from the inner surface 1135 of the shell 1120. In one embodiment, the ribs 1132 are desirably mirror images of the grooves 1112 provided on the convexly curved outer surface of the mandrel 1100 shown and described above in FIG. 35. The ribs 1132 preferably have dimensions and a configuration that match the dimensions and the configuration of the grooves 1112 provided on the mandrel 1100 (FIG. 35). The ribs are located inside the shell and preferably extend inwardly from the inner surface of the wall of the shell. In one embodiment, at least one of the ribs is integrally formed with and extends over the dome of the shell.

Figure 37A:
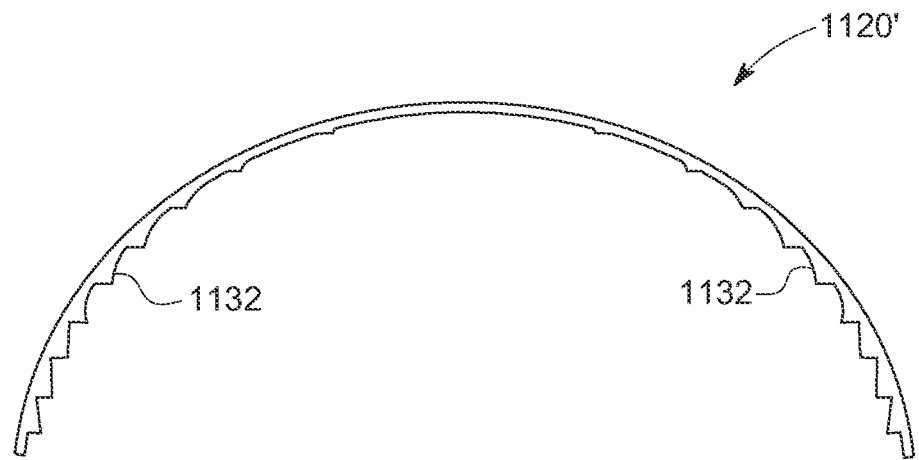
FIG. 37A illustrates a first stage of a method of making a shell having inwardly projecting ribs, in accordance with one embodiment of the present patent application.

Referring to FIG. 37A, in one embodiment, curable silicone material is deposited over the convexly curved outer surface 1110 of the mandrel 1100 shown and described above in FIG. 35. Initially, a shell precursor 1120' is built up over the convexly curved outer surface of the mandrel by depositing the curable silicone material over the outer surface of the mandrel. As the curable material is deposited over the convexly curved outer surface of the mandrel, some of the curable material flows into the grooves of the mandrel to define the integral ribs 1132 of the shell. The curable silicone material may be deposited in layers to build up the wall thickness of the shell precursor 1120'. In one embodiment, the shell precursor 1120' has a wall thickness that is thinner than the final wall thickness of a shell that may be used as an implant (e.g., a mammary implant, a tissue expander). In one embodiment, the layers may be built up using a spraying technique, a dipping technique, or a combination of both spraying and dipping for applying multiple layers over the convexly curved outer surface of the mandrel 1100 (FIG. 35).

Figure 37B:
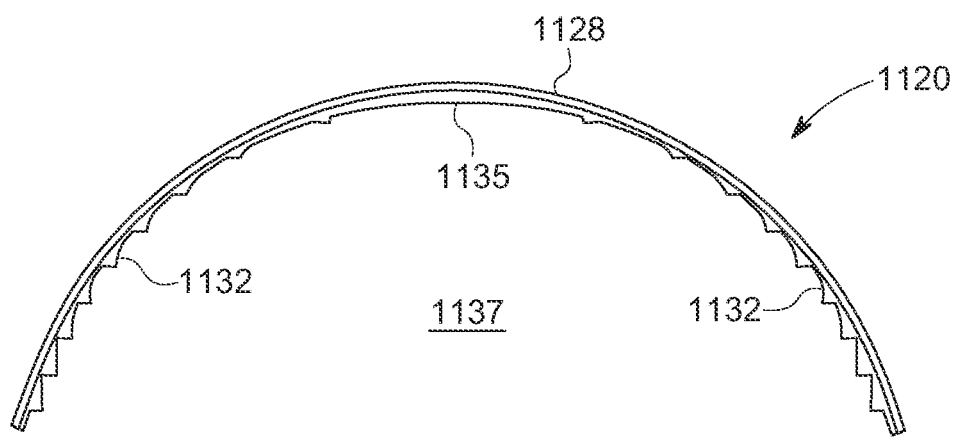
FIG. 37B shows a second stage of a method of making a shell having inwardly projecting ribs, in accordance with one embodiment of the present patent application.

Referring to FIG. 37B, in one embodiment, after additional layers of the curable silicone material are applied over the shell precursor 1120' shown in FIG. 37A, the wall thickness of the shell 1120 is greater than the initial wall thickness of the shell precursor 1120'. The shell 1120 desirably includes an outer surface 1128 that is smooth and an inner surface 1135 that has integral ribs 1132 that are located inside the shell and that extend inwardly from the inner surface 1135 and into the interior volume 1137 of the implant shell 1120. The shape, configuration, and pattern of the inwardly extending ribs 1132 preferably match the groove pattern provided on the mandrel 1100 shown and described above in FIG. 35.

In one embodiment, a shell forming material (e.g., uncured silicone, partially cured silicone) may be applied to the convexly curved outer surface of the grooved convex mandrel (FIG. 35) to form the ribbed shell. The shell forming material may be applied in multiple layers. For example, a first layer of shell forming material may be applied to an outer surface of the grooved convex mandrel followed by at least partial curing the first layer, followed by applying a second layer of shell forming material over the first layer. The process may be repeated to apply multiple layers of shell forming material over the mandrel for making a shell implant. The shell forming material may be applied to the convex grooved mandrel using spraying techniques, dipping techniques, and combinations of spraying and dipping techniques. In one embodiment, the grooves 1112 (FIG. 35) of the grooved convex mandrel may be pre-filled with a material used to make ribs (e.g., uncured, partially cured, or fully cured silicone gel), followed by one or more of the spraying and/or dipping steps disclosed herein. In one embodiment, the ribs may be made of a different material (e.g., suture, wire) than the material used to make the shells.

Figure 38:
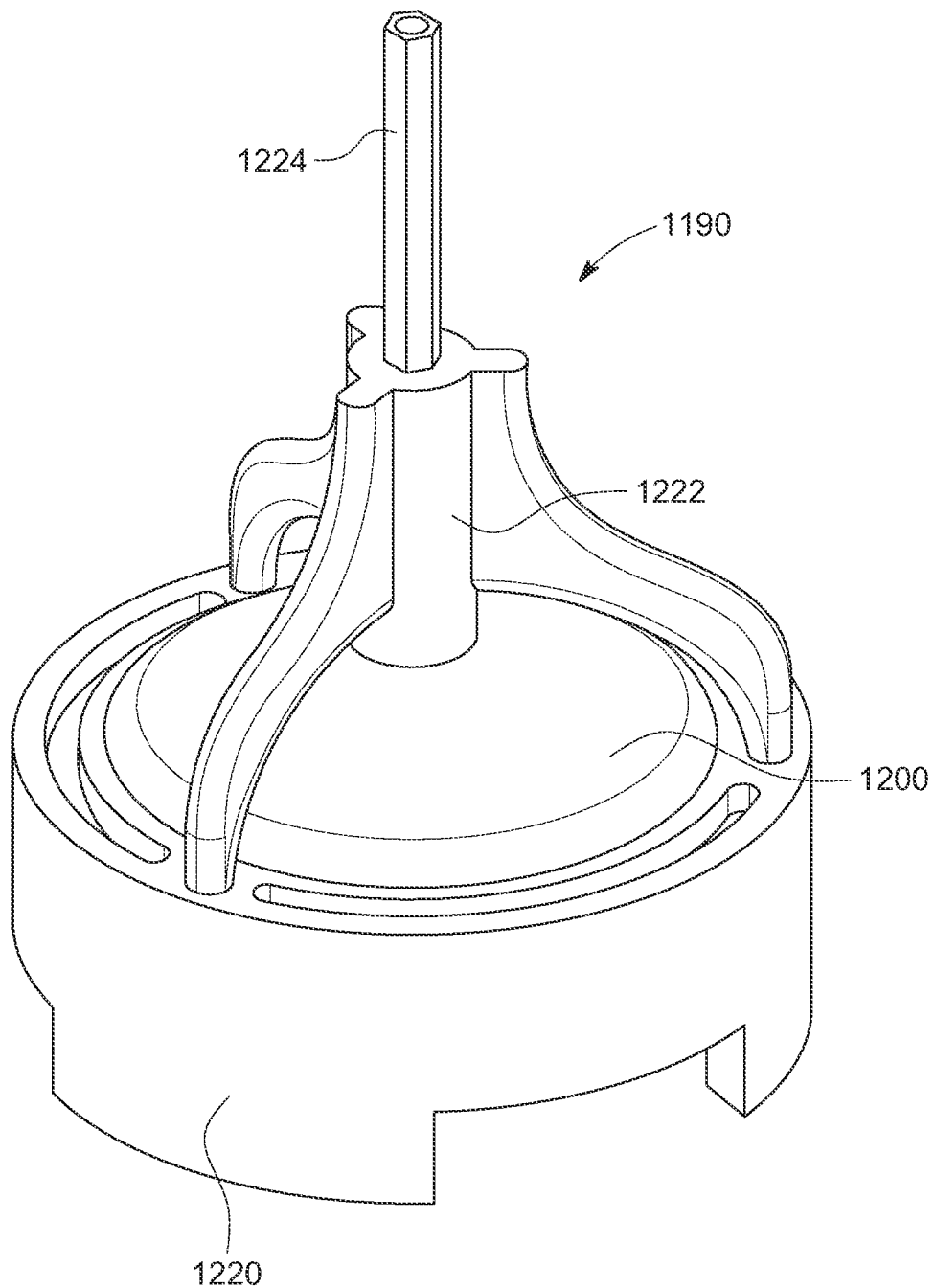
FIG. 38 shows a perspective view of a shell molding system including a mold having a concave recess with grooves, a mandrel, a leveling brace, and a dipping handle, in accordance with one embodiment of the present patent application.

Referring to FIG. 38, in one embodiment, a shell molding system 1190 preferably includes a mandrel 1200, a mold 1220 having a concave recess that is adapted to receive the mandrel 1200, a leveling brace 1222 for aligning the mandrel relative to the mold, and a dipping handle 1224 that has a lower end that is secured to the mandrel. As will be described in more detail herein, in one embodiment, the concave recess of the mold preferably includes a concave surface having grooves formed therein that is adapted to oppose a smooth convexly curved outer surface of the mandrel 1200 for forming ribs on a surface of a shell, as will be described in more detail herein.

Figure 39A:
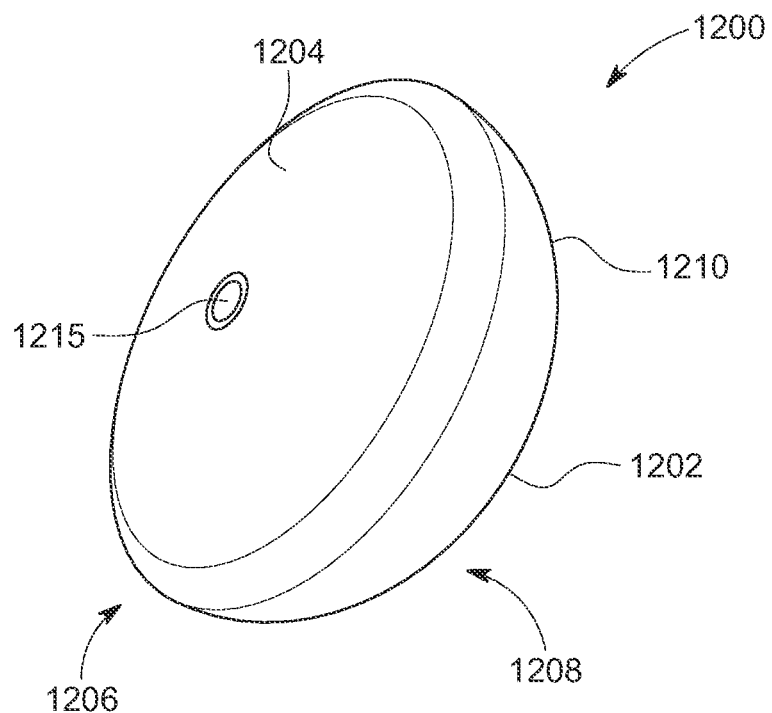
FIG. 39A is a perspective of the mandrel shown in FIG. 38.
Figure 39B:
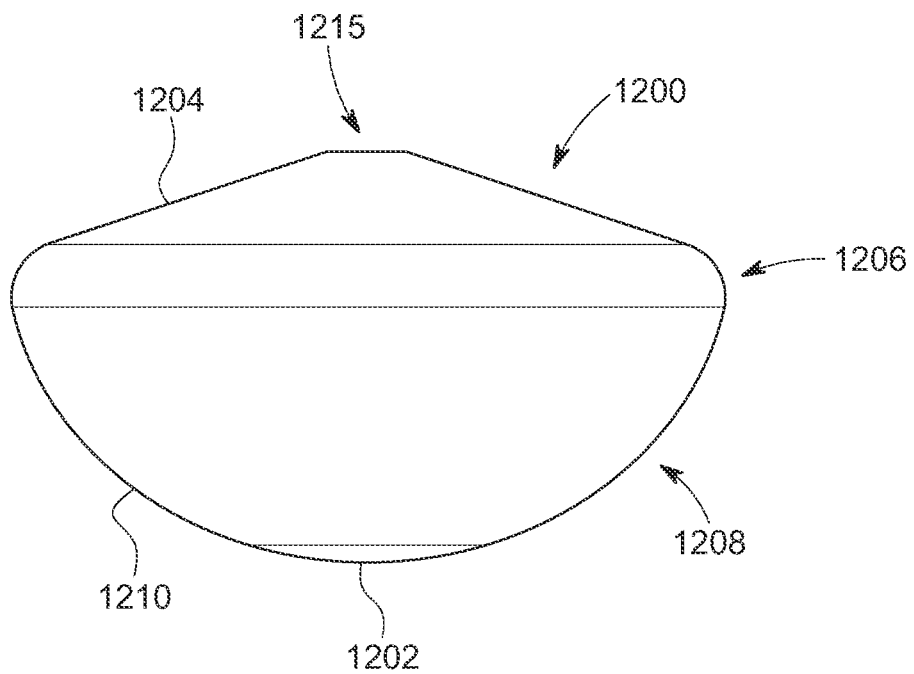
FIG. 39B is a side elevation view of the mandrel shown in FIG. 38.

Referring to FIGS. 39A and 39B, in one embodiment, the mandrel 1200 preferably includes an apex 1202 at an upper end of the mandrel, a base 1204 at a lower end of the mandrel, a radius 1206 that extends around the circumference of the mandrel 1200, and a dome 1208 having the convexly curved surface 1210 that extends between the apex 1202 and the base 1204. In one embodiment, the convexly curved outer surface 1210 of the mandrel 1200 is preferably smooth.

Referring to FIG. 39A, in one embodiment, the mandrel 1200 desirably includes an internally threaded opening 1215 that is centrally located on the base 1204, which is adapted to receive external threads provided at a lower end of the dipping handle 124 (FIG. 38).

Figure 40:
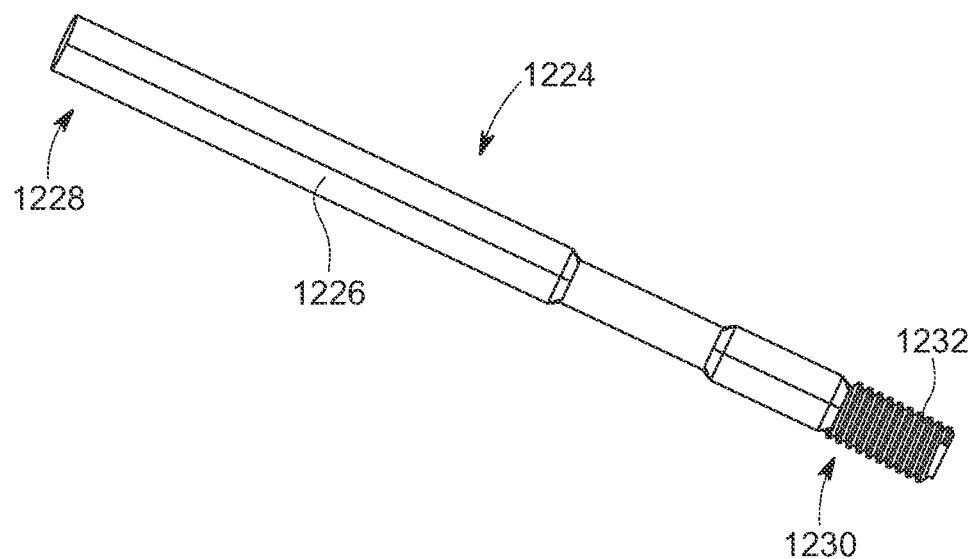
FIG. 40 is a side view of the dipping handle shown in FIG. 38.

Referring to FIGS. 38 and 40, in one embodiment, the dipping handle 1224 preferably includes an elongated shaft 1226 having an upper end 1228 with a hexagonal-shaped cross-section, and a lower end 1230 having external threads 1232 that are adapted to be threaded into the internally threaded opening 1215 of the mandrel 1200 shown in FIG. 39A.

Figure 41:
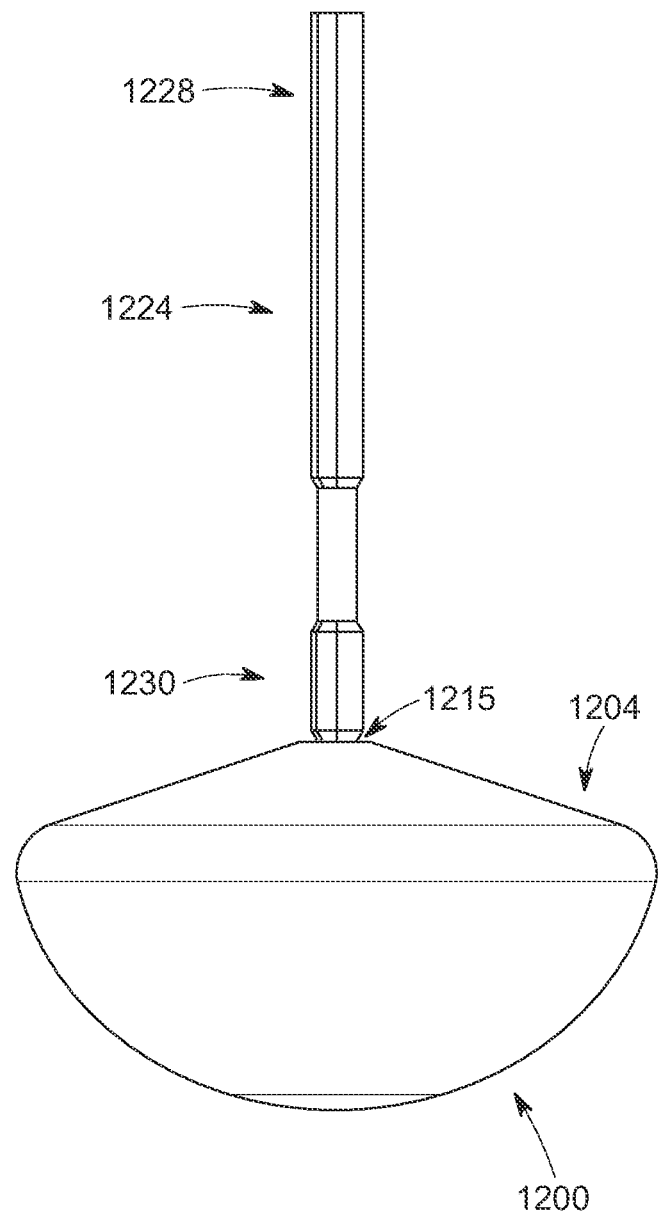
FIG. 41 is a front elevation view of an assembly including the mandrel of FIGS. 39A and 39B and the dipping handle of FIG. 40, in accordance with one embodiment of the present patent application.

Referring to FIG. 41, in one embodiment, the external threads 1232 (FIG. 40) at the lower end 1230 of the dipping handle 1224 may be threaded into the internally threaded opening 1215 (FIG. 39A) provided in the base 1204 of the mandrel 1200 for assembling the mandrel and the dipping handle together. In one embodiment, the upper end 1228 of the dipping handle 1224 has a hexagonal-shaped cross-section that is adapted to mesh with a hexagonal-shaped opening formed in the leveling brace 1222 (FIG. 38) for facilitating alignment of the mandrel with concave recess of the mold 1220 (FIG. 38).

Figure 42A:
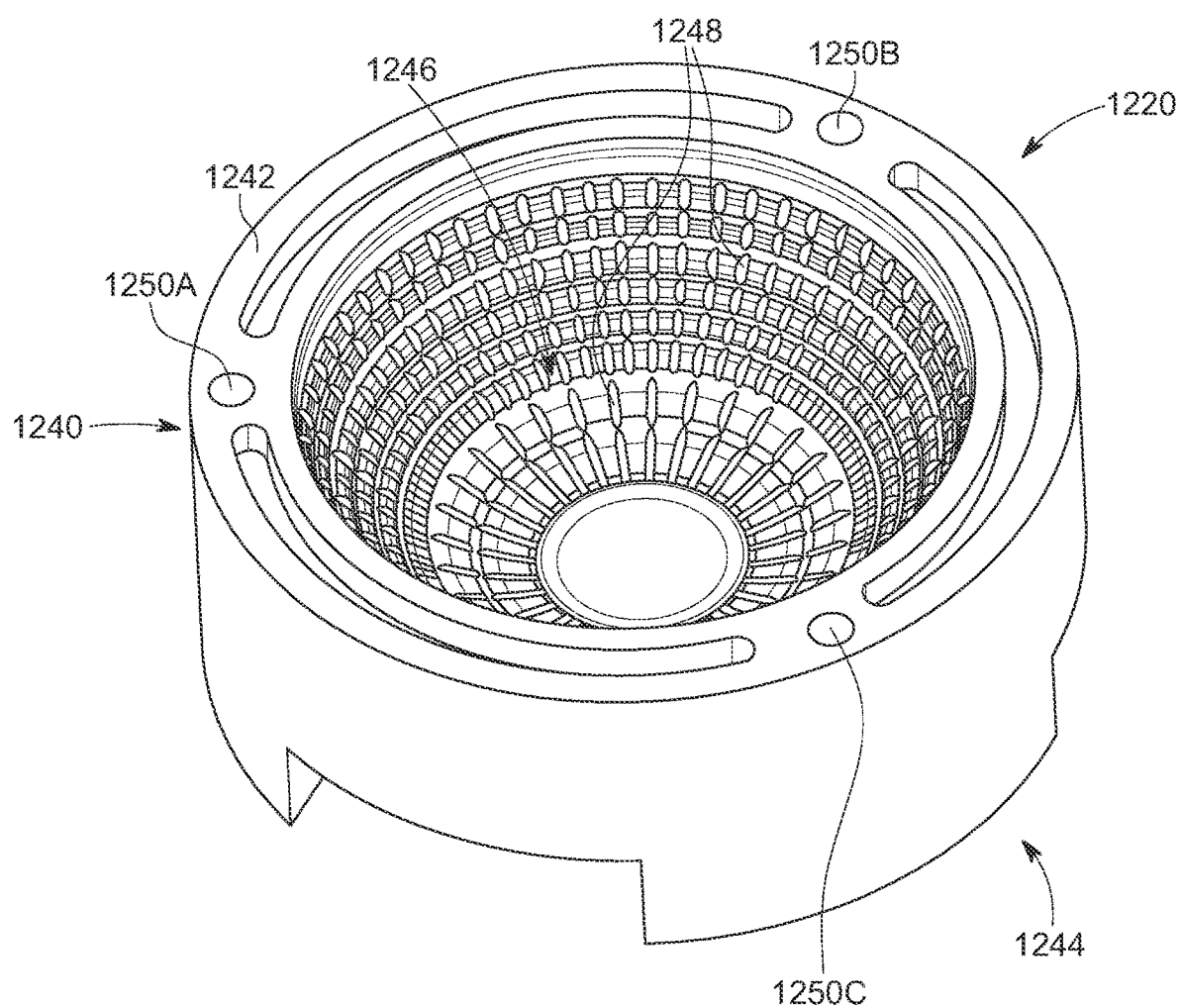
FIG. 42A is a top perspective view of the mold having the concave recess with grooves shown in FIG. 38.

Referring to FIG. 42A, in one embodiment, the mold 1220 preferably has an upper end 1240 defining a top face 1242 and a lower end 1244 that defines a bottom side of the mold 1220. In one embodiment, the concave recess 1246 of the mold 1220 is formed in the top face 1242 of the mold 1220. The concave recess 1246 desirably has a concave surface that preferably conforms to the shape of the convexly curved outer surface 1210 of the mandrel 1200 (FIG. 39B). In one embodiment, the concave recess 1246 desirably has grooves 1248 formed in the concave surface thereof. The grooves are adapted to receive a curable material such as a curable silicone material for forming ribs on a surface of a shell provided on the mandrel when the mandrel is inserted into the concave recess 1246 of the mold 1220.

In one embodiment, the top face 1242 of the mold 1220 desirably includes spaced alignment openings 1250A-1250C that are adapted to receive legs provided on the leveling brace 1222 (FIG. 38) for securing the leveling brace over the top face 1242 of the mold 1220 and properly aligning the mandrel with the mold.

Figure 42B:
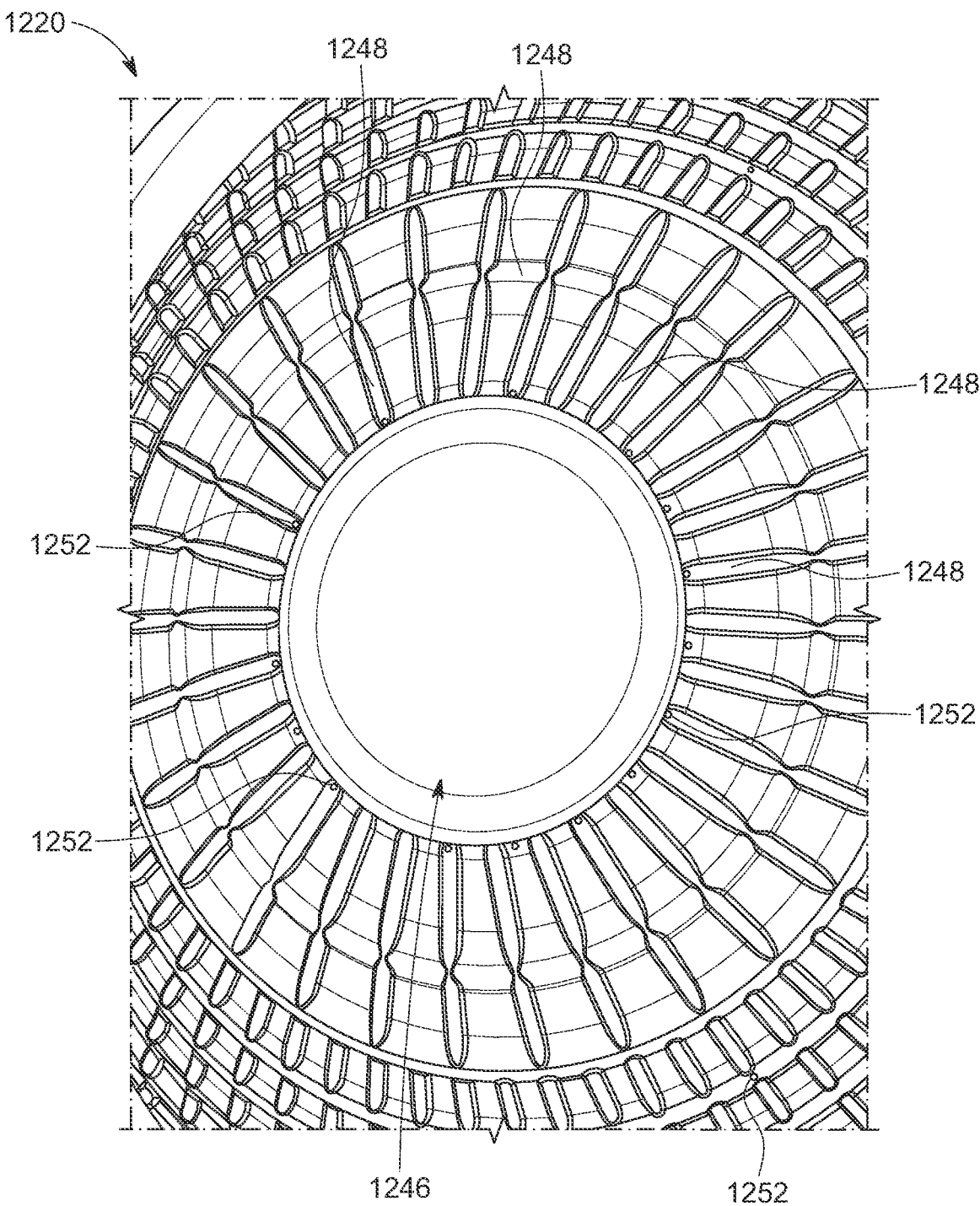
FIG. 42B is a magnified view of the concave recess of mold shown in FIG. 42A.

Referring to FIG. 42B, in one embodiment, the concave surface of the concave recess 1246 of the mold 1220 desirably includes one or more vent holes 1252 that are spaced from one another about the area of concave surface of the concave recess 1246 for enabling gases to be vented from the curable silicone material for minimizing bubble formation when making an implant shell. The concave recess 1246 preferably includes one or more grooves 1248 formed therein that are adapted to receive a curable material (e.g., curable silicone) that is disposed between the mandrel and the mold.

Figure 42C:
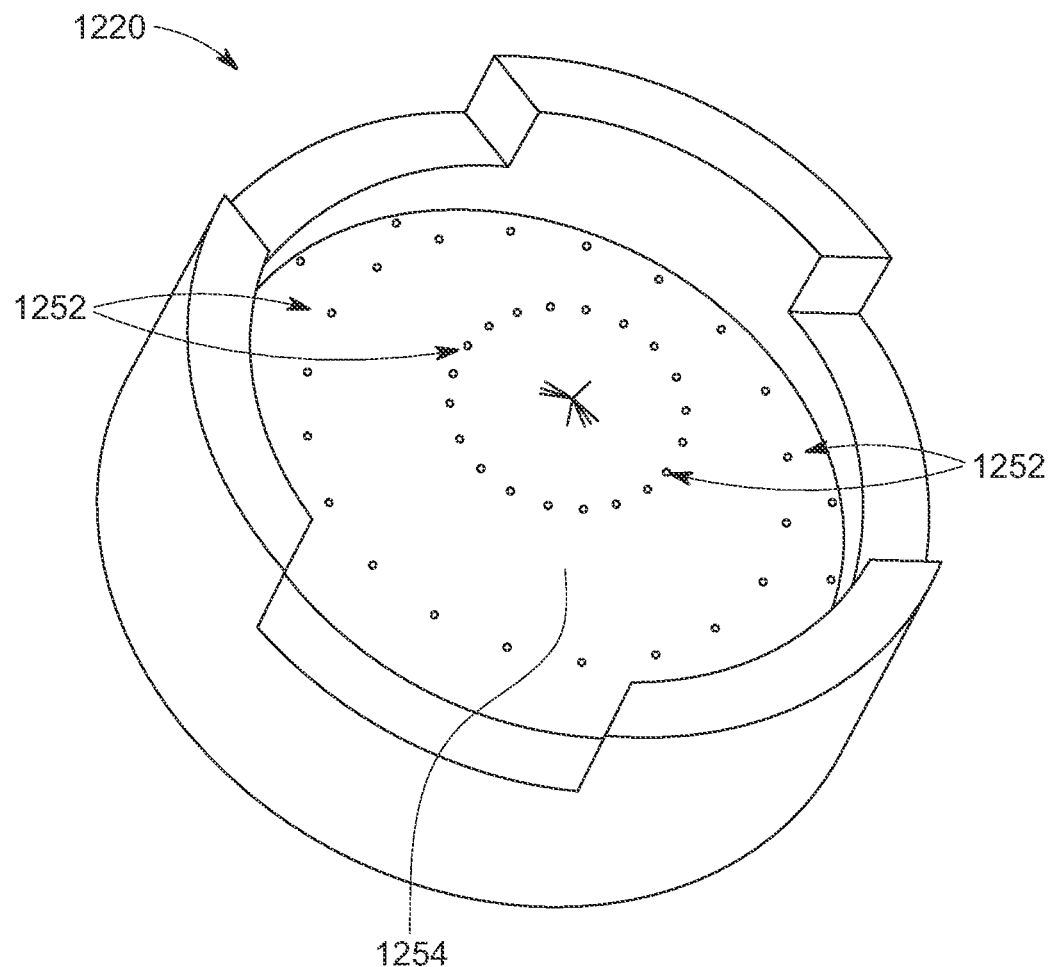
FIG. 42C shows a perspective view of an underside of the mold shown in FIG. 42A.

Referring to FIG. 42C, in one embodiment, the underside of the mold 1220 preferably includes a convexly curved surface 1254 that is a negative image of the concave recess 1246 formed in the topside of the mold 1220. The convexly curved surface 1254 includes the vent holes 1252 that are shown and described above in FIG. 42B. The vent holes 1252 enable any gases present in the curable rib forming material (e.g., curable silicone) to be vented from the curable material and/or the mold to minimize the formation of bubbles within the walls or ribs of a cured shell having integral ribs. In one embodiment, the vent holes 1252 may be evenly spaced from one another about the convexly curved surface 1254 of mold 1220.

Figure 43A:
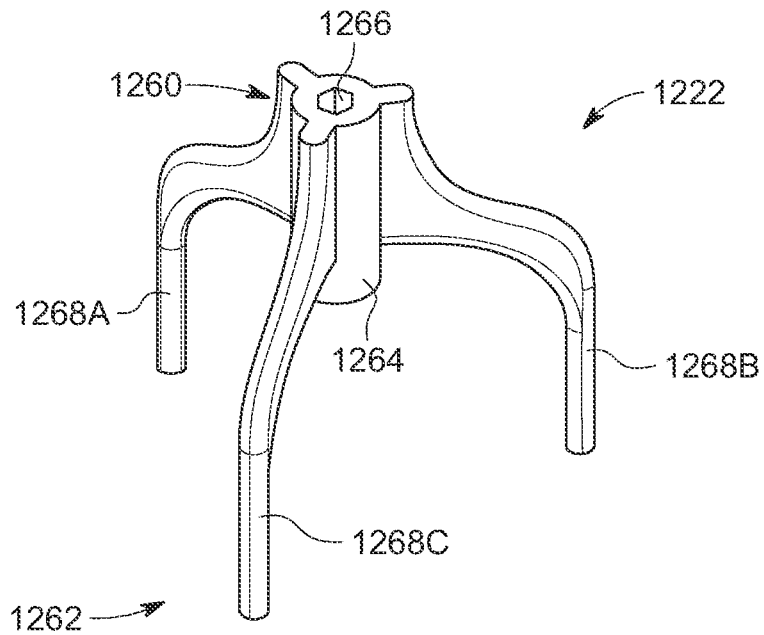
FIG. 43A is a perspective view of the leveling brace shown in FIG. 38.
Figure 43B:
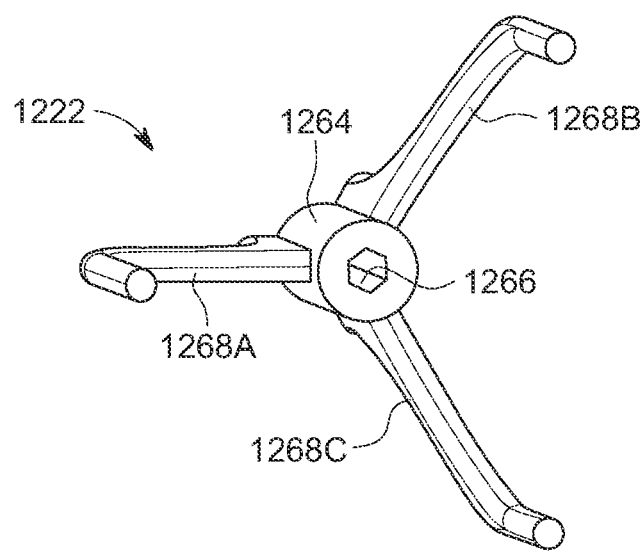
FIG. 43B is a perspective view of an underside of the leveling brace shown in FIG. 38.

Referring to FIGS. 43A and 43B, in one embodiment, the shell molding system desirably includes the leveling brace 1222 (FIG. 38) having an upper end 1260 and a lower end 1262. The leveling brace 1222 desirably includes a central hub 1264 having a hexagonal shaped opening 1266 that extends from an upper end of the central hub 1264 to a lower end of the central hub. The hexagonal-shaped opening 1266 is preferably configured to receive the hexagonal-shaped upper end 1228 of the dipping handle 1224 (FIG. 40).

In one embodiment, the leveling brace 1222 desirably includes three alignment legs 1268A-1268C having respective lower ends that are adapted to be received in the spaced alignment openings 1250A-1250C provided in the top face 1242 of the mold 1220 (FIG. 42A). The shape of the lower ends of the respective alignment legs 1268A-1268C preferably match the shape of the alignment openings provided in the top face 1242 of the mold for providing proper alignment and stability between the leveling brace 1222 and the mold 1220 (FIG. 42A).

Figure 44A:
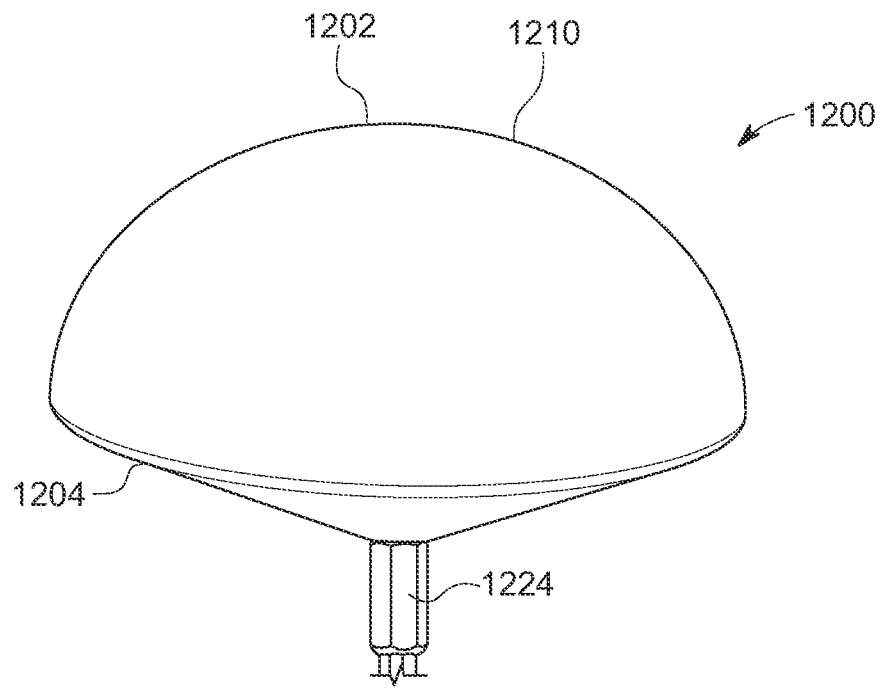
FIG. 44A is a side view of the mandrel and the dipping handle of FIG. 41 with the mandrel in an upright configuration, in accordance with one embodiment of the present patent application.

Referring to FIG. 44A, in one embodiment, the dipping handle 1224 (FIG. 40) is secured to the base 1204 of the mandrel 1200. The mandrel 1200 preferably has a smooth convexly curved outer surface 1210 that extends between the apex 1202 and the base 1204 of the mandrel 1200. In one embodiment, the dipping handle 1224 is utilized for positioning the mandrel 1200 in an upright orientation so that the apex 1202 of the mandrel is located above the base 1204 of the mandrel. In one embodiment, a curable material such as a curable silicone material may be deposited over the convexly curved outer surface 1210 of the mandrel 1200 for forming a shell over the outer surface of the mandrel. In the position shown in FIG. 44A, the curable shell forming material may be sprayed and/or deposited over the convexly curved outer surface of the mandrel for building up one or more layers of material that constitute the wall thickness of the implant shell.

Figure 44B:
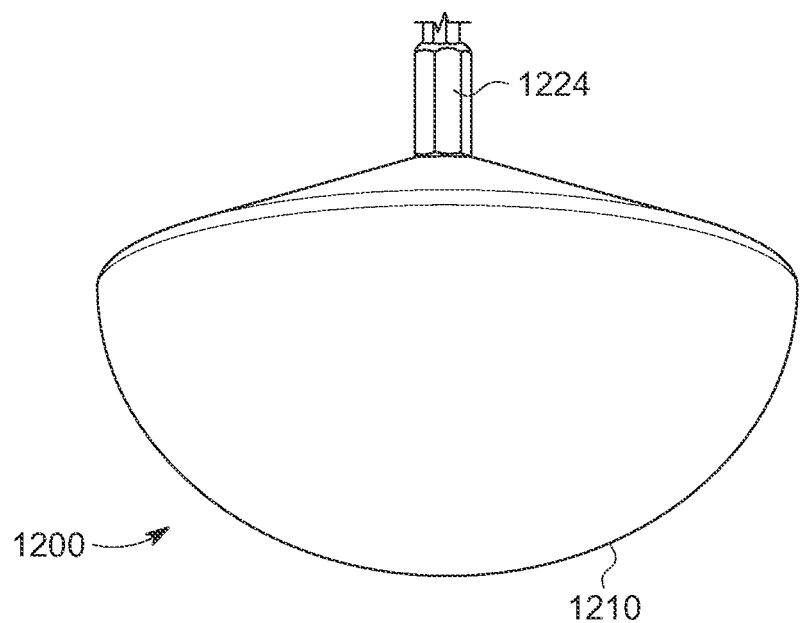
FIG. 44B is a side view of the mandrel and the dipping handle of FIG. 41 with the mandrel in an inverted configuration, in accordance with one embodiment of the present patent application.

Referring to FIG. 44B, in one embodiment, during one or more stages of the shell forming process, the mandrel 1200 may be positioned into an inverted orientation for dipping the mandrel into a curable material for further building layers of material onto the shell to increase the wall thickness of the shell being formed on the convexly curved outer surface 1210 of the mandrel 1200. In one embodiment, after a shell has been formed on the mandrel 1210, the mandrel may be inserted into the concave recess 1246 (FIG. 42A) of the mold 1220 (FIG. 38) for forming ribs on a surface of the shell.

Figure 45A:
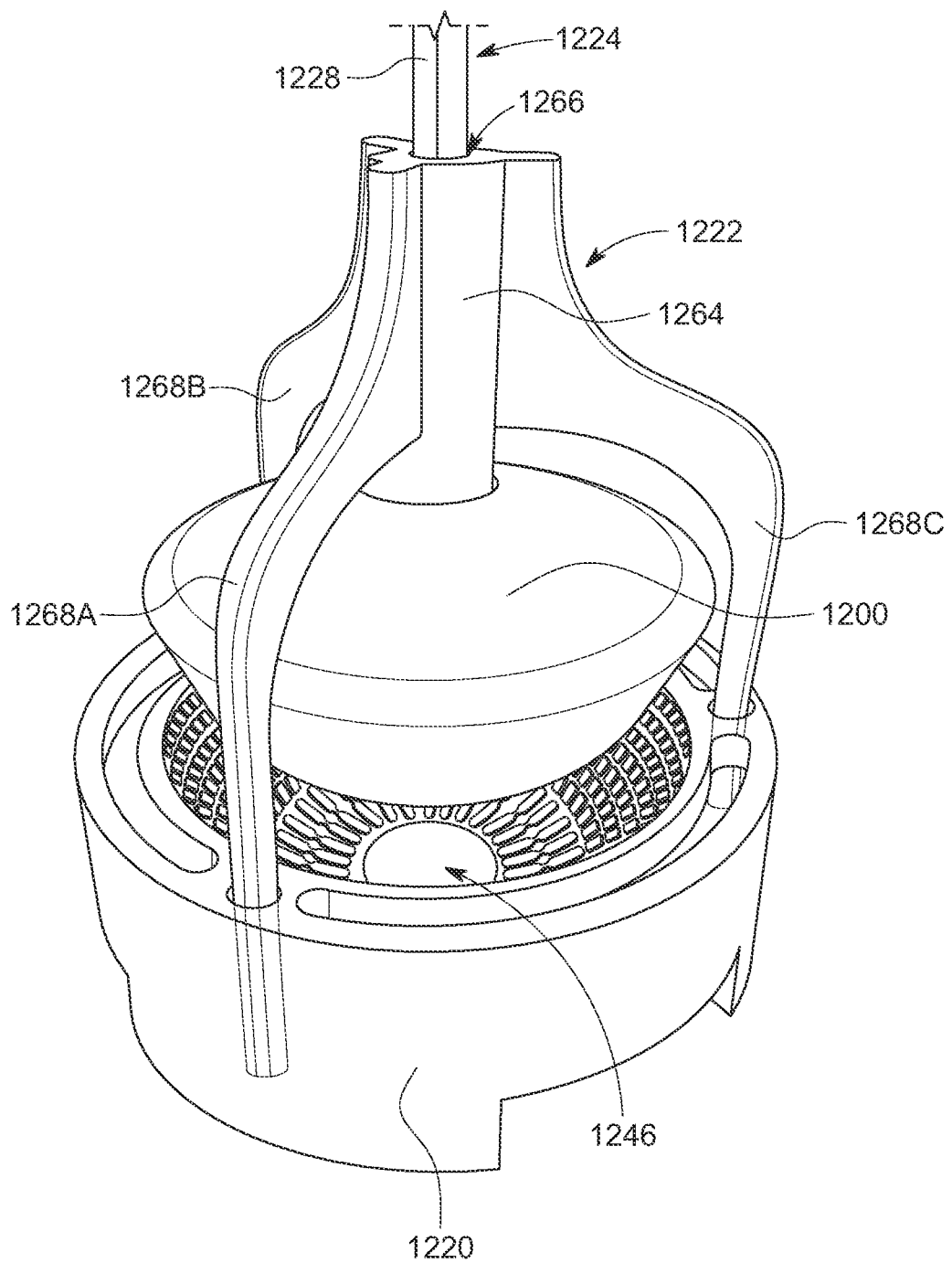
FIG. 45A is perspective view of the shell molding system of FIG. 38 with a convexly curved surface of the mandrel spaced away from the concave recess of the mold, in accordance with one embodiment of the present patent application.

Referring to FIG. 45A, in one embodiment, after a shell or a shell precursor has been formed on the convexly curved outer surface of the mandrel 1200, the apex of the mandrel is preferably juxtaposed with the concave recess 1246 formed in the top face 1242 of the mold 1220. In order to properly align the mandrel 1200 with the leveling brace 1222, the hex-shaped upper end 1228 of the dipping handle 1224 is desirably passed through the hex-shaped opening 1266 provided in the central hub 1264 of the leveling brace 1222.

Figure 45B:
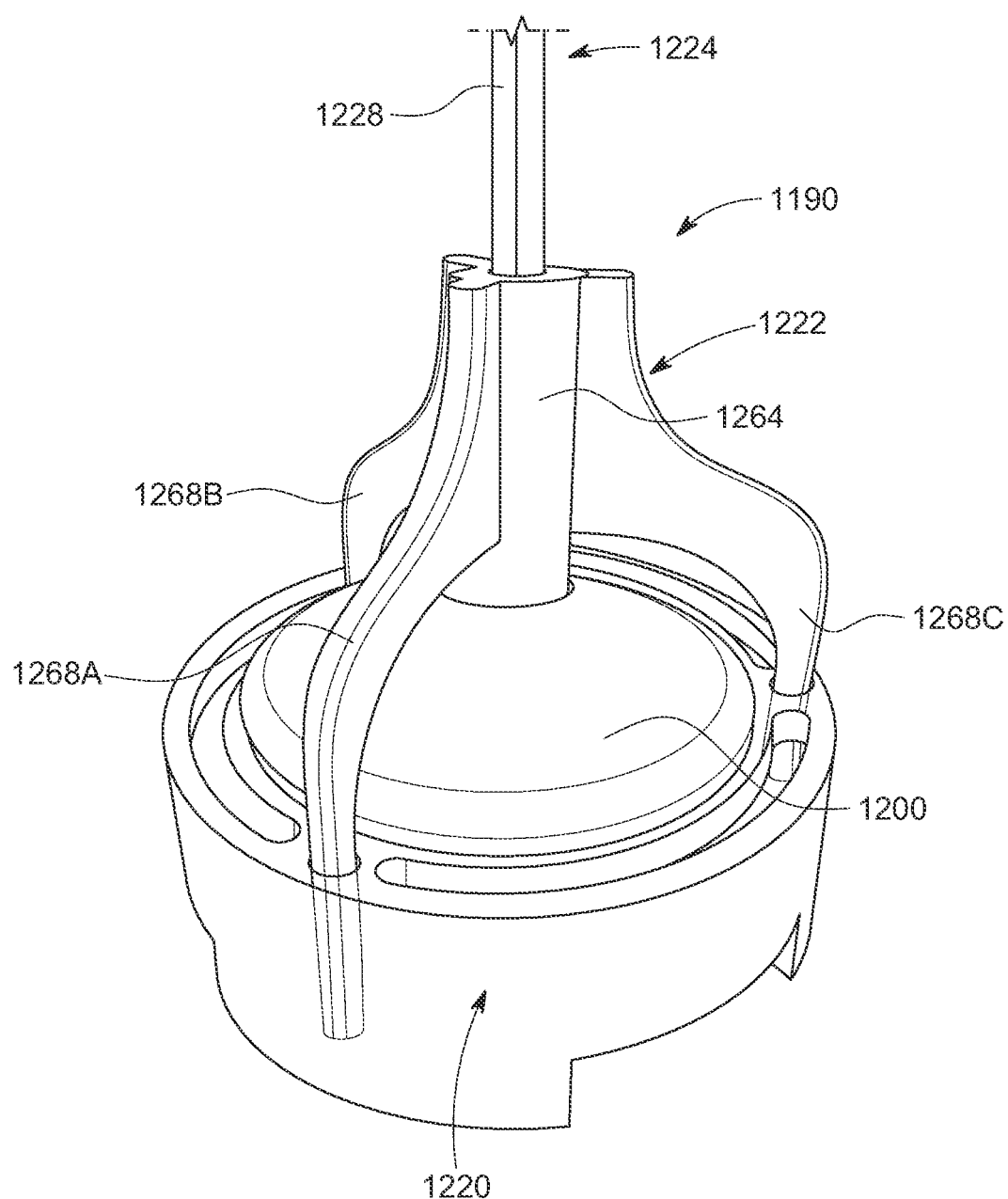
FIG. 45B is perspective view of the shell molding system of FIG. 38 with the convexly curved surface of the mandrel disposed within the concave recess of the mold, in accordance with one embodiment of the present patent application.
Figures 1, 45B:
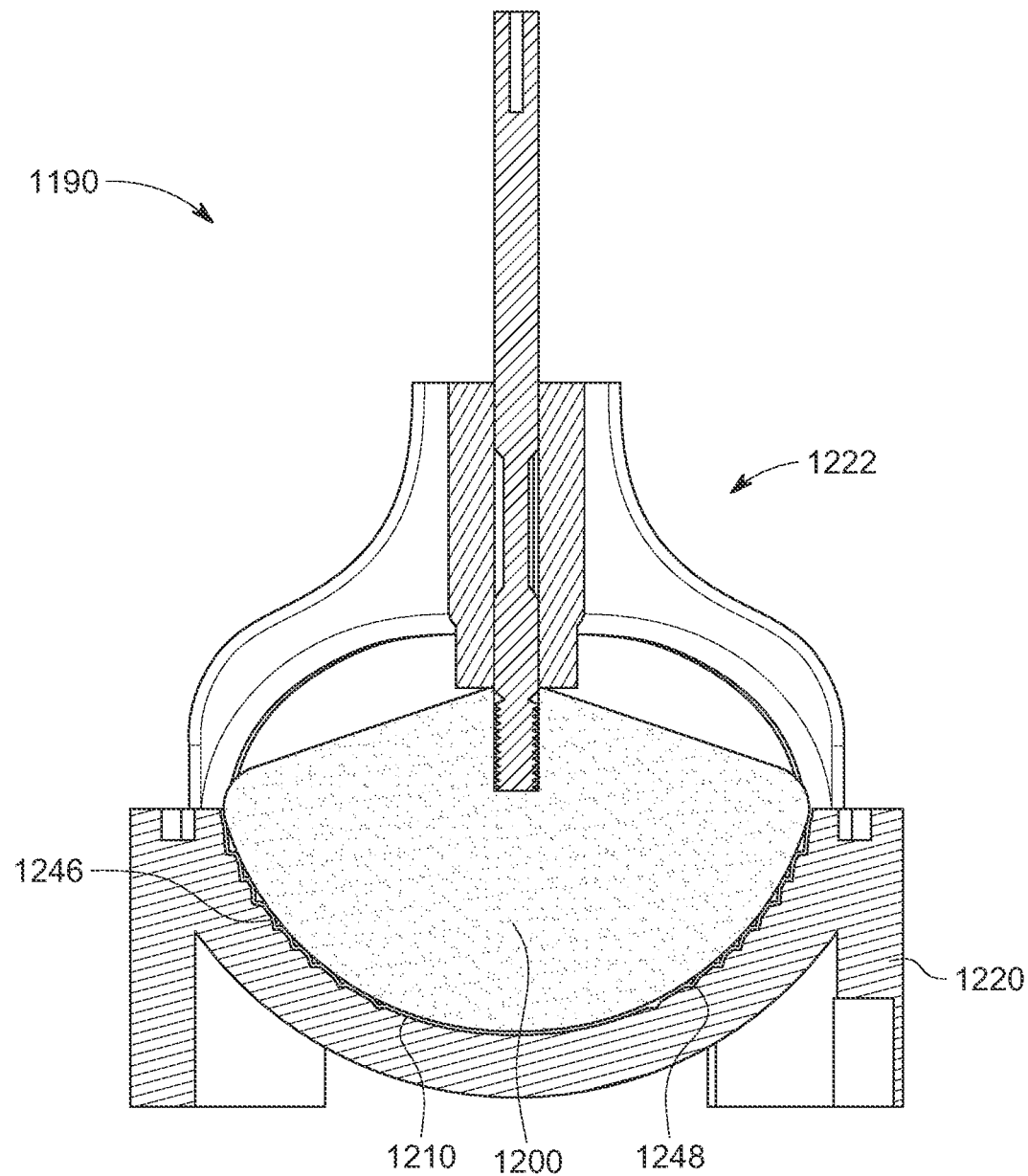

Referring to FIGS. 45A and 45B, in one embodiment, in order to properly align the mandrel 1200 with the concave recess 1246 of the mold 1220, the lower ends of the alignment legs 1268A-1268C of the leveling brace 1220 are preferably inserted into the alignment openings 1250A-1250C (FIG. 42A) provided in the top face 1242 of the mold 1220.

In one embodiment, prior to fully inserting the alignment legs 1268A-1268C into the alignment openings of the mold 1220, a curable shell forming material such as curable silicone may be applied over the concave recess 1246, whereupon at least a portion of the curable shell forming material flows into the grooves 1248 (FIG. 42A) formed in the concave surface of the concave recess. The convexly curved outer surface 1210 of the mandrel 1200 including the shell overlying the convexly curved outer surface may be pressed against the convexly curved outer surface of the mandrel 1200 whereupon the curable shell forming material on the concave recess of the mold 1220 forms ribs on the surface of the implant shell.

Figure 1:
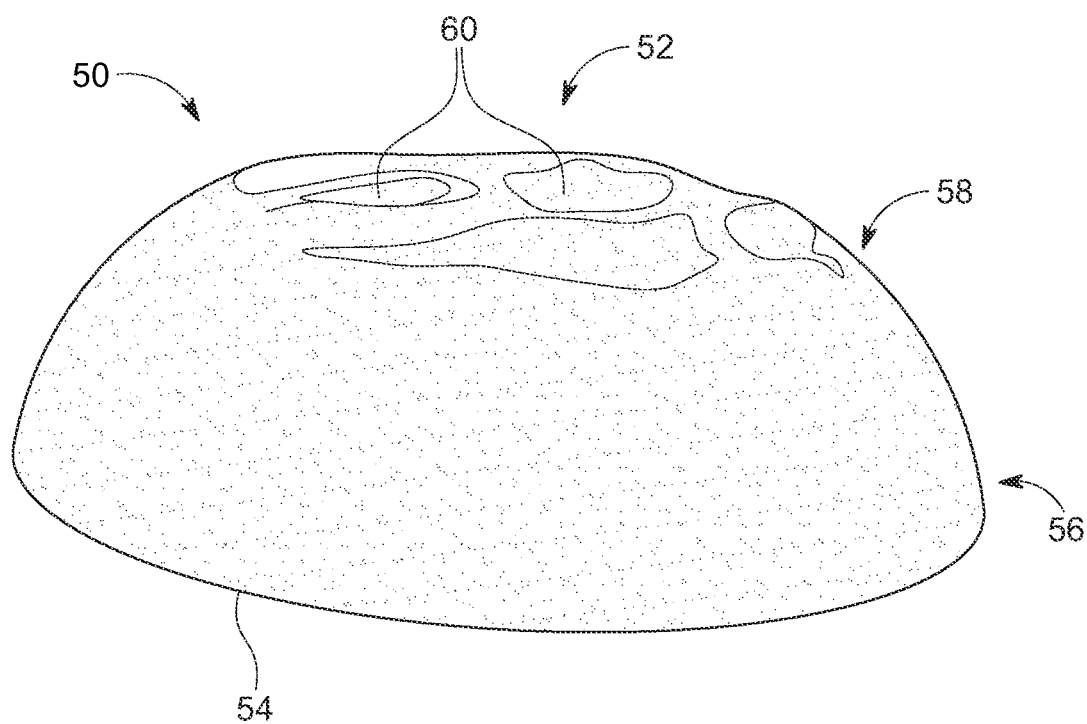
FIG. 1 shows a prior art implant having concavities at the apex of the shell.
Figure 2:
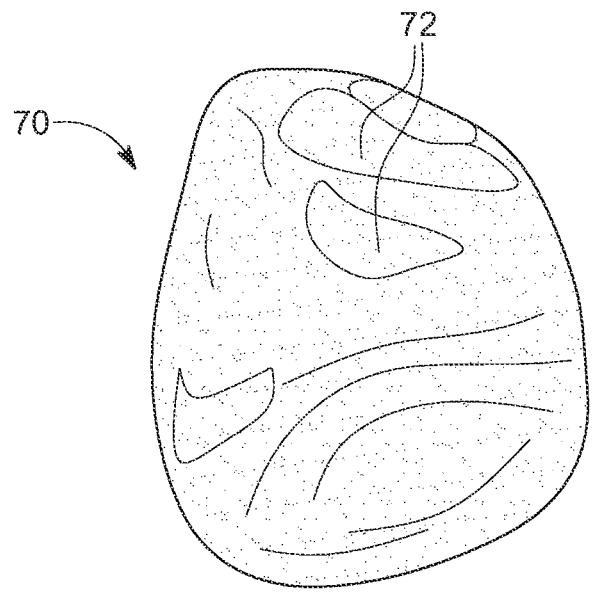
FIG. 2 shows a prior art implant with rippling of the shell.
Figure 3:
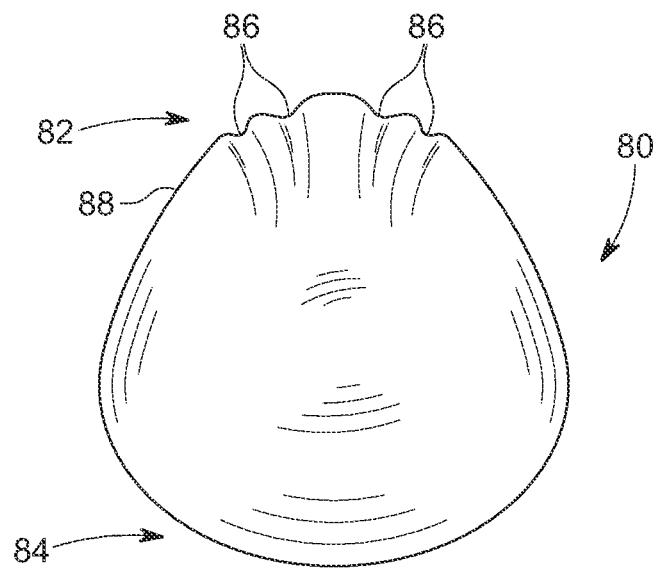
FIG. 3 shows a prior art implant with scalloping at an edge of the shell.

Referring to FIGS. 45B and 45B-1, in one embodiment, after the lower ends of the alignment legs 1268A-1268C of the leveling brace 1222 are fully inserted into the alignment openings 1250A-1250C (FIG. 42A) of the mold 1220, the convexly curved outer surface of the mandrel 1200 abuts against the concave surface of the concave recess 1246 formed in the mold 1220. The hexagonal-shaped upper end 1228 of the dipping handle passes through the hexagonal-shaped opening of the hub 1264 for stabilizing and aligning the mandrel 1200 relative to the leveling brace 1222, and the alignment legs 1268A-1268C inserted into the alignment openings of the mold 1220 further align and stabilize the mandrel 1200 relative to the concave recess 1246 (FIG. 42A) of the mold 1220. In one embodiment, as the mandrel is advanced into the concave recess of the mold, the flowable silicone material extrudes into the grooves formed in the concave recess of the mold. In one embodiment, the shell molding system 1190 shown in FIGS. 45B and 45B-1 may be placed into an oven or exposed to heat whereby the curable material provided in the grooves of the mold is cured to provide ribs that are integral with the surface of the shell. During rib formation and/or while curing the ribs, any excess gases present in the curable shell forming material may be extruded through the vent holes provided in the mold to minimize the formation of bubbles in the fully cured shell.

Figure 46A:
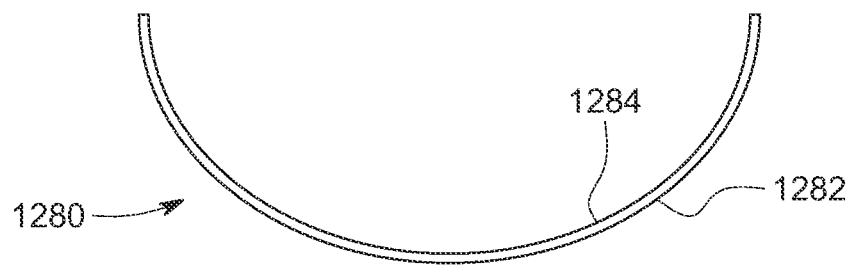
FIG. 46A is a schematic view of a first step of making an implant shell having integral ribs, in accordance with one embodiment of the present patent application.
Figure 46B:
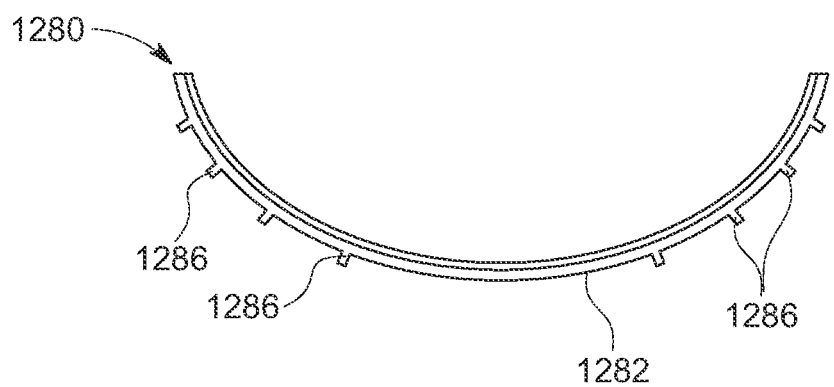
FIG. 46B is a schematic view of a second stage of a method of making an implant shell having integral ribs, in accordance with one embodiment of the present patent application.
Figure 46C:
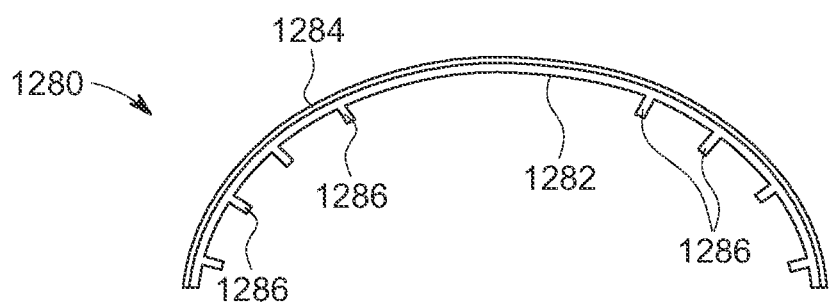
FIG. 46C is a schematic view of a third stage of a method of making an implant shell having integral ribs, in accordance with one embodiment of the present patent application.

FIGS. 46A-46C show a schematic view of one or more stages of a method of forming integral ribs on a shell. Referring to FIG. 46A, in one embodiment, a shell precursor 1280' is formed over a convexly curved outer surface of a mandrel such as the mandrel 1200 shown and described above in FIGS. 44A-44B and 45A-45B-1. The shell precursor 1280' desirably has a first surface 1282 that is substantially smooth and a second surface 1284 that is also substantially smooth.

Referring to FIG. 46B, an implant shell molding system such as that shown and described above in FIGS. 44A-44B and 45B-45B-1 may be utilized for forming ribs 1286 that are secured to the first exposed surface 1282 of the shell precursor 1280' shown and described above in FIG. 46A. The subassembly shown in FIG. 46B is preferably cured such as by placing the implant shell molding system 1990 (FIG. 38) in a curing oven or by applying heat so that the ribs 1286 are fully cured and are integrally secured to the first exposed surface 1282 of the shell 1280. At this stage, the ribs preferably extend from the first surface 1282 of the shell 1280.

Referring to FIG. 46C, in one embodiment, in order to provide an implant shell 1280 having inwardly extending ribs 1286, the shell 1280 may be removed from the mandrel 1200 (FIG. 45B-1) and inverted so that the first surface 1282 of the shell defines an inner surface of the shell 1280 and the second surface 1284 of the shell defines the outer surface of the implant shell 1280. After inverting the shell 1280, the shell preferably has inwardly extending ribs 1286 that extend into an interior volume of the shell 1280, whereby the second surface 1284 of the shell defines a smooth outer surface of the shell 1280. The shell 1280 may be filled with a shell filling material such as a silicone gel or saline solution for providing a shell that may be used as a mammary implant or a tissue expander. The inwardly extending ribs 1286, which are integrally formed with the shell wall, preferably enhance the profile and the stability of the shell 1280 as described is further detail herein.

Referring to 47A, in one embodiment, an injection molding system 1300 may be utilized for forming ribs on an implant shell (e.g., a mammary implant). In one embodiment, the injection molding system 1300 desirably includes a lower mold part 1302 and an upper mold part 1304 that may be moved between an open position for inserting a mandrel 1306 into the mold (or removing the mandrel from the mold), and a closed position for performing an injection molding process. In one embodiment, the mandrel 1306 preferably includes a convexly curved surface 1308 having one or more grooves 1310 formed on the convexly curved surface.

In one embodiment, the upper mold part 1304 preferably includes injection ports 1312 that are directed toward the convexly curved surface 1308 of the mandrel 1306 for introducing a curable material, such as curable silicone, between the upper mold part 1304 and the lower mold part 1302, whereupon the curable material flows over the convexly curved surface of the mandrel and into the grooves provided on the mandrel. The curable silicone material is preferably introduced through the injection ports 1312 for forming an implant shell over the convexly curved surface 1308 of the mandrel 1306.

Figure 47A:
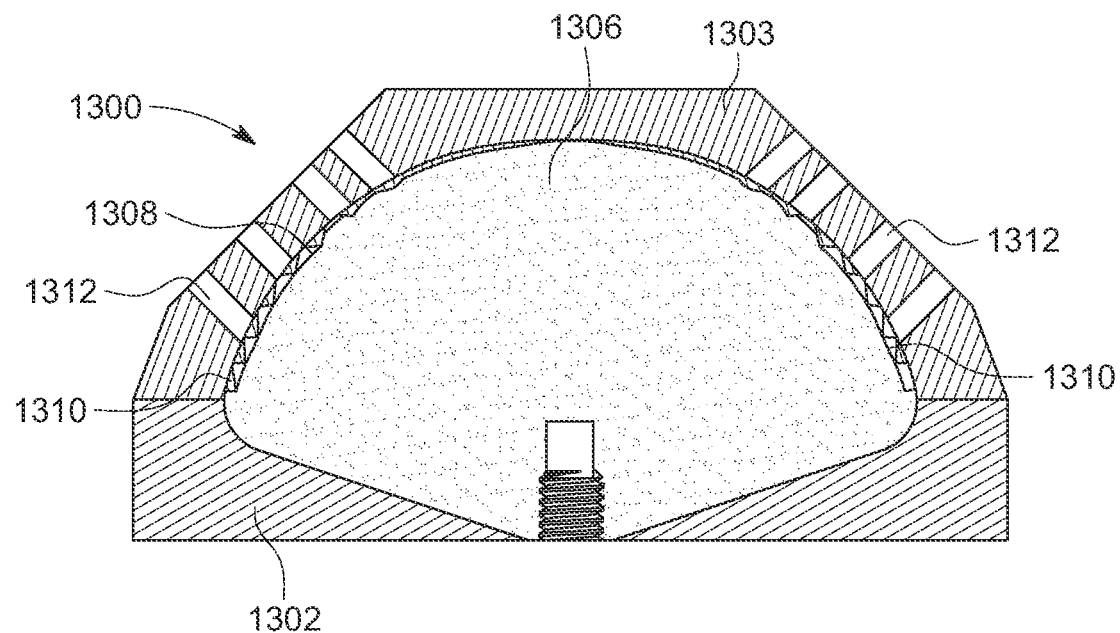
FIG. 47A is a cross-sectional view of an injection molding system including male and female mold parts, in accordance with one embodiment of the present patent application.
Figure 47B:
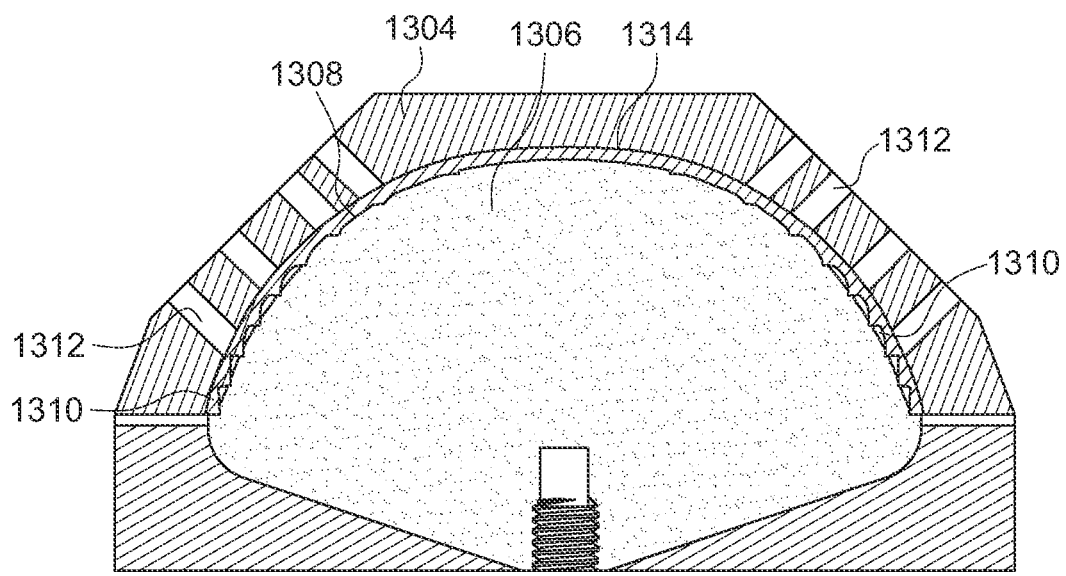
FIG. 47B is a cross-sectional view of the injection molding system of FIG. 47A after a curable shell forming material has been injected into the injection molding system, in accordance with one embodiment of the present patent application.

Referring to FIG. 47B, in one embodiment, a curable material 1314 may be introduced through the injection ports 1312 provided in the upper mold part 1304 to form a layer of curable material over the convexly curved surface 1308 of the mandrel 1306. The curable material preferably flows between the underside of the upper mold part 1304 and the convexly curved outer surface 1308 of the mandrel 1306 so that the curable material is spread over the convexly curved outer surface of the mandrel. The curable material preferably flows into the grooves 1310 that are formed in the convexly curved surface 1308 of the mandrel 1306. The curable material that flows into the grooves is preferably cured for forming ribs that are integrally secured with the shell.

Figure 48A:
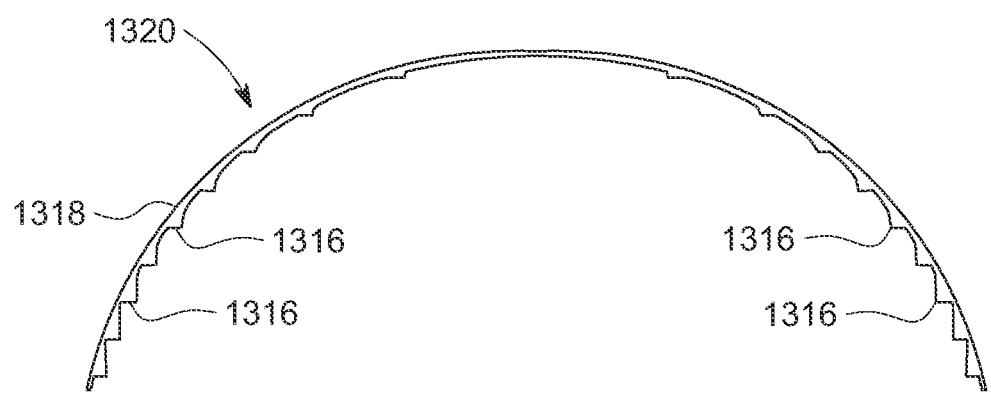
FIG. 48A is a schematic view of a first stage of a method of using the injection molding system of FIGS. 47A and 47B for making a shell having integral ribs, in accordance with one embodiment of the present patent application.
Figure 48B:
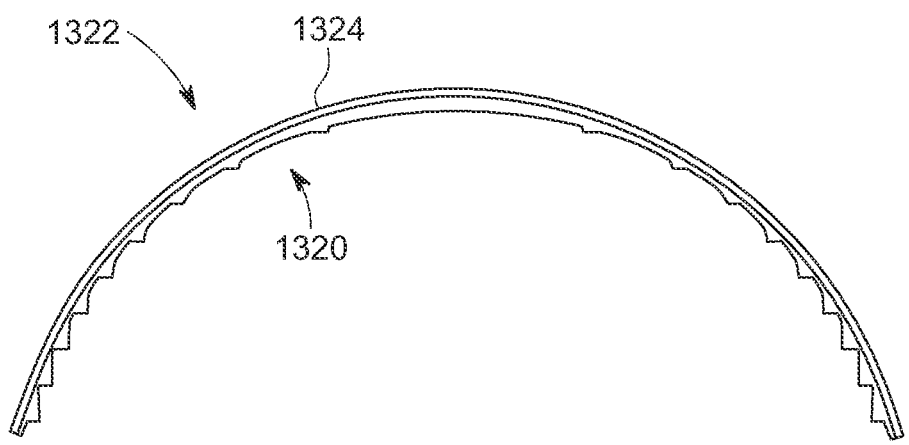
FIG. 48B is a schematic view of a second stage of a method of using the injection molding system of FIGS. 47A and 47B for making a shell having integral ribs, in accordance with one embodiment of the present patent application.

FIGS. 48A and 48B show a schematic view of a method of using an injection molding process to form a shell having integral ribs. Referring to FIG. 48, in one embodiment, after the curable material is injected through the injection port 1312 of the upper mold part 1304 (FIG. 47B), the curable material preferably flows into the grooves 1310 provided on the convexly curved outer surface of the mandrel to form ribs 1316 that project inwardly from the outer surface 1318 of the shell precursor 1320. In FIG. 48A, the shell precursor 1320 preferably overlies the convexly curved outer surface of the mandrel 1306 (FIG. 47B).

Referring to FIG. 48B, in one embodiment, the mandrel may be removed from the injection molding system 1300 shown in FIGS. 47A and 47B so that additional layers of curable material may be applied and/or deposited over the shell precursor 1320 shown in FIG. 48A. In one embodiment, one or more additional layers of curable material may be deposited over the outer surface of the shell precursor 1320 to increase the wall thickness of the shell 1322. The final wall thickness of the shell 1322 desirably includes the thickness present in the shell precursor 1320 (FIG. 48A) and the additional curable material deposited over the outer surface of the shell precursor after it has been removed from the injection mold system 1300 (FIGS. 47A and 47B). The additional curable material may be deposited by spraying and/or dipping the curable material onto the shell precursor so that one or more additional layers of curable material may be built up over the outer surface of the shell precursor 1320. In one embodiment, the mandrel including the shell precursor 1320 (FIG. 48A) and the additional layers of curable material 1324 applied over the shell precursor may be placed into a curing oven for curing the shell 1322 (FIG. 48B) for use as an implant (e.g., a mammary implant, a tissue expander). After the shell 1322 has been fully cured, it may be removed from the underlying mandrel before being filled with a gel or saline solution.

Figure 49A:
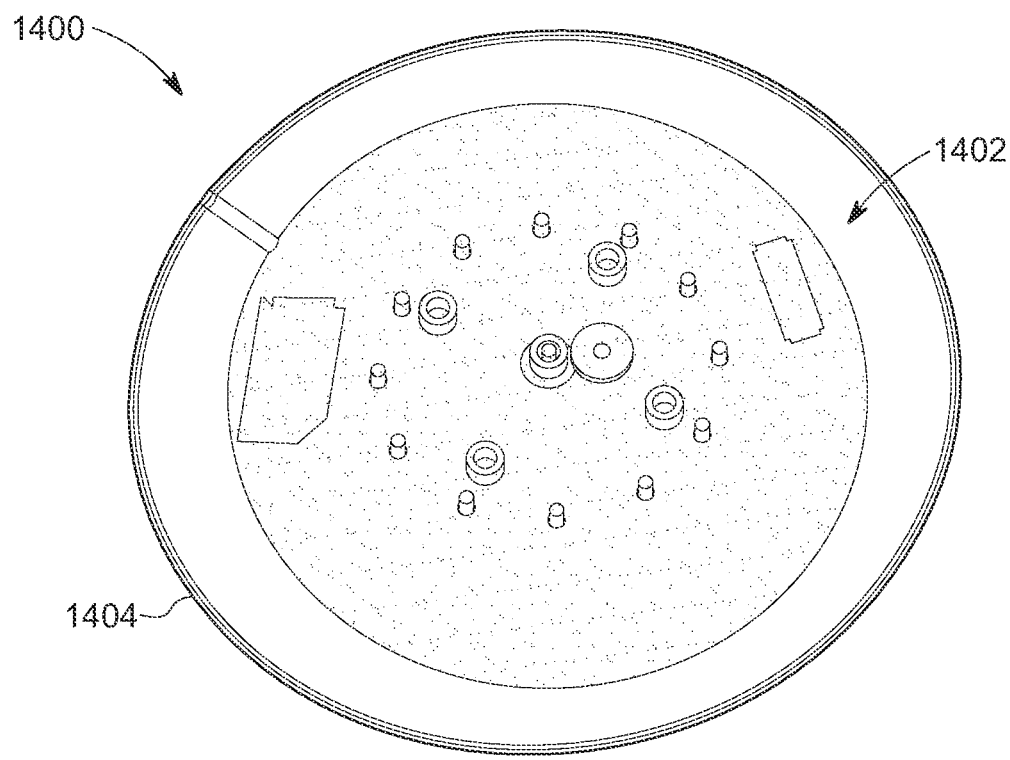
FIG. 49A is a perspective view of a top surface of a disk with a shell for an implant stretched over the top surface of the disk, in accordance with one embodiment of the present patent application.
Figure 49B:
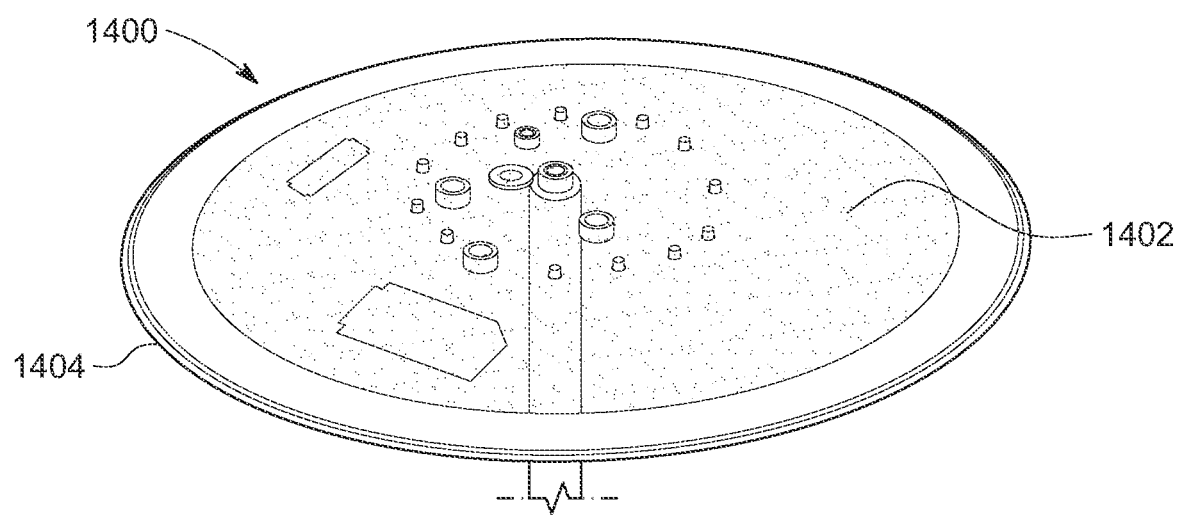
FIG. 49B is another perspective view of the top surface of the disk and the shell shown in FIG. 49A with an implant shell stretched over the disk, in accordance with one embodiment of the present patent application.

Referring to FIGS. 49A and 49B, in one embodiment, a stenciling system may be used for forming ribs on a surface of an implant shell. In one embodiment, the stenciling system may include a plate or disk 1400 having a top surface 1402 that is adapted to receive a shell that is desirably stretched over the outer perimeter 1404 of the disk 1400 so that a major surface of the shell overlies the top surface of the plate/disk. The top surface 1402 of the disk 1400 may be flat or slightly curved.

Referring to FIG. 49B, in one embodiment, a shell (e.g., a pre-formed silicone shell) is stretched over the outer perimeter 1404 of the disk 1400 so that a major surface of the shell overlies and is exposed over the top surface 1402 of the disc 1400. The major surface of the shell is preferably smooth and a stencil may be utilized for forming ribs over the major surface of the shell. In one embodiment, the ribs may be formed from a region of the shell that is not fully cured. In one embodiment, the ribs may be formed from a layer of unvulcanized material (e.g., silicone) that is applied over the major surface of the shell in either sheet or fluid form.

Figure 50A:
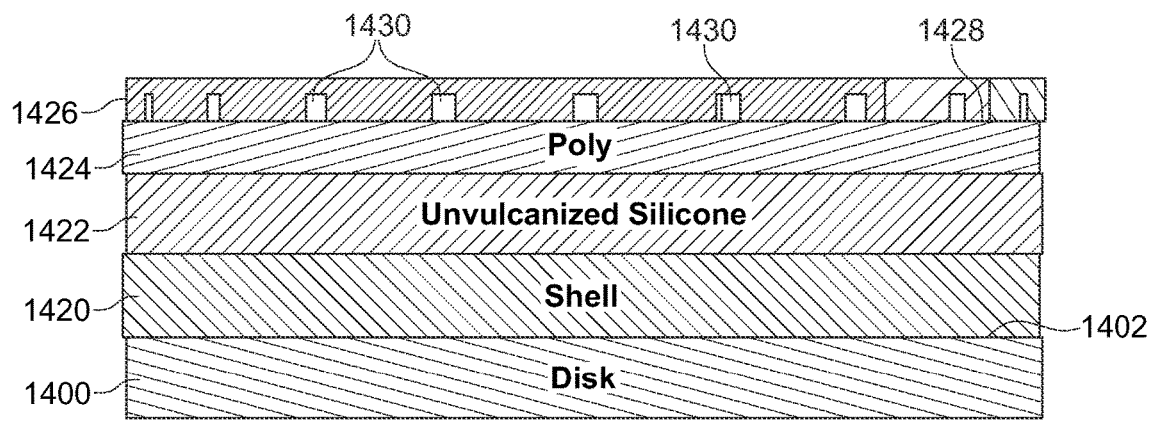
FIG. 50A illustrates a first stage of a method of using a stenciling system to make a shell having integral ribs, in accordance with one embodiment of the present patent application.

Referring to FIG. 50A, in one embodiment, a stenciling system used for forming ribs on a shell preferably includes the disk 1400 shown and described above in FIGS. 49A-49B, with a shell 1420 (e.g., a silicone shell) stretched over the top surface 1402 of the disk 1400. In one embodiment, the shell 1420 is fully cured before being positioned over the top surface 1402 of the disk 1400. In one embodiment, an unvulcanized silicone layer 1422 is positioned over a major surface of the shell 1420 and a release layer 1424 (e.g., poly sheeting made of polyethylene) is desirably placed over the unvulcanized silicone layer 1422. The stenciling system preferably includes a stencil 1426 having a bottom face 1428 with grooves 1430 formed therein for forming ribs in the unvulcanized silicone layer 1422. The release layer 1424 preferably prevents the unvulcanized silicone material in silicone layer 1422 from sticking to the grooves 1430 at the underside 1428 of the stencil 1426 so that the ribs formed by the stencil will release from the grooves of the stencil after a rib forming step has been completed.

Figure 50B:
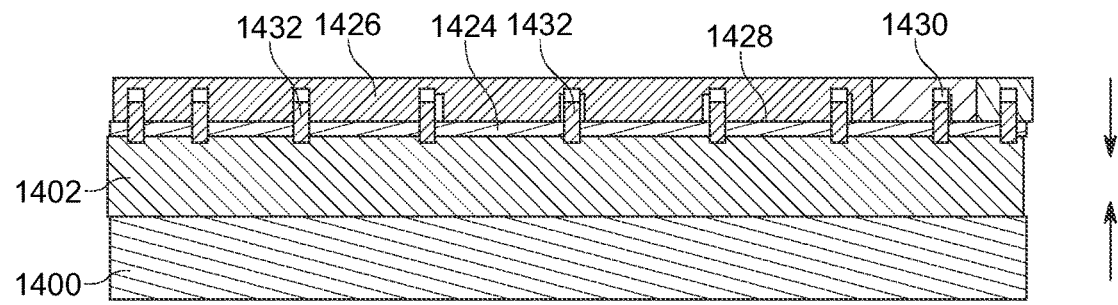
FIG. 50B illustrates a second stage of a method of using a stenciling system to make a shell having integral ribs, in accordance with one embodiment of the present patent application.

Referring to FIG. 50B, in one embodiment, in order to form ribs 1432 that are integrally secured with the shell 1420, the stencil 1426 may be pressed toward the top surface 1402 of the disk 1400 for compressing the shell 1420, the unvulcanized silicone layer 1422, and the poly release layer 1424 (FIG. 50A) between the bottom surface 1428 of the stencil 1426 and the top surface 1402 of the disk 1400. As the stencil 1426 is pressed toward the top surface of the disk 1400, the unvulcanized silicone material is forced into the grooves 1430 of the stencil 1426 to form ribs 1432 that project from the top surface of the silicone shell layer 1420.

Figure 50C:
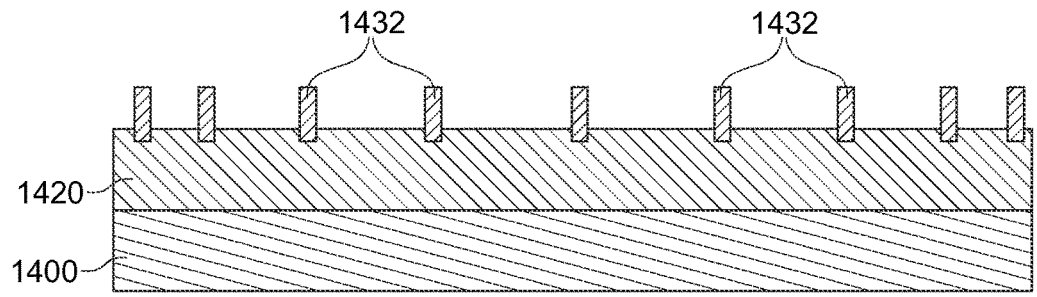
FIG. 50C illustrates a third stage of a method of using a stenciling system to make a shell having integral ribs, in accordance with one embodiment of the present patent application.

Referring to FIG. 50C, in one embodiment, after the stencil is pressed into the unvulcanized silicone layer 1422 (FIG. 50A) for forming the ribs 1432, the ribs preferably project from a top surface of the shell layer 1420. At this stage, the stencil may be removed, whereupon the shell 1420 with the integral ribs 1432 remains in place over the disk 1400.

Figure 50D:
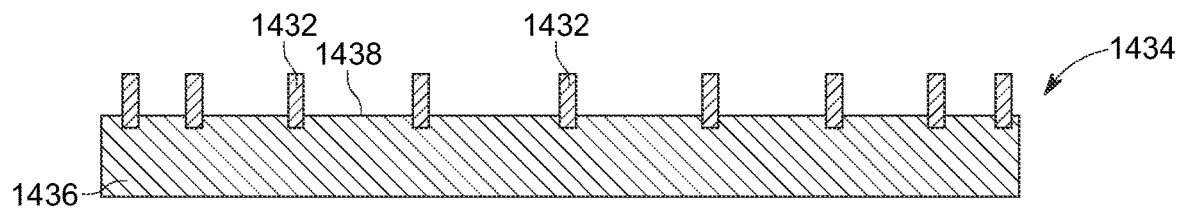
FIG. 50D illustrates a fourth stage of a method of using a stenciling system to make a shell having integral ribs, in accordance with one embodiment of the present patent application.

Referring to FIG. 50D, in one embodiment, the shell 1420 may be removed from the disk 1400 (FIG. 50C) so that the implant shell 1434 has a first layer 1436 that is smooth and an opposite second layer 1438 that has the ribs 1432 integrally formed therewith. In one embodiment, the implant shell 1434 may be configured so that the first surface 1436 of the shell defines an outer surface of the shell and the second surface 1438 defines an inner surface of the shell, whereby the ribs 1432 are integrally formed with the inner surface 1438 and extend inwardly from the inner surface.

Figure 51A:
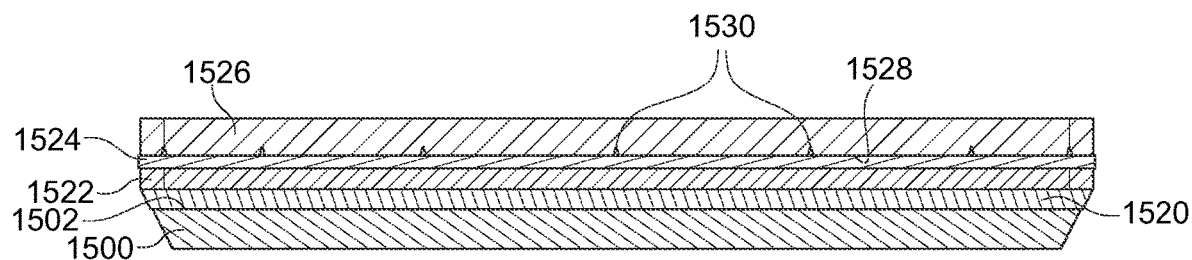
FIG. 51A is a cross-sectional view of a stenciling system used for making shells having integral ribs, in accordance with one embodiment of the present patent application.
Figure 51B:
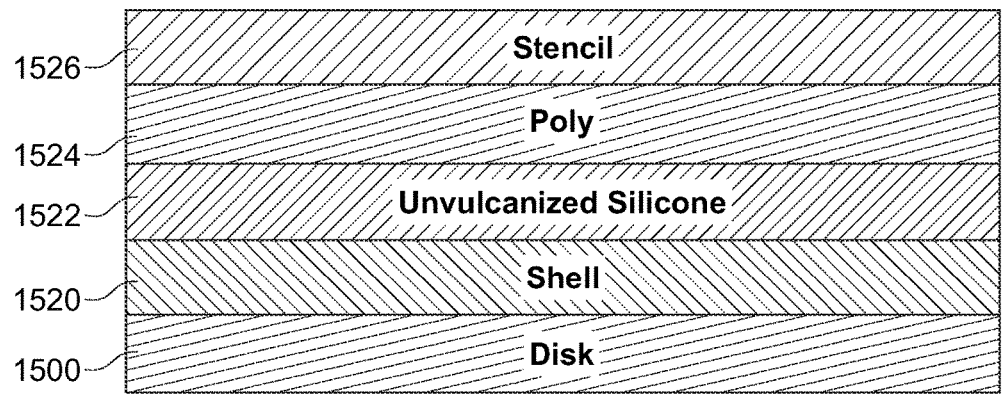
FIG. 51B is a schematic view of the stenciling system shown in FIG. 51A.

Referring to FIG. 51A and 51B, in one embodiment, a stenciling system for forming ribs on an implant shell preferably includes a disk 1500 having a top surface 1502 with a shell 1520 (e.g., a silicone shell) overlying the top surface 1502 of the disk 1500. In one embodiment, the outer perimeter of the shell 1520 may be stretched over the outer perimeter of the disk 1500 for securing the shell 1520 in place over the top surface 1502 of the disk 1500. In one embodiment, a rib forming sheet 1522, such as an unvulcanized silicone layer, may be applied over a major surface of the shell 1520, and a release layer 1524, such as a polyethylene sheet, may be laid over rib forming sheet 1522. In one embodiment, a stencil 1526 may be juxtaposed with the disk 1500 for compressing the shell layer 1520, the rib forming sheet 1522, and the release layer 1524 therebetween. The stencil 1526 desirably has an underside 1528 with grooves 1530 formed therein for forming ribs from the rib forming sheet 1522 as the stencil 1526 is compressed toward the top surface 1502 of the disk 1500. The grooves 1530 preferably define a rib pattern that will be pressed into the rib forming sheet to form the ribs.

Figure 52:
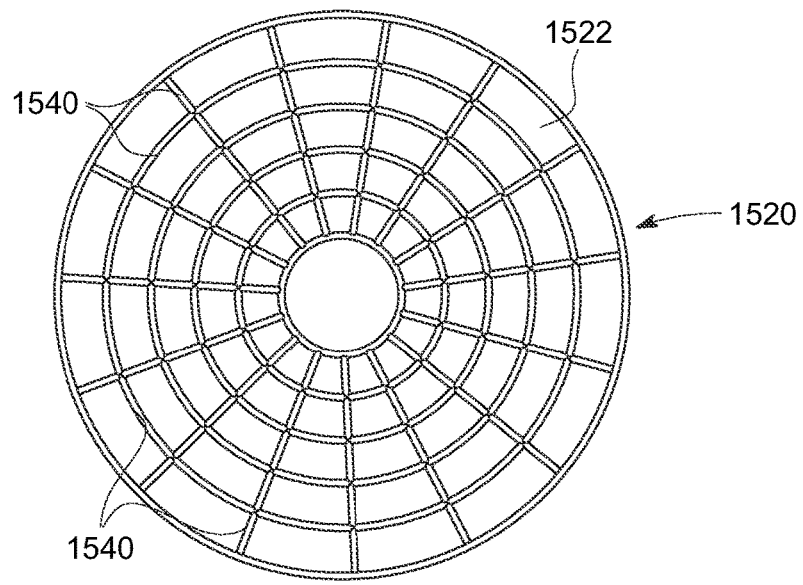
FIG. 52 is a top plan view of an inner surface of an implant shell having integral ribs that have been formed using the stenciling system shown in FIGS. 51A and 51B, in accordance with one embodiment of the present patent application.

Referring to FIG. 52, in one embodiment, when the stencil of FIGS. 51A and 51B is pressed toward the opposing disk, the stencil desirably forms ribs 1540 in the rib forming sheet 1522. During compression of the stencil toward the disk, the rib forming sheet is shaped into ribs that are integrally secured to the top surface of the shell 1520 (FIGS. 51A and 51B). The assembly shown in FIGS. 51A-51B and 52 may be cured for providing an implant shell having ribs projecting from a major surface thereof.

Figure 53:
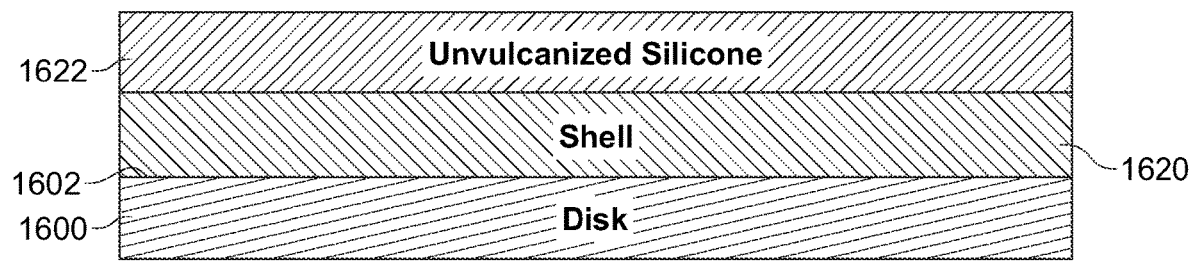
FIG. 53 is a schematic view of a stenciling system for making a shell having integral ribs, in accordance with one embodiment of the present patent application.
Figure 54:
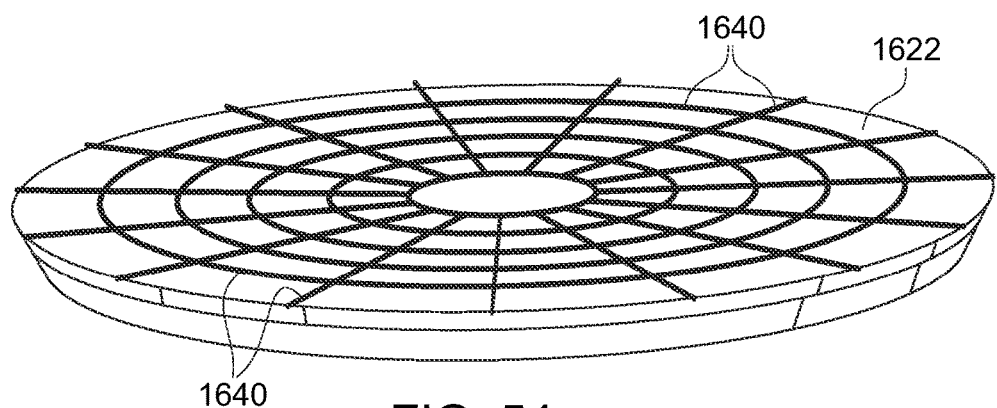
FIG. 54 illustrates a stage of a method of forming ribs on the shell shown in FIG. 53.
Figure 55:
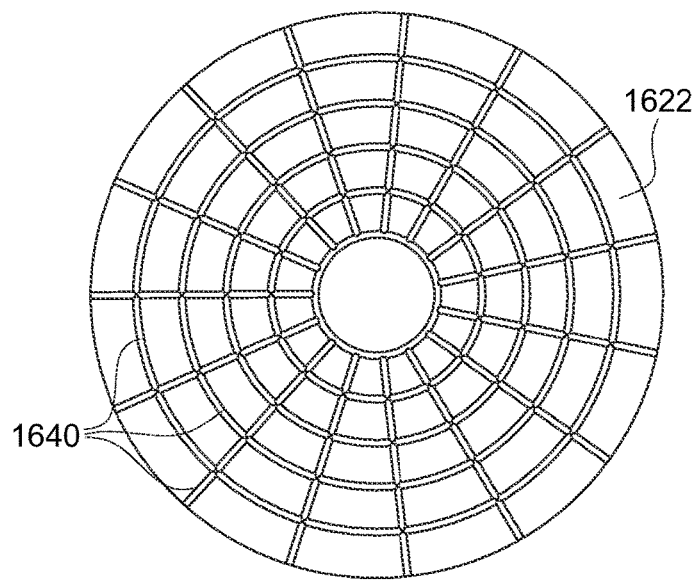
FIG. 55 is a top plan view of the shell shown in FIG. 54.

Referring to FIGS. 53-55, in one embodiment, a preformed shell 1620 (e.g., a silicone shell) may be stretched over the outer perimeter of a disk 1600 so that a major surface of the shell overlies a top surface 1602 of the disk. In one embodiment, a rib forming layer 1622 (e.g., an unvulcanized silicone sheet) may be provided over a major surface of the shell 1620 that is stretched over the top surface 1602 of the disk 1600.

Referring to FIGS. 54 and 55, in one embodiment, a stencil (e.g., the stencil 1526 shown in FIG. 51A) having a groove pattern may be pressed into the rib forming layer 1622 for forming a rib pattern, which desirably mirrors the groove pattern on the stencil. The subassembly shown in FIGS. 54 and 55 may be cured, such as by using heat, to form an implant shell having ribs extending from a major surface thereof. In one embodiment, the implant shell may be configured so that an outer surface of the shell is smooth and the ribs are located inside the shell and project inwardly from an inner surface of the shell. The implant shell may be filled with a gel or a saline solution to provide an implantable prosthesis.

Figure 56:
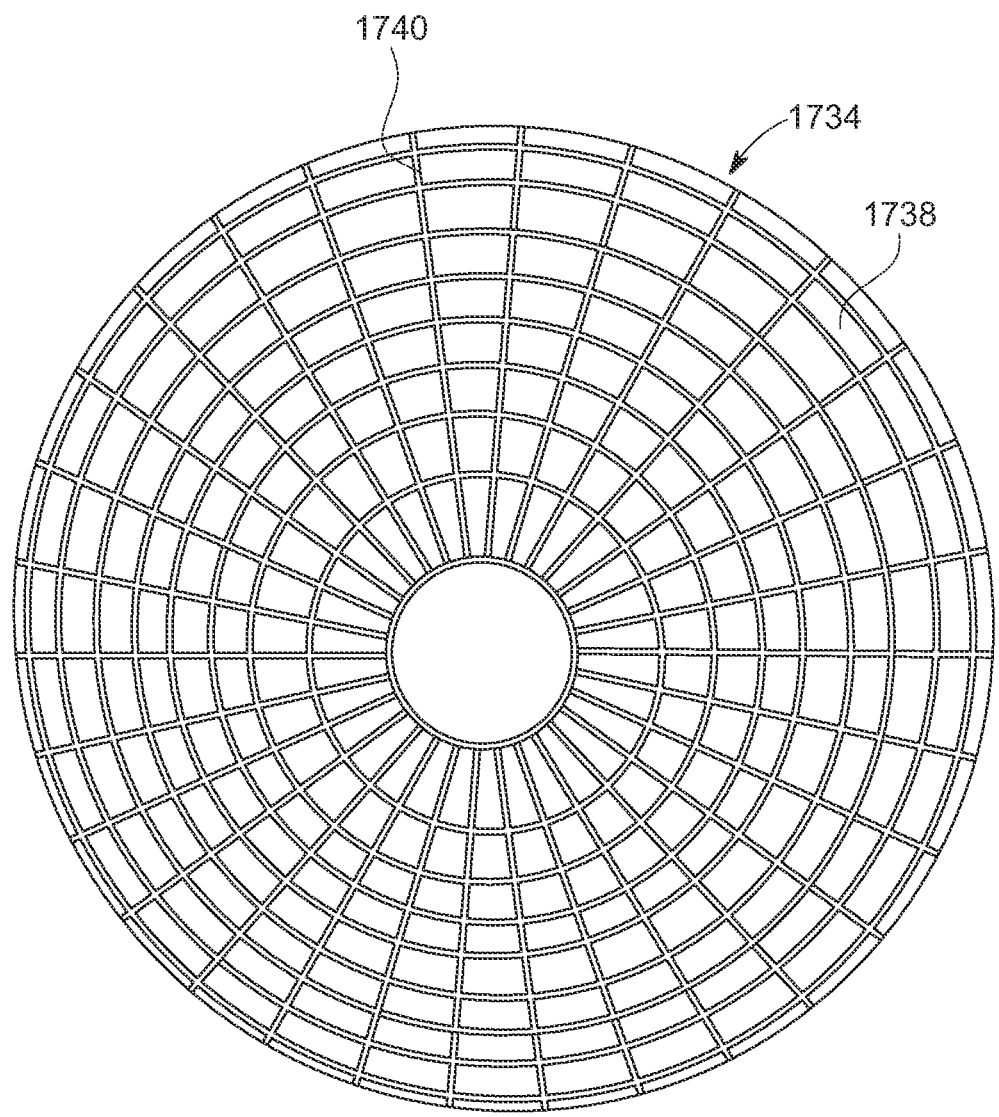
FIG. 56 is a top plan view of a shell having an inner surface with ribs formed on the inner surface of the shell, in accordance with one embodiment of the present patent application.

Referring to FIG. 56, in one embodiment, an implant shell 1734 preferably has an inner surface 1738 with a plurality of ribs 1740 projecting from the inner surface 1738. The ribs 1740 preferably define a rib pattern that mirrors a pattern provided on a stencil that is utilized to compress the inner surface 1738 of the implant shell 1734.

Figure 57A:
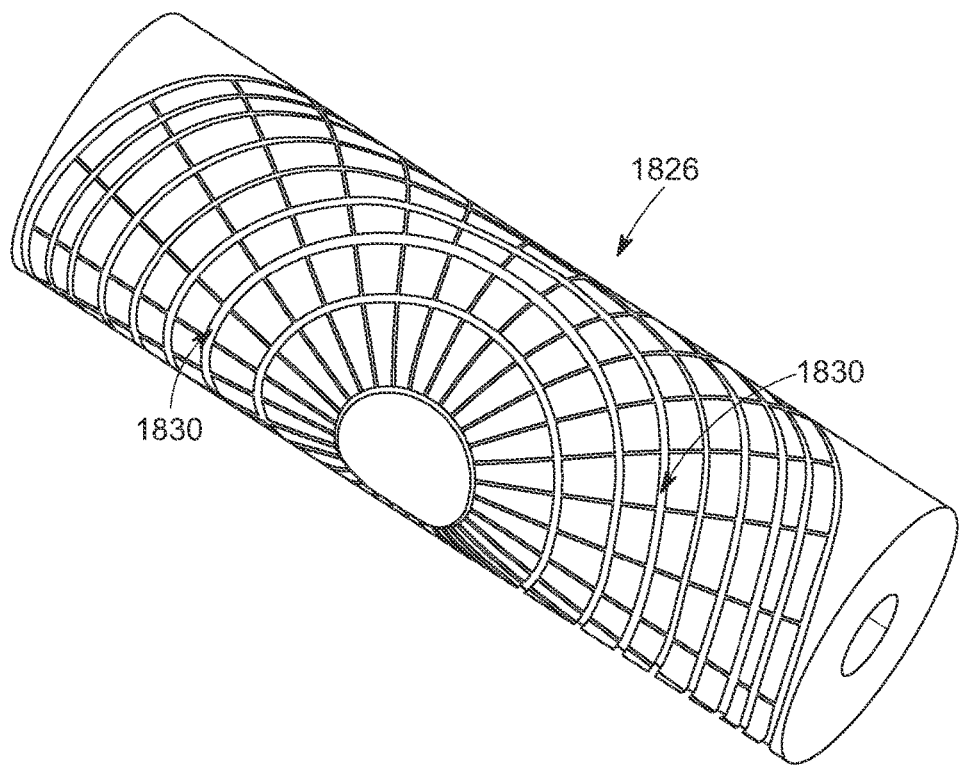
FIG. 57A is a perspective view of an embossing roller used to form ribs on a surface of a shell, in accordance with one embodiment of the present patent application.
Figure 57B:
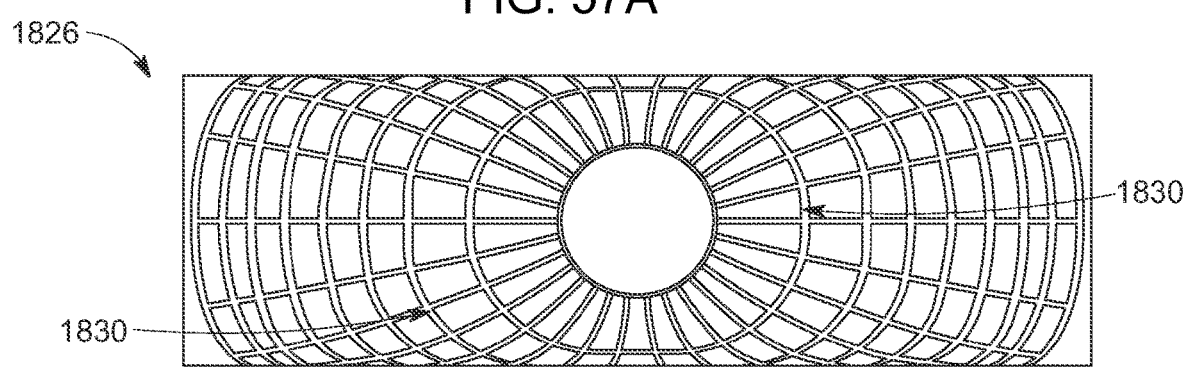
FIG. 57B is a front elevation view of the embossing roller shown in FIG. 57A.
Figure 57C:
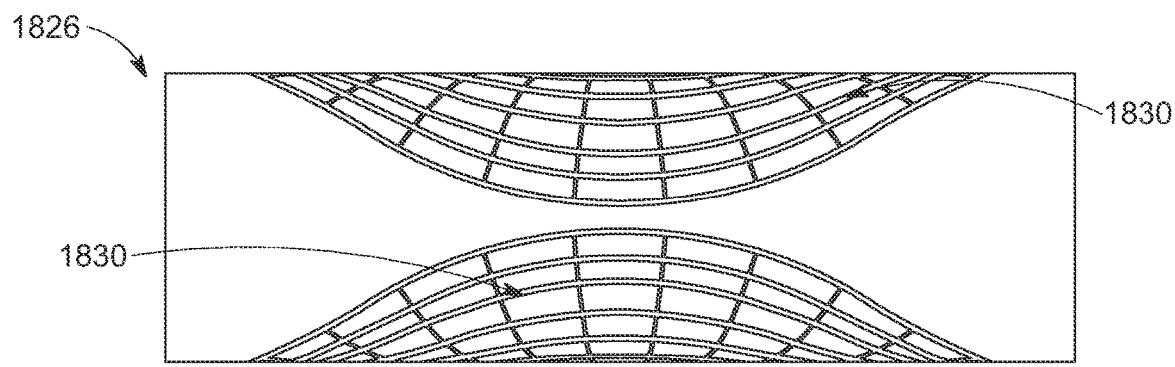
FIG. 57C is another front elevation view of the embossing roller shown in FIG. 57A.

Referring to FIGS. 57A-57C, in one embodiment, an embossing roller 1826 has grooves 1830 or a stencil pattern provided on an outer surface thereof, which may be used for forming a rib pattern on substrate such as a surface of a shell or a rib forming layer (e.g., an unvulcanized silicone sheet). In one embodiment, the outer surface of the embossing roller 1826 may be rolled over a major surface of a shell, such as a silicone shell stretched over a disk, as shown and described above in FIGS. 49A-49B and 52A-52B. The embossing roller may have a groove pattern formed in the outer surface thereof that is similar to the pattern on the device used to form the rib pattern shown on the shell in FIG. 56.

Figure 58A:
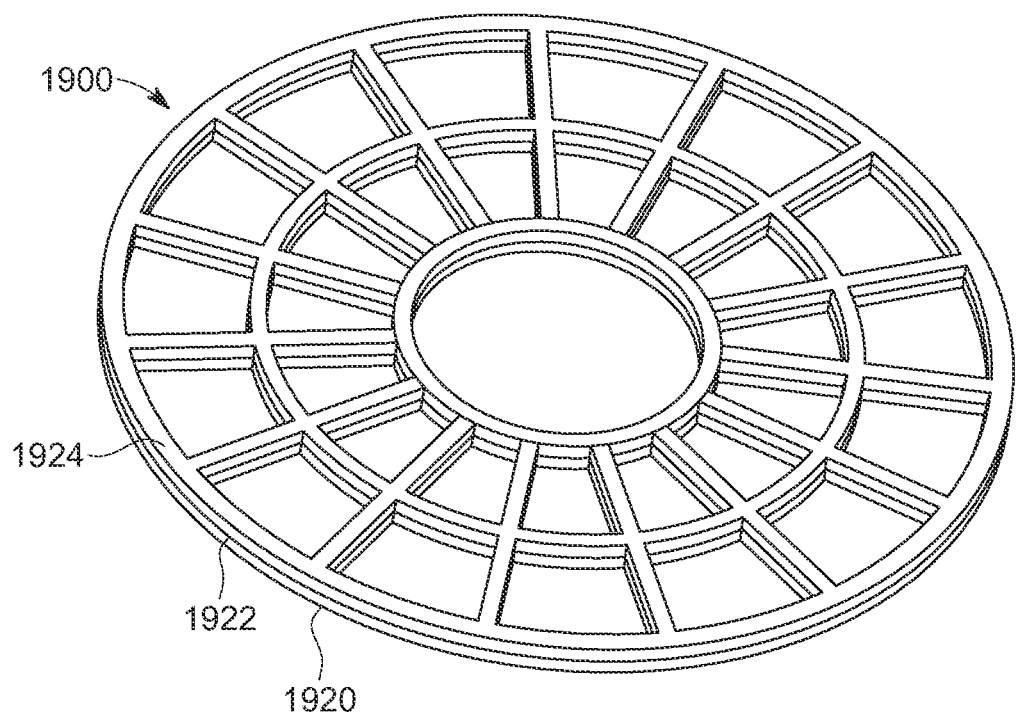
FIG. 58A is a perspective view a sheet having pre-cut ribs for making a shell having integral ribs, in accordance with one embodiment of the present patent application.
Figure 58B:
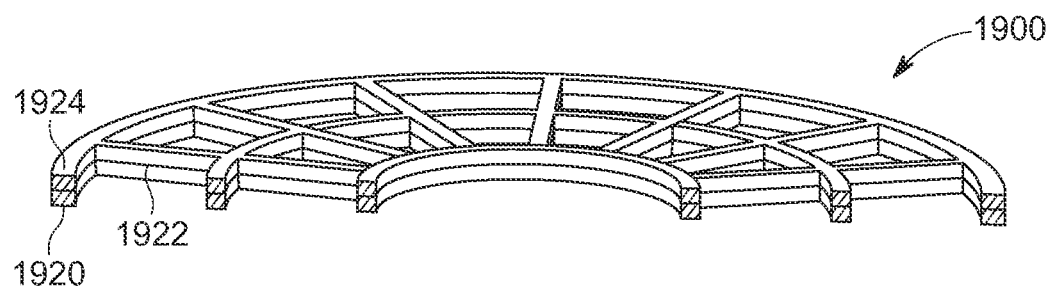
FIG. 58B is a cross-sectional view of the sheet having the pre-cut ribs shown in FIG. 58A.

Referring to FIGS. 58A and 58B, in one embodiment, a sheet 1900 may have a rib pattern pre-cut in the sheet. The pre-cut sheet 1900 may include a cured silicone layer 1920 having a top surface 1922 that is tacky or partially cured and a releasable liner 1924 that covers the tacky layer 1922. In one embodiment, the pre-cut sheet has a rib pattern cut into both the silicone layer 1920 and the releasable liner 1924. In one embodiment, the releasable liner 1924 may be removed to expose the tacky surface 1922 of the silicone layer 1920, and the tacky surface 1922 may be applied or affixed over a surface of a pre-formed implant shell that is stretched over a disk (FIG. 50).

Figure 59:
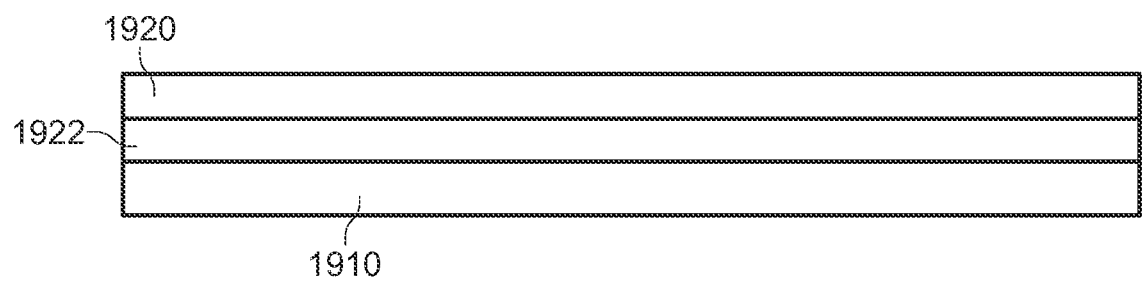
FIG. 59 is a cross-sectional view of a shell and the sheet having the pre-cut ribs of FIGS. 58A and 58B overlying a top surface of the shell, in accordance with one embodiment of the present patent application.

Referring to FIG. 59, in one embodiment, after the releasable liner 1924 is removed, the tacky surface 1922 of the pre-cut rib pattern 1920 may be juxtaposed with a major surface of a pre-formed implant shell 1910 to apply the rib pattern to the major surface of the shell 1910.

Figure 60A:
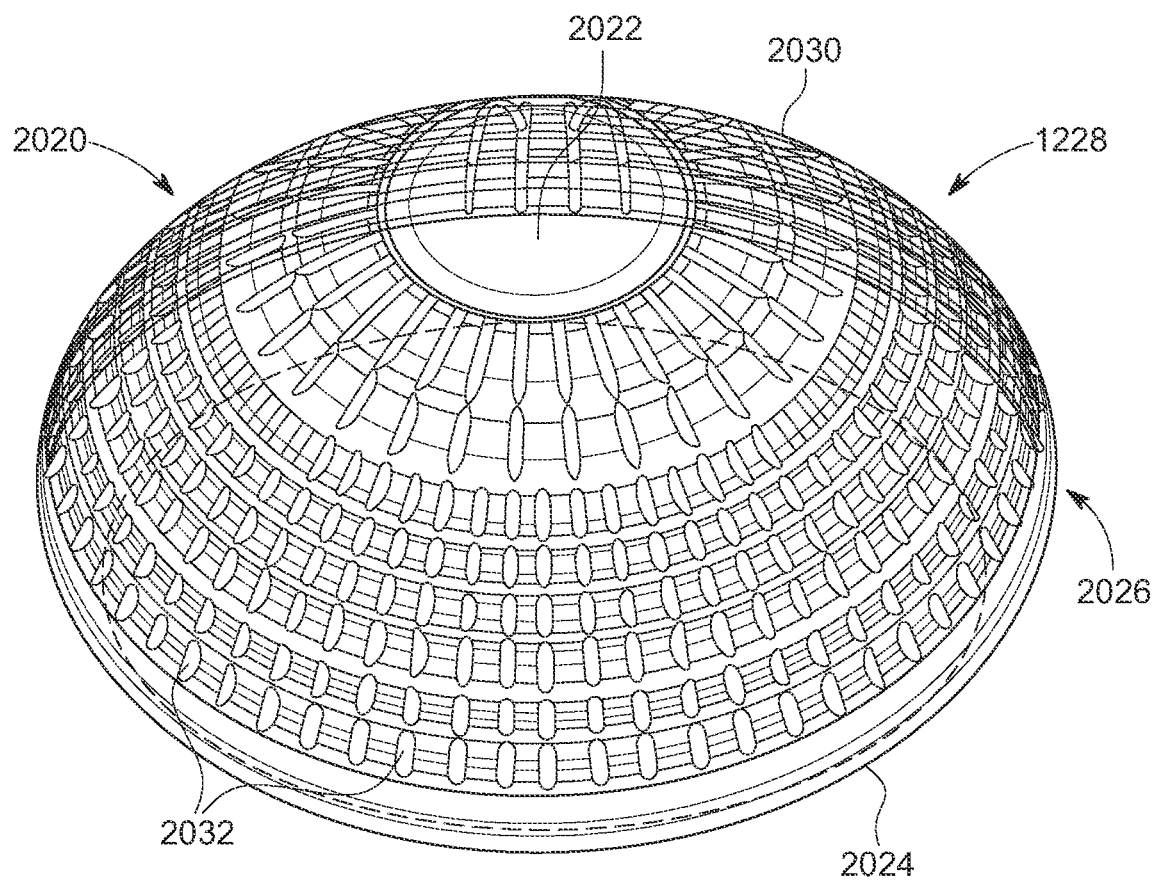
FIG. 60A is a perspective view a shell having a smooth outer surface and an inner surface having integral ribs, in accordance with one embodiment of the present patent application.
Figure 60B:
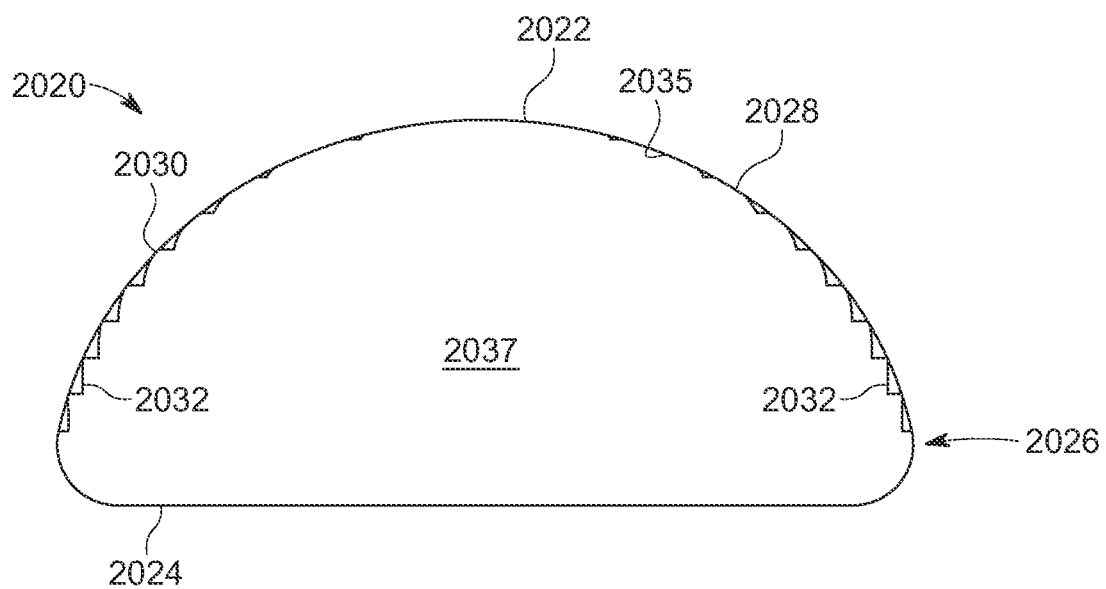
FIG. 60B is a cross-sectional view of the shell shown in FIG. 60A.

Referring to FIGS. 60A and 60B, in one embodiment, a shell 2020 for a prosthetic device (e.g., a mammary implant, a tissue expander) preferably has an apex 2022, a base 2024, a radius 2026, and a dome 2028 that extends between the apex 2022 and the base 2024. The shell 2020 desirably includes a convexly curved outer surface 2030 that extends between the apex 2022 and the base 2024. The outer surface 2030 of the implant shell 2020 is preferably substantially smooth. The inner surface 2035 of the implant shell 2020 desirably has ribs 2032 integrally formed with the inner surface 2035 that extend inwardly toward an interior volume 2037 of the implant shell 2020. The ribs 2032 may extend vertically, radially, diagonally and/or circumferentially. The interior volume 2037 of the shell may be filled with a gel or a saline solution for filling the implant shell 2020 to provide a prosthetic device.

Figure 61A:
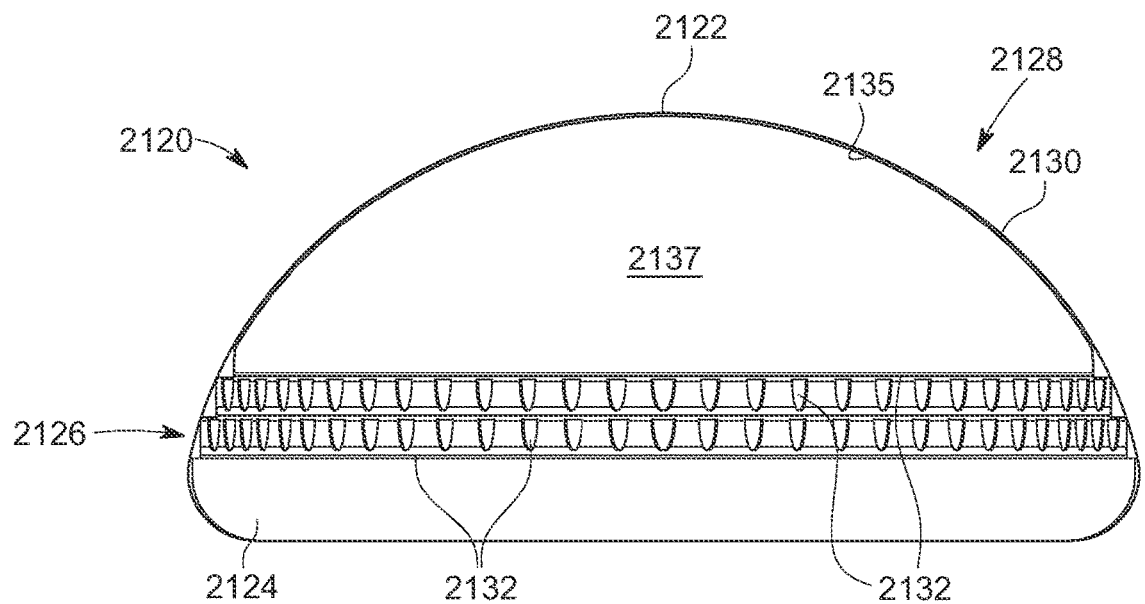
FIG. 61A is a perspective view a shell having a smooth outer surface and an inner surface having integral ribs, in accordance with one embodiment of the present patent application.
Figure 61B:
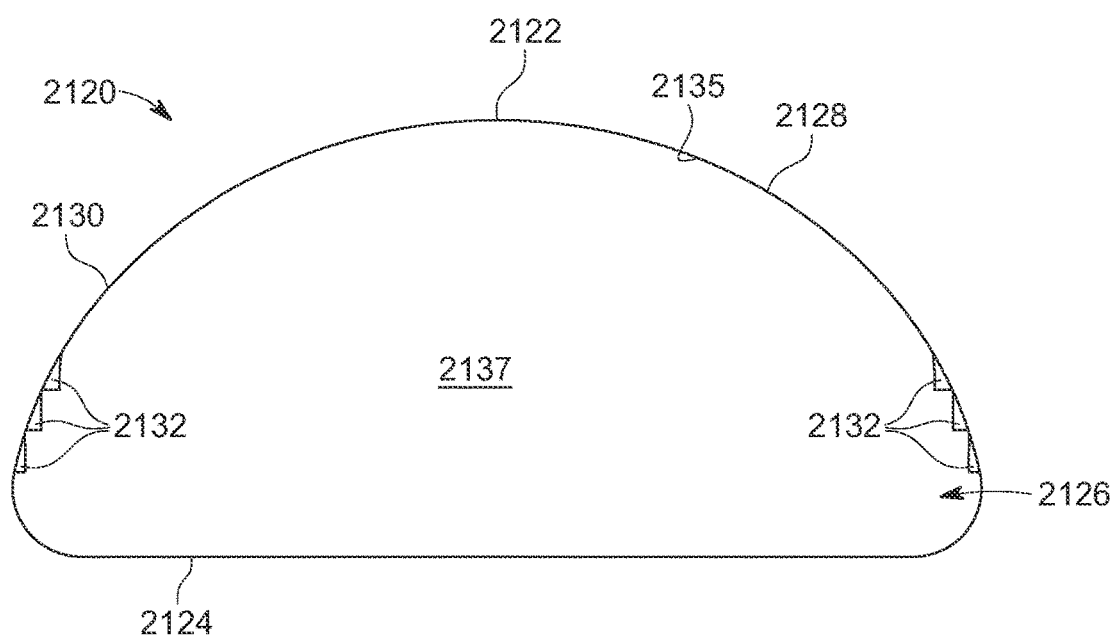
FIG. 61B is a cross-sectional view of the shell shown in FIG. 61A.

Referring to FIGS. 61A and 61B, in one embodiment, a shell 2120 for a prosthetic device (e.g., a mammary implant, a tissue expander) preferably has an apex 2122, a base 2124, a radius 2126, and a dome 2128 that extends between the apex 2122 and the base 2124. The shell 2120 desirably includes a convexly curved outer surface 2130 that extends between the apex 2122 and the base 2124. The outer surface 2130 of the implant shell 2120 is preferably substantially smooth. The inner surface 2135 of the implant shell 2120 desirably has circumferential ribs 2132 integrally formed with the inner surface 2135 that extend inwardly toward an interior volume 2137 of the implant shell 2120. The interior volume 2137 may be filled with a gel or a saline solution for filling the implant shell 2020 to provide a prosthetic device.

Figure 62:
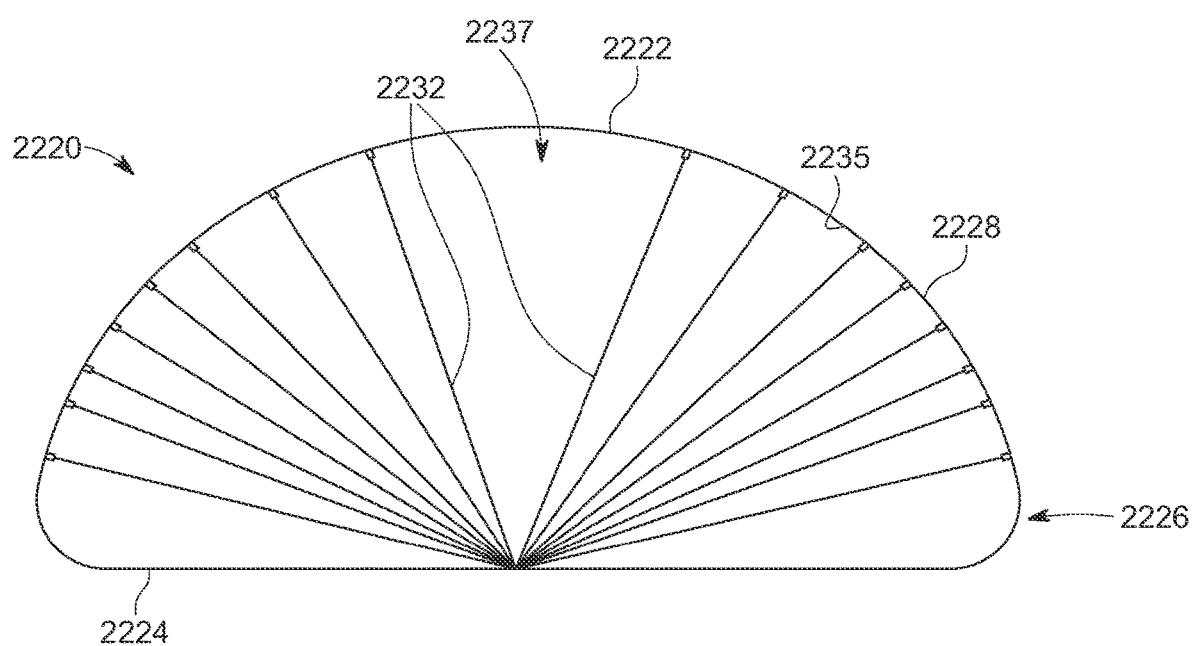
FIG. 62 is a cross-sectional view of a shell having a smooth outer surface and an inner surface having integral ribs, in accordance with one embodiment of the present patent application.

Referring to FIG. 62, in one embodiment, a shell 2120 for a prosthetic device (e.g., a mammary implant, a tissue expander) preferably has an apex 2222, a base 2224, a radius 2226, and a dome 2228 that extends between the apex 2222 and the base 2224. The shell 2220 desirably includes a convexly curved outer surface 2230 that extends between the apex 2222 and the base 2224. The outer surface 2230 of the implant shell 2220 is preferably substantially smooth. The inner surface 2235 of the implant shell 2220 desirably has ribs 2232 that are integrally formed with the inner surface 2235 and that extend inwardly toward an interior volume 2237 of the implant shell 2220. The ribs 2232 may have extend diagonally and/or radially over the inner surface of the shell. The interior volume 2237 of the shell may be filled with a biocompatible material (e.g., a gel or a saline solution) for filling the implant shell 2220 so that the shell may be used as a prosthetic device (e.g., a mammary implant, a tissue expander).

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. An implantable prosthesis comprising:
    a shell having an apex, a base, a radius located between said apex and said base, and a dome extending between said apex and said radius;
    said shell having an outer surface and an inner surface that surrounds an interior volume of said shell; and
    at least one rib integrally formed with said inner surface of said shell and projecting inwardly from said inner surface into said interior volume of said shell, wherein said at least one rib is integrally formed with and extends over said apex of said shell, wherein said at least one rib includes a second rib that extends over said apex of said shell.

2. The implantable prosthesis as claimed in claim 1, wherein said shell comprises a biocompatible polymer material, and wherein said implantable prosthesis further comprises a biocompatible filler material disposed within said interior volume of said shell that is selected from the group consisting of gel, silicone gel, saline, foam, air, and gas.

3. The implantable prosthesis as claimed in claim 1, wherein said at least one rib comprises at least one circumferential rib that is integrally formed with said inner surface of said shell and that projects inwardly from said inner surface of said shell.

4. The implantable prosthesis as claimed in claim 3, wherein said at least one circumferential rib comprises two or more circumferential ribs that are spaced from one another over said inner surface of said shell.

5. The implantable prosthesis as claimed in claim 4, wherein each of said two or more circumferential ribs has a constant depth of about 0.015-0.50 inches relative to said inner surface of said shell.

6. The implantable prosthesis as claimed in claim 4, wherein each of said two or more circumferential ribs has a height associated therewith.

7. The implantable prosthesis as claimed in claim 3, wherein said at least one rib comprises at least one radially extending rib that is integrally formed with said inner surface of said shell and that extends from said apex toward said base of said shell and extends over said apex and said dome of said shell.

8. The implantable prosthesis as claimed in claim 7, wherein said at least one radially extending rib comprises two or more radially extending ribs that are spaced from one another over said inner surface of said shell and that extend along respective axes that intersect with said at least one circumferential rib.

9. The implantable prosthesis as claimed in claim 1, wherein said second rib extends in a radial direction that runs from said apex toward said base of said shell.

10. The implantable prosthesis as claimed in claim 9, wherein said second rib extends over said apex and said dome of said shell.

11. The implantable prosthesis as claimed in claim 1, wherein said at least one rib includes a third rib that extends in a circumferential direction around one or more sides of said shell.

12. The implantable prosthesis as claimed in claim 1, wherein said at least one rib includes a third rib that extends in a radial direction that runs from said apex to said base of said shell, and wherein said third rib extends over said apex and said dome of said shell.

13. An implantable prosthesis comprising:
a shell having an apex, a base, a radius located between said apex and said base, and a dome extending between said apex and said radius;
said shell having an outer surface and an inner surface that surrounds an interior volume of said shell; and
two or more ribs that are integrally formed with said inner surface of said shell and that project inwardly from said inner surface of said shell into said interior volume of said shell, wherein said two or more ribs that are integrally formed with said inner surface of said shell are spaced from one another and extend in circumferential directions around said dome of said shell.

14. The implantable prosthesis as claimed in claim 13, wherein each of said two or more ribs have respective free ends spaced inwardly from said inner surface of said shell.

15. The implantable prosthesis as claimed in claim 13, wherein said shell comprises a biocompatible polymer material, and wherein said implantable prosthesis further comprises a biocompatible filler material disposed within said interior volume of said shell that is selected from the group consisting of gel, silicone gel, saline, foam, air, and gas.

16. The implantable prosthesis as claimed in claim 13, further comprising an additional rib that is integrally formed with said inner surface of said shell and that extends over said apex of said shell.

17. The implantable prosthesis as claimed in claim 16, wherein said additional rib has a free end that is spaced inwardly from said inner surface of said shell.

18. The implantable prosthesis as claimed in claim 17, wherein said inner surface of said shell comprises a concave curved surface, wherein said free end of said additional rib is curved for conforming to said concave curved surface of said shell.

19. The implantable prosthesis as claimed in claim 17, wherein said additional rib extends in a circumferential direction over said apex of said shell.

20. The implantable prosthesis as claimed in claim 17, wherein said additional rib extends in a radial direction over said apex of said shell.

21. The implantable prosthesis as claimed in claim 17, wherein said additional rib extends in a radial direction over said apex and said dome of said shell.

* * * * *